(12) United States Patent
Krantz et al.

(10) Patent No.: US 10,329,321 B2
(45) Date of Patent: Jun. 25, 2019

(54) SITE-SELECTIVE FUNCTIONALIZATION OF PROTEINS USING TRACELESS AFFINITY LABELS

(71) Applicants: Alexander Krantz, Boston, MA (US); Andrzej Wilczynski, Boston, MA (US)

(72) Inventors: Alexander Krantz, Boston, MA (US); Andrzej Wilczynski, Boston, MA (US)

(73) Assignees: Alexander Krantz, Boston, MA (US); Andrzej Wilczynski, Boston, MA (US)

( * ) Notice: Subject to any disclaimer, the term of this patent is extended or adjusted under 35 U.S.C. 154(b) by 0 days.

(21) Appl. No.: 15/427,678

(22) Filed: Feb. 8, 2017

(65) Prior Publication Data

US 2017/0275331 A1 Sep. 28, 2017

Related U.S. Application Data

(60) Provisional application No. 62/494,420, filed on Aug. 8, 2016, provisional application No. 62/390,624, filed on Apr. 4, 2016, provisional application No. 62/389,137, filed on Feb. 18, 2016, provisional application No. 62/388,862, filed on Feb. 9, 2016.

(51) Int. Cl.
| | |
|---|---|
| *C07K 1/13* | (2006.01) |
| *A61K 31/55* | (2006.01) |
| *C07K 1/06* | (2006.01) |
| *C07K 1/08* | (2006.01) |
| *C07K 16/32* | (2006.01) |
| *G01N 33/532* | (2006.01) |
| *A61K 47/65* | (2017.01) |
| *A61K 47/60* | (2017.01) |
| *A61K 47/62* | (2017.01) |
| *A61K 47/68* | (2017.01) |

(52) U.S. Cl.
CPC ............... *C07K 1/13* (2013.01); *A61K 31/55* (2013.01); *A61K 47/60* (2017.08); *A61K 47/62* (2017.08); *A61K 47/65* (2017.08); *A61K 47/68* (2017.08); *A61K 47/6803* (2017.08); *C07K 1/062* (2013.01); *C07K 1/084* (2013.01); *C07K 16/32* (2013.01); *G01N 33/532* (2013.01); *C07K 2317/24* (2013.01)

(58) Field of Classification Search
CPC . C07K 1/13; C07K 16/18; C07K 4/00; A61K 47/6803; A61K 49/0056
See application file for complete search history.

(56) References Cited

U.S. PATENT DOCUMENTS

| | | | |
|---|---|---|---|
| 4,833,092 A | 5/1989 | Geysen | |
| 5,010,175 A | 4/1991 | Rutter et al. | |
| 5,182,366 A | 1/1993 | Huebner et al. | |
| 5,270,170 A | 12/1993 | Schatz et al. | |
| 5,612,034 A | 3/1997 | Pouletty et al. | |
| 8,741,291 B2 | 6/2014 | Bhat et al. | |

FOREIGN PATENT DOCUMENTS

| | | | | |
|---|---|---|---|---|
| WO | 1992/000091 A1 | 1/1992 | | |
| WO | 1992/009300 A1 | 6/1992 | | |
| WO | 1993/006121 A1 | 4/1993 | | |
| WO | 1993/020242 A1 | 10/1993 | | |
| WO | 1994/006291 A1 | 3/1994 | | |
| WO | 1994/006451 A1 | 3/1994 | | |
| WO | 1995/028640 A1 | 10/1995 | | |
| WO | 2011/153250 A2 | 12/2011 | | |
| WO | WO-2014028803 A1 * | 2/2014 | ........... | C07D 405/14 |
| WO | WO-2015138907 A2 * | 9/2015 | ............. | C07K 16/00 |

OTHER PUBLICATIONS

Alves et al. (2012) "Small-molecule-based affinity chromatography method for antibody purification via nucleotide binding site targeting," Anal. Chem. 84:7721-8.
Alves et al. (Jun. 6, 2013) "Oriented antibody immobilization by site-specific UV photocrosslinking of biotin at the conserved nucleotide binding site for enhanced antigen detection," Biosens. Bioelectron. 49:387-393.
Berge et al. (1977) "Pharmaceutical salts," J. Pharm. Sci. 66:1-19.
Birtalan et al. (2008) "The intrinsic contributions of tyrosine, serine, glycine and arginine to the affinity and specificity of antibodies," J. Mol. Biol. 377(5):1518-1528.
Delano et al. (2000) "Convergent solutions to binding at a protein-protein interface," Science. 287(5456):1279-83.
Dias et al. (2006) "Protein ligand design: from phage display to synthetic protein epitope mimetics in human antibody Fc-binding peptidomimetics," J. Am. Chem. Soc. 128:2726-2732.
Fujishima et al. (2012) "Ligand-directed acyl imidazole chemistry for labeling of membrane-bound proteins on live cells," J. Am. Chem. Soc. 134(9):3961-3964.
Gordon et al. (1994) "Applications of combinatorial technologies to drug discovery. 2. Combinatorial organic synthesis, library screening strategies, and future directions," J. Med. Chem. 37(10):1387-401.
Handlogten et al. (2011) "Design of a heterobivalent ligand to inhibit IgE clustering on mast cells," Chem Biol. 18:1179-1188.
Kolb et al. (2001) "Click Chemistry: Diverse Chemical Function from a Few Good Reactions," Angew. Chem. Int. Ed. 40:2004-2021.
Lac et al. (Dec. 17, 2015) "Covalent Chemical Ligation Strategy for Mono- and Polyclonal Immunoglobulins at Their Nucleotide Binding Sites," Bioconjugate Chem. 27(1):159-169.
Le Droumaguet et al. (2010) "Fluorogenic click reaction," Chem. Soc. Rev. 39(4):1233-1239.
London et al. (2010) "The structural basis of peptide-protein binding strategies," Structure. 18(2):188-199.

(Continued)

*Primary Examiner* — Rachael E Bredefeld
*Assistant Examiner* — Kaipeen E Yang
(74) *Attorney, Agent, or Firm* — Brian C. Trinque; Lathrop Gage LLP

(57) ABSTRACT

The present disclosure relates to site-selective labeling compounds, and methods of using such compounds.

3 Claims, 37 Drawing Sheets

(56) References Cited

OTHER PUBLICATIONS

Rajagopalan et al. (1996) "Novel unconventional binding site in the variable region of immunoglobulins," Proc. Natl Scad. Sci. USA. 93(12):6019-6024.

International Search Report with Written Opinion corresponding to International Patent Application No. PCT/US2017/016932, dated May 25, 2017.

* cited by examiner

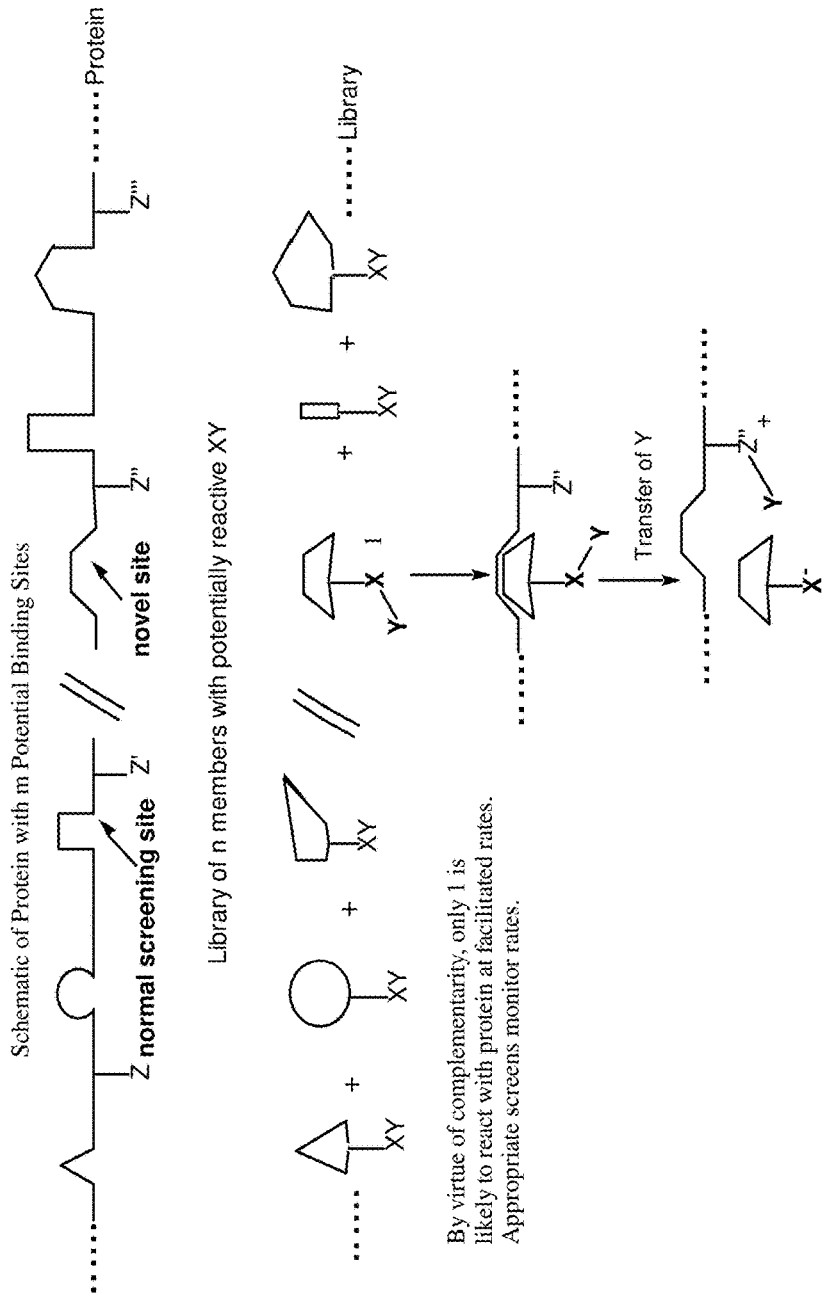

Fig. 3

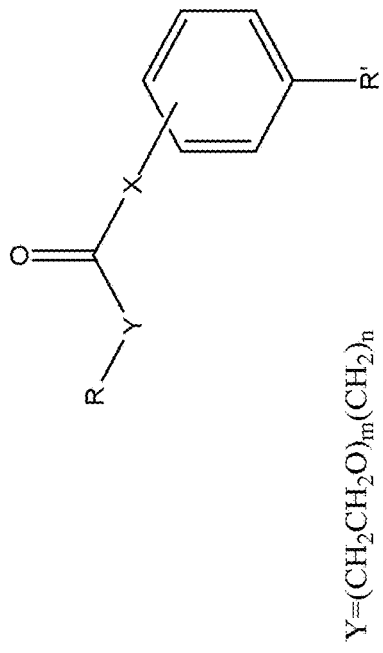

$Y=(CH_2CH_2O)_m(CH_2)_n$

I. R= alkynyl or cycloalkynyl, N=N=N-, formyl, acetyl, Diels-Alder diene; m=1-30; n=1-20; X=O, S, Se; [R'= -COR'', -SO$_2$R'', R''= N-terminus of a peptide and comprising up to 25 amino acid residues;]. [R'=CH$_2$R''', where R'''comprises the main chain segment of the tyrosine or thiotyrosine, which are part of a chain of from 1-40 amino acid residues.]; or [R'= -COR'''', -SO$_2$R'''', where R'''' is a 2,3-diaminopropionic acid residue within a main chain peptide comprising up to 25 residues linked at CO or SO$_2$ at the 2-amino group.]; or R'= -COR$^5$, -SO$_2$R$^5$ where R$^5$ is a peptide comprising up to 25 residues linked at its N-terminus to CO or SO$_2$ R' and RY—$\overset{O}{\underset{}{\vert}}$X— may be disposed o, p, or m; ring may be optionally substituted with -NO$_2$, -SO$_2$, -SO$_2$NHR$^5$, -OCH$_3$ and other ring subsitutents known in the art; R$^5$=H, alkyl.

Fig. 4

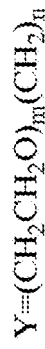

$RY\overset{O}{\underset{\|}{C}}X(CH_2)_m\overset{O}{\underset{\|}{C}}_{R'}$ $Y=(CH_2CH_2O)_m(CH_2)_n$ II. [R= alkynyl or cycloalkynyl, N=N=N-, formyl, acetyl, Diels-Alder diene; m=1-20; X=O, S, Se; R'= N-terminus of a peptide and comprising up to 25 amino acid residues]; [R= alkynyl or cycloalkynyl, N=N=N-, formyl, acetyl, Diels-Alder diene; m=1-30, n=1-30, n=1-20; X=O, S, Se; R' is a peptide comprising up to 25 residues linked at a 2,3-diaminopropionic acid residue.]

Fig. 5

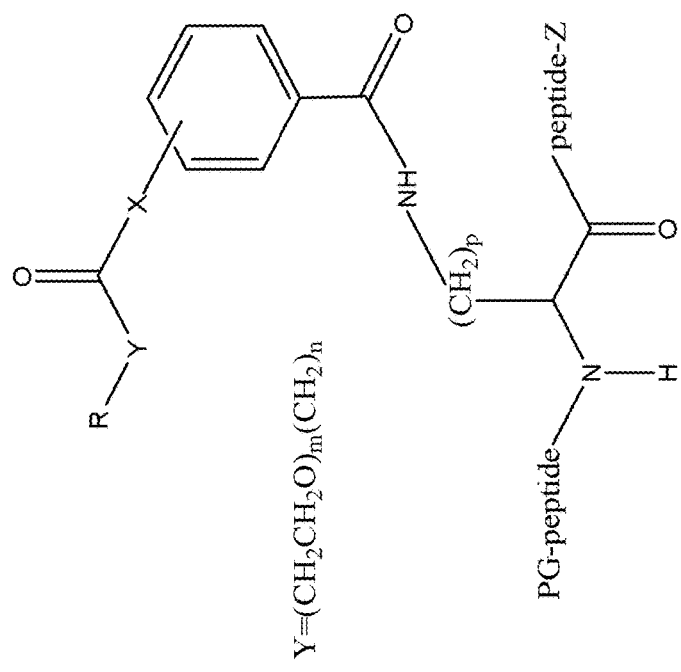

III. R= alkynyl or cycloalkynyl, N=N=N-, formyl, acetyl, Diels-Alder diene; m=1-30, n=1-20, p=1-8; X=O, S, Se; peptide (or peptoid may be from 0-25 amino acid residues and protected at the N-terminus by PG= t-BOC and the like; Z=OH, $NH_2$, NHR', NR'R'', R', R'', =alkyl or aryl.

Ring substituents as shown may be disposed o, p, or m; ring may be further optionally substituted with -$NO_2$, -$SO_2$, -$SO_2NHR'''$, -$OCH_3$ and other ring subsitutents known in the art; R'''=H, alkyl.

IV. R= alkynyl and cycloalkynyl, N=N=N⁻, formyl, acetyl, Diels-Alder diene; n=1-20; m=1-8; peptide may be from 0-25 amino acid residues and protected at the N-terminus by PG= t-BOC and the like; Z=OH, NH$_2$, NHR', NR"R'; R', R", =alkyl or aryl.

m=1-4; peptide may be from 0-25 amino acid residues and protected at the N-terminus by PG= t-BOC and the like; Y=OH, NH₂, NHR', NHR''; R', R'', =alkyl or aryl. SS=solid support.

V. R= alkynyl or cycloalkynyl, N=N=N⁻, formyl, acetyl, Diels-Alder diene; m=1-30, n=1-20, p=1-8; X=O, S, Se; ; peptide may be from 0-25 amino acid residues and protected at the N-terminus by PG= t-BOC and the like; Z=OH, NH₂, NHR', NR'R", R', R'', =alkyl or aryl.

Fig. 15
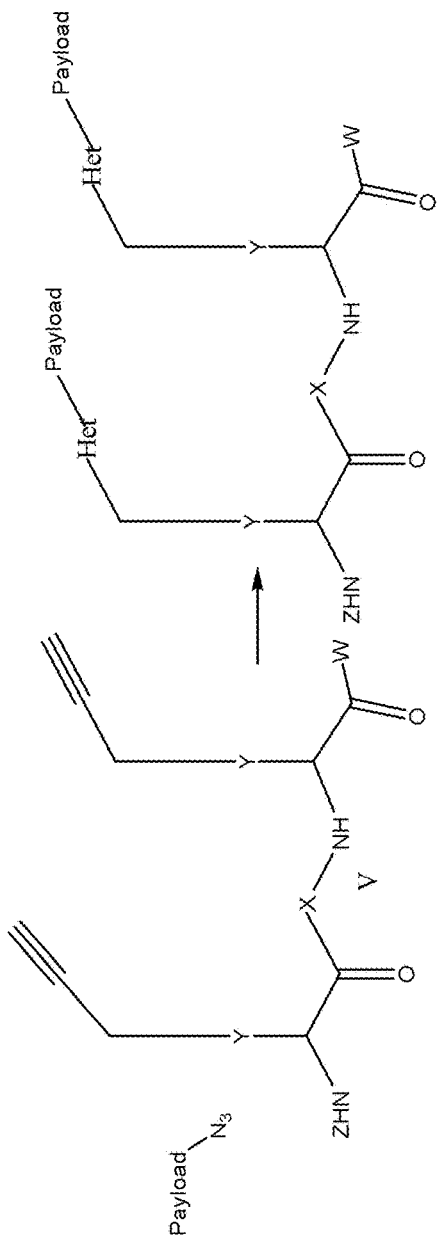
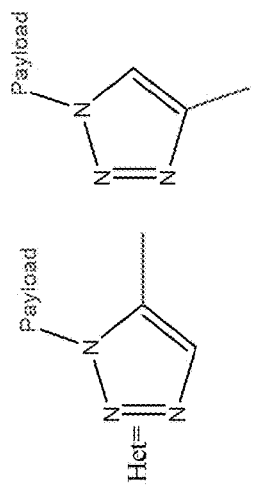
V, X, Z and W= independently, an amino acid or a linear or cyclic peptide, consisting of at least one amino acid or as many as 40, independently of either L- or D-configuration. Z may equal H, or t-BOC; W may equal OH or NH$_2$

SITE-SELECTIVE FUNCTIONALIZATION OF PROTEINS USING TRACELESS AFFINITY LABELS

RELATED APPLICATIONS

This application claims priority to U.S. Provisional Application No. 62/388,862, filed Feb. 9, 2016, U.S. Provisional Application No. 62/389,137, filed Feb. 18, 2016, U.S. Provisional Application No. 62/390,624, filed Apr. 4, 2016, and U.S. Provisional Application No. 62/494,420, filed Aug. 8, 2016, the entire contents of which are incorporated herein by reference.

FIELD OF THE INVENTION

The present invention relates generally to methods for the site-selective crosslinking of payloads to antibodies and other proteins. This can be accomplished through the agency of traceless affinity labels designed to label the target proteins with a bio-orthogonally reactive entities (ORE). In particular, the preferred target sites of this invention are the conserved sites (also referred to as consensus binding sites) of antibodies. The present invention also relates generally to systematic methods of screening an antibody for selective labeling of amino groups (e.g. surface lysines), and compositions leading to such selective labeling. In this aspect the method of screening accomplishes site-selective labeling in which the affinity group is traceless, e.g., does not appear in the product labeled with a bio-orthogonally reactive entity. The present invention further relates to practical, advanced methods for the site-selective labeling of antibodies with payloads through a stepwise process which enables the introduction of any one of a large variety of entities at selective sites on the antibody surface. The present invention further relates generally to the chemospecific union of antibodies with payloads through the agency of orthogonally reactive entities (ORE) that have become attached site-selectively to the antibody surface by combinatorial library methods or through innovative reformatting of known linkers. The present invention also relates to the characterization and use of such compositions for the purpose of augmenting or modulating the activity of the biological molecule, and/or to attach a payload, e.g., polymer, drug, macromolecule, imaging agent in order to improve the safety or efficacy of the antibody, or to introduce additional activities or payloads onto the protein framework. The present invention generally provides methods for the site-selective modification of monoclonal and polyclonal antibodies, their fragments (e.g., Fab, F(ab')$_2$, scFv (single-chain variable), sdAb (single domain antibody)), bi-specific antibodies, diabodies), and the like. The modifications described herein can be used for the attachment of payloads in radio-labeling, molecular imaging, optical probes, and numerous therapeutic antibody applications, and the treatment of many disorders which include rheumatoid arthritis, lupus erythematosus, psoriasis, multiple sclerosis, type-1 diabetes, Crohn's disease, and systemic sclerosis, Alzheimer disease, cancer, heart and liver disease (e.g., alcoholic liver disease), and cachexia.

BACKGROUND

A major gap in chemical modification technologies of proteins are the lack of methods for the site-selective/chemospecific labeling of lysines. Indeed, a general screen for the site-selective labeling of the most accessible lysines in proteins would be advantageous in a number of respects.

First, since most proteins contain numerous lysines it would provide optional, diverse candidates for conjugate development. The candidates would emerge from screens ranked in order of lysine selectivity. For projects which have had a restricted focus on a single target protein site for attachment, this feature is invaluable for diversifying the screening process and bringing it more in line with the "numbers game" of small molecule development. Regioisomers (positional isomers) of purified conjugates would be expected to have different properties (e.g., pharmacokinetic) that could provide insights for clinical development of the optimal conjugate.

Second, labor intensive molecular biology methods are rendered an unnecessary preliminary to introducing payloads onto proteins, as the native or commercially available proteins can be screened without prior modification.

Thirdly, amines can be targeted with diverse acylating entities to provide amide bonds that are among the most chemically stable under physiological conditions of pH and temperature.

Fourthly, affinity elements, and/or labeling entities to the targeted protein could be combined with information on known ligands to site-selectively label of the protein For these reasons, methods for the site-selective/chemospecific modification and ligation of proteins, and particularly antibodies, would be useful to produce and facilitate the formation of protein conjugates and related crosslinked products such as antibody-drug conjugates. The conjugates and crosslinked products themselves are useful in many respects including molecular diagnostic and therapeutic applications.

SUMMARY

In one aspect, provided herein is a compound comprising:
i. a peptide (W);
ii. a first orthogonally-reactive moiety (R); and
iii. a covalent attachment between W and R, comprising an electrophilic moiety;
wherein the electrophilic moiety is capable of reacting with an amino group of a protein, thereby breaking the covalent attachment between W and R.

In an embodiment, W is a peptide of 1-25, 4-15, 6-10 or 4-8 amino acid residues.

In an embodiment, the covalent attachment between W and R comprises an electrophilic moiety selected from —C(O)O—, —C(O)S—, —C(O)Se—, —SO$_2$O—, —SO$_2$S— and —SO$_2$Se—.

In an embodiment, no more than four positions of the peptide are fixed with W, F, Y, I, or L between the 3- and C-terminal position.

In an embodiment, R comprises a moiety selected from the group consisting of an alkyne, cycloalkyne, azide, 1,3-diene, nitrile oxide, nitrone, tetrazine, trans-cyclooctene, and carbonyl (e.g., aldehyde).

In an embodiment, the present disclosure relates to a compound having the structure of formula (II):

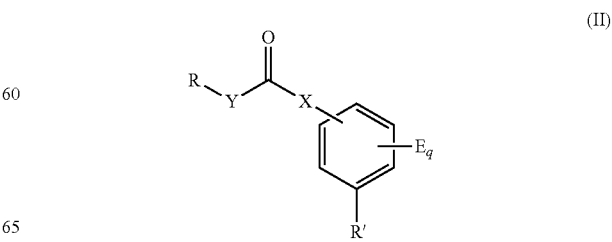

wherein

E is a moiety selected from the group consisting of halogen, —CN, —NO$_2$, —SO$_2$, —SO$_2$NHW$^4$, —S(O)C$_1$-C$_6$ alkyl, —S(O)aryl, and —OC$_1$-C$_6$ alkyl;

X is O, S or Se;

Y is a linker selected from the group consisting of alkyl, polyalkylene oxide, peptide, peptoid, and combinations thereof;

R is selected from the group consisting of an alkyne, cycloalkyne, azide, 1,3-diene, nitrile oxide, nitrone, tetrazine, trans-cyclooctene, and carbonyl (e.g., aldehyde); and R' is —C(O)W$^1$, —SO$_2$W$^1$, —CH$_2$W$^2$, —C(O)W$^3$, —SO$_2$W$^3$, —C(O)W$^4$ or —SO$_2$W$^4$; wherein W$^1$ comprises a linear peptide of 1-25 amino acid residues, attached to C(O) or SO$_2$ at the N-terminus;

W$^2$ comprises a peptide of 1-25 amino acid residues, attached to CH$_2$ at an O-tyrosine or S-thiotyrosine residue;

W$^3$ comprises a peptide of 1-25 amino acid residues, attached to C(O) or SO$_2$ at the P-amino group of a 2,P-diamino-n-alkanoic acid residue, wherein P is 3, 4, 5, 6, 7 or 8;

W$^4$ comprises a peptide of up to 25 residues, linked to C(O) or SO$_2$ at the N-terminus; and q is 0, 1, 2 3 or 4.

In an embodiment of formula (II), Y has the formula: —(CH$_2$CH$_2$O)$_m$(CH$_2$)$_n$— wherein m is 0-30 and n is 1-20.

In an embodiment of formula (II), W$^1$, W$^2$, W$^3$ and W$^4$ independently comprise peptides of 4-8 or 6-10 amino acid residues.

In an embodiment, the compound of formula (II) further comprises a biotin moiety.

In a particular embodiment, the compound formula (II) comprises the following moiety:

In a particular embodiment, the compound of formula (II) has the structure of formula (II-1):

wherein

X is —OH (compound 1a);

X is —NH$_2$ (compound 1b);

X is and R is —NH$_2$ (compound 2); or

X is and

R is (compound 3).

(II-1)

In an embodiment, the present disclosure relates to a compound having the structure of formula (III):

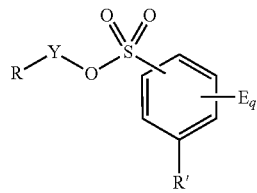

(III)

wherein

E is a moiety selected from the group consisting of halogen, —CN, —NO$_2$, —SO$_2$, —SO$_2$NHW$^4$, —S(O)C$_1$-C$_6$ alkyl, —S(O)aryl, and —OC$_1$-C$_6$ alkyl;

X is O, S or Se;

Y is a linker selected from the group consisting of alkyl, polyalkylenoxide, and combinations thereof;

R is selected from the group consisting of an alkyne, cycloalkyne, azide, 1,3-diene, nitrile oxide, nitrone, tetrazine, trans-cyclooctene, and carbonyl (e.g., aldehyde); and R' is —C(O)W$^1$, —SO$_2$W$^1$, —CH$_2$W$^2$, —C(O)W$^3$, —SO$_2$W$^3$, —C(O)W$^4$ or —SO$_2$W$^4$; wherein W$^1$ comprises a linear peptide of 1-25 amino acid residues, attached to C(O) or SO$_2$ at the N-terminus;

W$^2$ comprises a peptide of 1-25 amino acid residues, attached to CH$_2$ at an O-tyrosine or S-thiotyrosine residue;

W$^3$ comprises a peptide of 1-25 amino acid residues, attached to C(O) or SO$_2$ at the P-amino group of a 2,P-diamino-n-alkanoic acid residue, wherein P is 3, 4, 5, 6, 7 or 8;

W$^4$ comprises a peptide of up to 25 residues, linked to C(O) or SO$_2$ at the N-terminus; and q is 0, 1, 2 3 or 4.

In an embodiment of formula (III), Y has the formula: —(CH$_2$CH$_2$O)$_m$(CH$_2$)$_n$— wherein m is 0-30 and n is 1-20.

In an embodiment of formula (III), W$^1$, W$^2$, W$^3$ and W$^4$ independently comprise peptides of 4-8 or 6-10 amino acid residues.

In an embodiment, the present disclosure relates to a compound having the structure of formula (IV):

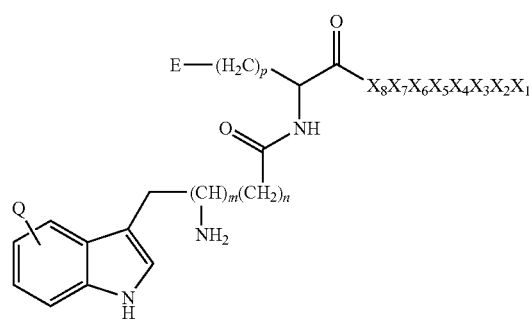

(IV)

wherein

E is selected from the group of:

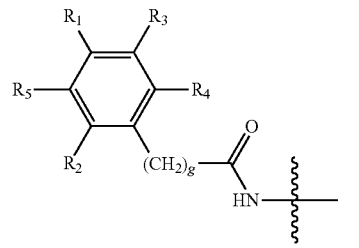

and

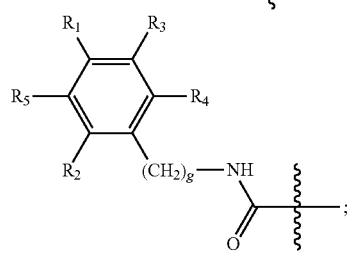

;

R$_1$, R$_2$, R$_3$, R$_4$, and R$_5$ independently, are selected from H, F, Cl, NO$_2$, CN and L, provided that only one of R$_1$, R$_2$, R$_3$, R$_4$, and R$_5$ is L;

L is R—(CH$_2$CH$_2$O)$_q$(CH$_2$)$_r$—C(O)—X— or R—(CH$_2$CH$_2$O)$_q$(CH$_2$)$_r$—X—SO$_2$—;

R is selected from the group consisting of an alkyne, cycloalkyne, azide, 1,3-diene, nitrile oxide, nitrone, tetrazine, trans-cyclooctene, and carbonyl (e.g., aldehyde);

X is 0 or S;

X$_1$, X$_2$, X$_3$, X$_4$, X$_5$, X$_6$, X$_7$ and X$_8$ independently are selected from residues of natural amino acids and 2,3-diaminopropionic acid, thiotyrosine, 4-benzoylphenylalanine, 2-thiazole-alanine, norvaline, 1-naphthylalanine, 2-naphthylalanine, 3-naphthylalanine, N-ε-carbamyl-lysine, 2-thienylalanine, 3-aminopyrrolidine-4-carboxylic acid, 2',4'-phenylalanine, 2',5'-phenylalanine, 2',6'-phenylalanine, 3',4'-phenylalanine, —OH, —O—(C$_1$-C$_6$)alkyl, —O-aryl, amino, —(C$_1$-C$_6$)alkylamino, di-(C$_1$-C$_6$)alkylamino, or are absent, provided that at least one of X$_1$, X$_2$, X$_3$, X$_4$, X$_5$, X$_6$, X$_7$ and X$_8$ are present;

Q is an electron-withdrawing substituent (e.g., haloalkyl, —F, —NO$_2$ or —CN);

g is 0-8; m is 0 or 1; n is 0-8; p is 1-8; r is 1-20; and q is 0-100.

In an embodiment of formula (IV), X$_1$, X$_2$, X$_3$, X$_4$, X$_5$, X$_6$, X$_7$ and X$_8$ independently are amino acid residues selected from the group of: glutamic acid, glutamine, aspartic acid, asparagine, arginine, methionine, serine, tyrosine, leucine, isoleucine, alanine, glycine, threonine, valine, proline, phenylalanine, tryptophan, 2,3-diaminopropionic acid, thiotyrosine, 4-benzoylphenylalanine, 2-thiazole-alanine, norvaline, 1-naphthylalanine, 2-naphthylalanine, 3-naphthylalanine, N-ε-carbamyl-lysine, 2-thienylalanine, 3-aminopyrrolidine-4-carboxylic acid, 2',4'-phenylalanine, 2',5'-phenylalanine, 2',6'-phenylalanine, 3',4'-phenylalanine, —OH, —O—(C$_1$-C$_6$)alkyl, —O-aryl, amino, —(C$_1$-C$_6$)alkylamino, di-(C$_1$-C$_6$)alkylamino, or are absent, provided that at least one of X$_1$, X$_2$, X$_3$, X$_4$, X$_5$, X$_6$, X$_7$ and X$_8$ are present.

In an embodiment of formula (IV), at least 2, at least 3, at least 4, at least 5, at least 6, at least 7, or 8 of X$_1$, X$_2$, X$_3$, X$_4$, X$_5$, X$_6$, X$_7$ and X$_8$ are present.

In an embodiment of formula (IV), at least four of $X_1$, $X_2$, $X_3$, $X_4$, $X_5$, $X_6$, $X_7$ and $X_8$ independently are an aromatic ring-containing amino acid, leucine, valine or isoleucine.

In another aspect, the present disclosure relates to a method for site-selectively functionalizing an amino group of a protein, comprising:

contacting the protein with any one of the compounds disclosed herein;

forming a covalent attachment between the amino group of the protein and the first orthogonally-reactive moiety of the compound; and breaking the covalent attachment between the first orthogonally-reactive moiety and the peptide;

to obtain a site-selectively functionalized protein.

In an embodiment of the method, the first orthogonally-reactive moiety comprises an azide.

In an embodiment, the protein is an antibody and the amino group is located in the Fab region of the antibody. In an embodiment, the antibody is a therapeutic antibody useful for the treatment of cancer or autoimmune diseases.

In an embodiment, the compound has an affinity for a conserved region of the protein. In an embodiment, the affinity is represented by a Kd of 100 μM or less. In an embodiment, the affinity is represented by a Kd of 10 μM or less.

In an embodiment, the method further comprises:

contacting the site-selectively functionalized protein with a payload compound, wherein the payload compound comprises a second orthogonally-reactive moiety; and forming one or more covalent bonds between the first orthogonally-reactive moiety and the second orthogonally-reactive moiety.

In an embodiment, the first orthogonally-reactive moiety comprises an azide, and wherein the second orthogonally-reactive moiety comprises an alkyne.

In an embodiment, the payload compound is an imaging moiety, antibody, antibody is fragment, protein, optical agent, vitamin, enzyme, peptide, peptoid, toxin, drug, prodrug, ligand to a biomarker, or stimulator of efferocytosis.

In an embodiment, the payload compound targets a receptor selected from the group consisting of folate, EGFR, ALK, MET, PTK7 and KRAS or any oncogene product.

In an embodiment, the payload compound is selected from the group of: anthracyclines, taxols, auristatins, amanitin, camptothecin, bleomycim, carboplatinums, cytarabine, 5-fluoruracil, tamoxifen, calicheimycin, maytansine, tubylysin, etoposide, duocarmycin derivatives such as CC-1065, analogs, duocarmycin and esperamicin, a folate, pyrrolobenodiazepine and an RGD linked moiety.

In an embodiment, the payload compound is selected from the group consisting of radio-labels, molecular imaging agents, optical probes, nucleotides, oligosaccharides, and polymers.

In an embodiment, the forming of one or more covalent bonds between the first orthogonally-reactive moiety and the second orthogonally-reactive moiety occurs at physiological temperature and pH.

In an embodiment, the physiological temperature is 10-45° C., and the physiological pH is 5-9.

In another aspect, provided herein is a method for identifying a site-selective labeling compound, comprising;

providing a plurality of identical proteins, wherein each protein comprises two or more amino (—NH$_2$) groups;

contacting the plurality of proteins with a plurality of labeling compounds independently selected from the compound according to the present disclosure;

forming a covalent attachment between one or more nucleophilic groups of one or more proteins and the first orthogonally-reactive moiety of one or more compounds, to obtain one or more labeled proteins;

identifying the protein labeled with the highest selectivity; and identifying the corresponding site-selective labeling compound.

In an embodiment, the method further comprises identifying the protein labeled with the highest selectivity and in the highest yield.

In an embodiment, the site-selective labeling compound is identified using click chemistry reactions in conjunction with ELISA technology to monitor the extent of incorporation of the first orthogonally-reactive moiety in the target protein.

In an embodiment, the protein is an antibody. In an embodiment, the antibody is a therapeutic antibody useful for the treatment of cancer or autoimmune diseases.

In an embodiment, the nucleophilic groups are amino groups. In an embodiment, amino groups are located in the Fab region of the antibody.

In an embodiment, the labeling compound has an affinity for a conserved region of the protein.

In an embodiment, the affinity is represented by a Kd of 10 μM or less.

In another aspect, the present disclosure relates to a method for labeling an antibody, comprising:

(a) contacting the antibody with a compound of formula (XI):

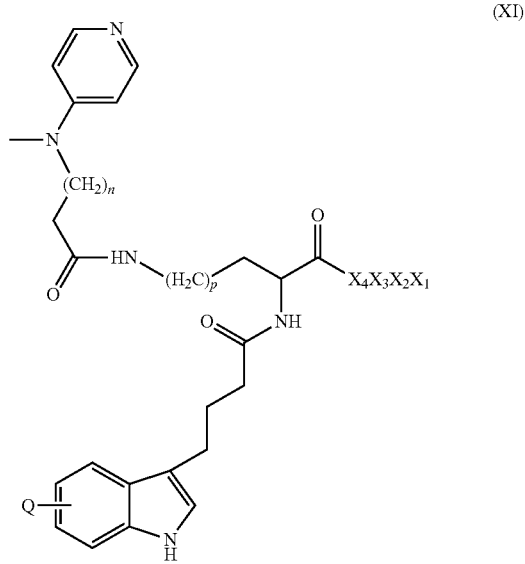

wherein $X_1$, $X_2$, $X_3$ and $X_4$ independently are residues selected from residues of natural amino acids and 2,3-diaminopropionic acid, thiotyrosine, 4-benzoylphenylalanine, 2-thiazole-alanine, norvaline, 1-naphthylalanine, 2-naphthylalanine, 3-naphthylalanine, N-ε-carbamyl-lysine, 2-thienylalanine, 3-aminopyrrolidine-4-carboxylic acid, 2',4'-phenylalanine, 2',5'-phenylalanine, 2',6'-phenylalanine, 3',4'-phenylalanine, or are absent, provided that at least one of $X_1$, $X_2$, $X_3$, and $X_4$ are present;

Q is H or an electron-withdrawing substituent (e.g., haloalkyl, —F, —NO$_2$ or —CN);

n=0-10; and
p=0-10; and
(b) contacting the product of step (a) with a compound of formula (XII), where independently, n=0-20; m=1-40.

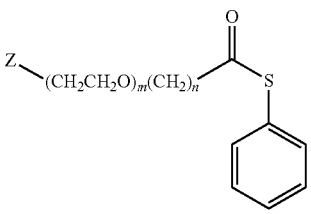

(XII)

wherein
Z is is a moiety selected from the group consisting of an alkyne, cycloalkyne, azide, 1,3-diene, nitrile oxide, nitrone, tetrazine, trans-cyclooctene, and carbonyl (e.g., aldehyde);
M is 1-40; and
n is 0-20.

In another aspect, the present disclosure relates to a method for site-selectively labeling the Fc fragment of an antibody, comprising:
contacting antibody with a compound of formula (XIII):

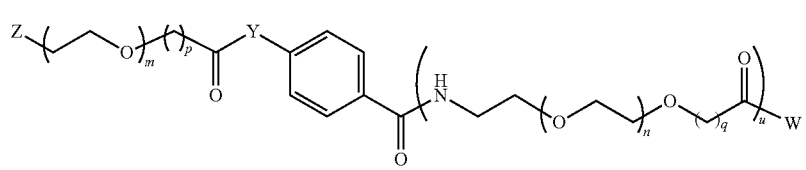

(XIII)

wherein

W = Asp-U-Ala-Trp-X-Leu-Gly-Glu-Leu-Val-Trp-U'-Thr

U and U' independently are cysteine, aspartate, glutamate, 2,3-diaminopropionic acid, lysine, or ornithine;
X is histidine, 3-(4-thiazolyl)-L-alanine, (R)- or (S)-2-amino-3-(thiazol-5-yl)propanoic acid);
Y=O, S or Se;
Z is alkynyl or cycloalkynyl, azido, formyl, acetyl, 1,3-diene, nitrile oxide, nitrone, trans-cyclooctene or tetrazine;
m=0-30;
n=1-20;
p=1-20;
q=1-2;
u=0-5;
the phenyl ring is optionally substituted with, F, $NO_2$, or CN; and
Y and the benzamide carbonyl may have an ortho, meta or para relationship.

In another aspect, the present disclosure relates to a method for site-selectively labeling the Fc fragment of an antibody, comprising:
contacting antibody with a compound of formula (XIV):

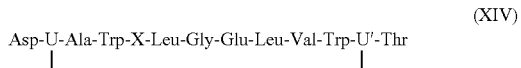

(XIV)

Asp-U-Ala-Trp-X-Leu-Gly-Glu-Leu-Val-Trp-U'-Thr wherein
U and U' independently are cysteine, aspartate, glutamate, 2,3-diaminopropionic acid, lysine, or ornithine;
X is

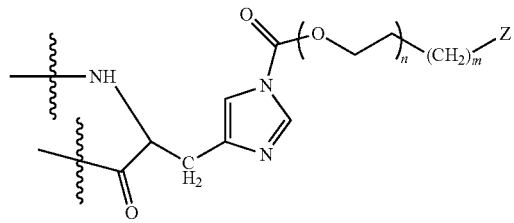

Z is alkynyl or cycloalkynyl, azido, formyl, acetyl, 1,3-diene, nitrile oxide, nitrone, trans-cyclooctene or tetrazine;
m is 0-15; and
n is 1-25.

In another aspect, the present disclosure relates to a method for site-selectively labeling the Fc fragment of an antibody, comprising:
contacting antibody with a compound of formula (XV):

(XV)

Asp-U-Ala-Trp-X-Leu-Gly-Glu-Leu-Val-Trp-U'-Thr wherein
U and U' independently are cysteine, aspartate, glutamate, 2,3-diaminopropionic acid, lysine, or ornithine;
X is

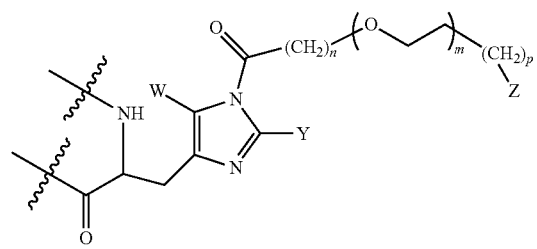

W is H and Y is F; or
W is F and Y is H;
m is 0-15;

n is 1-25; and p is 0-1.

In another aspect, the present disclosure relates to a method for site-selectively labeling the Fc fragment of an antibody, comprising:

to contacting antibody with a compound of formula (XVI):

$$\text{(XVI)}$$

LPro-Asp-U-Ala-Trp-X-Leu-Gly-Glu-Leu-Val-Trp-U'-Thr-DPro wherein

U and U' independently are cysteine, aspartate, glutamate, 2,3-diaminopropionic acid, 2,4-diaminobutyric acid, lysine, or ornithine;

X is

[chemical structure]

Y=O, S or Se;

Z is alkynyl or cycloalkynyl, azido, formyl, acetyl, 1,3-diene, nitrile oxide, nitrone, trans-cyclooctene or tetrazine;

m=0-30;

n=1-20;

p=1-20;

the phenyl ring is optionally substituted with, F, $NO_2$, or CN; and Y and the benzamide carbonyl may have an ortho, meta or para relationship.

In another aspect, provided herein is a compound of formula (V):

$$\text{(V)}$$

R—(CH$_2$CH$_2$O)$_m$(CH$_2$)$_n$—C(O)—NH-Lys-P wherein

P is a protein;

Lys is a lysine residue;

R is a moiety selected from the group consisting of an alkyne, cycloalkyne, azide, 1,3-diene, nitrile oxide, nitrone, tetrazine, trans-cyclooctene, and carbonyl (e.g., aldehyde); m is 0-40; and n is 1-20.

In an embodiment, P is an antibody.

In another aspect embodiment, provided herein is a compound of formula (VI):

$$\text{(VI)}$$

G—(CH$_2$CH$_2$O)$_m$(CH$_2$)$_n$—C(O)—NH-Lys-P wherein

P is a protein;

Lys is a lysine residue;

G is a moiety comprising a payload compound;

m is 0-40; and n is 1-20.

In an embodiment, G further comprises a triazole moiety.

In another aspect, provided herein is a pharmaceutical composition comprising the compound of formula (V) and a pharmaceutically acceptable carrier or excipient.

In another aspect, provided herein is a method of treating cancer in a patient, comprising administering to a patient in need thereof an effective amount of a compound of formula (VI).

BRIEF DESCRIPTION OF THE DRAWINGS

FIG. 2 depicts kinetic labeling libraries that match reactive molecules to complementary protein sites.

FIG. 3 depicts the composition of an optionally substituted kinetic labeling library member containing (thio)phenolic ester reactive functionality.

FIG. 4 depicts the composition of an optionally substituted kinetic labeling library member with reactive functionality as part of linear chains.

FIG. 5 depicts the composition of an optionally substituted kinetic labeling library member with benzoyl linkers attached to side-chain containing amino groups (e.g., lysine amino groups).

FIG. 15 depicts exemplary click copper-promoted reaction of an azide-containing payload with an alkyne-containing peptide auxiliary. (The inverse click reaction of alkyne-containing payload with an azide-containing peptide auxiliary leads to different regioisomers of the triazole product.) The analogous reactions of a cycloalkyne are "copperless" and can be conducted at ambient temperatures.

DETAILED DESCRIPTION

Figure 1:
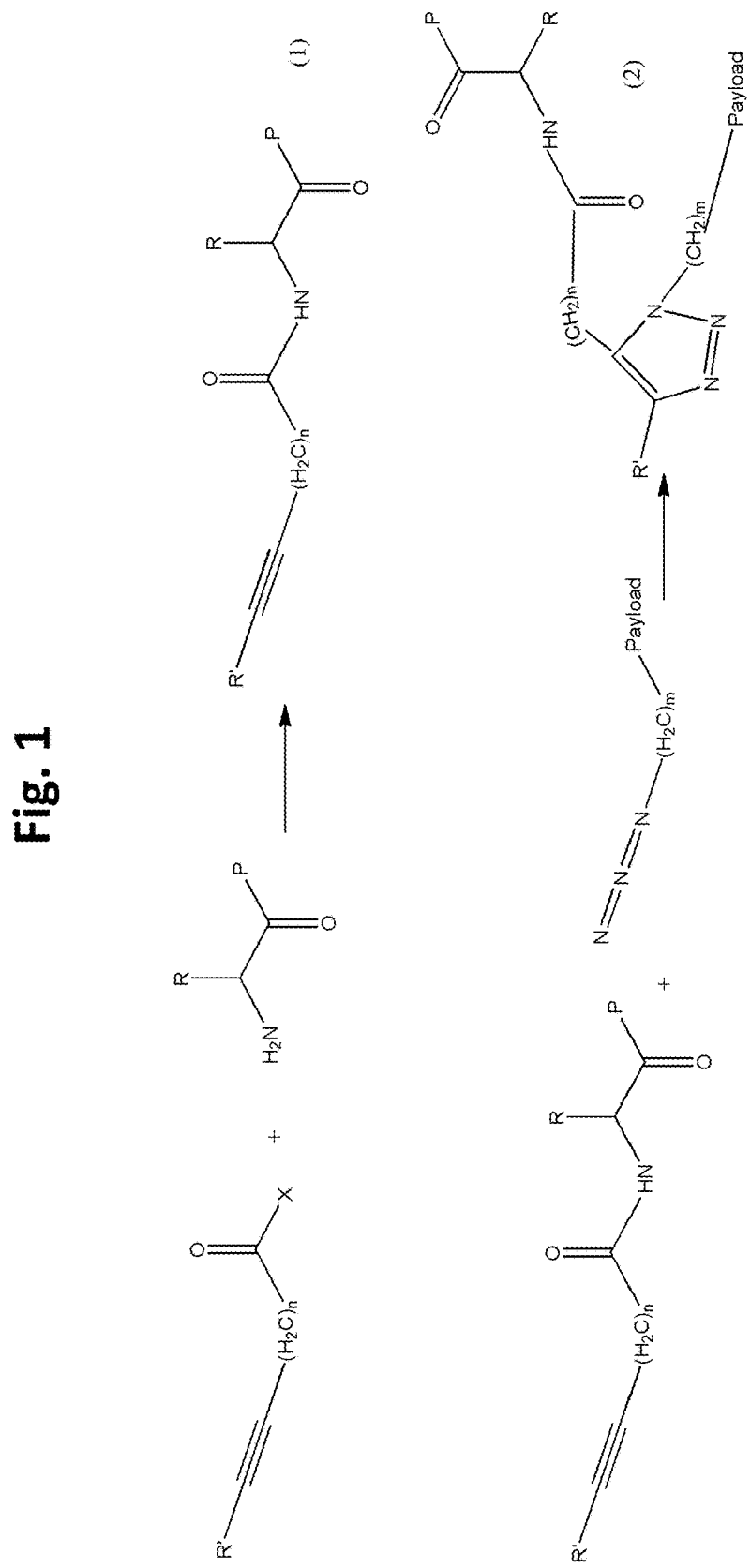
FIG. 1 depicts a two-step sequence exploiting orthogonally reactive entities, exemplified by acetylene and azide, for the crosslinking of payloads to proteins. The first step involves the identification from library screens of a molecule that site-selectively transfers an ORE-containing moiety to the amino group of a target protein. In step two, a payload of interest is crosslinked to the protein by a cycloaddition reaction.
Figure 6:
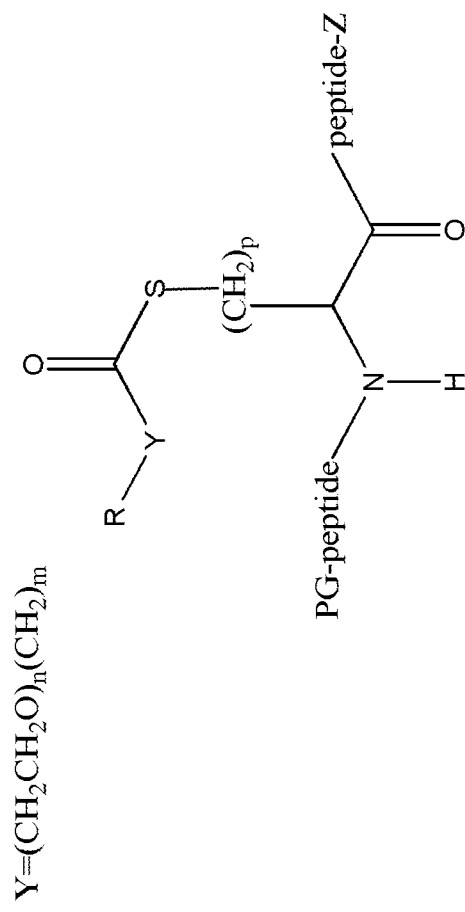
FIG. 6 depicts the composition of an optionally substituted kinetic library member with reactive acyl functionality linked to thiol groups.
Figure 7:
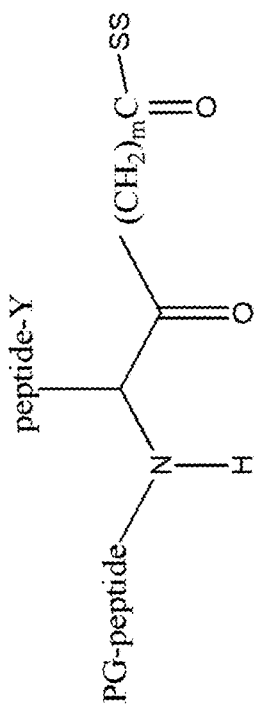
FIG. 7 depicts the composition of an intermediate in the synthesis of a kinetic labeling library subject to release from a solid support by attack at its C-terminal side-chain.
Figure 8:
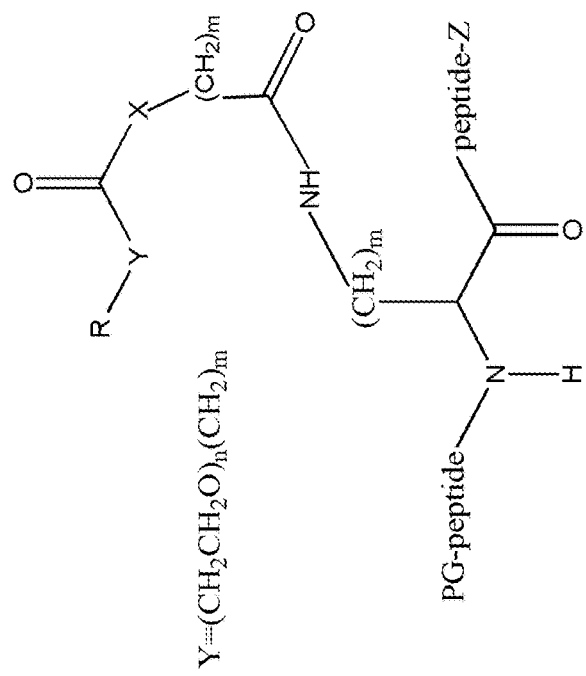
FIG. 8 depicts the composition of an optionally substituted kinetic labeling library molecule with reactive functionality part of a linear chain linked to side-chain amino groups.

The term affinity label is used herein broadly to describe molecules that are composed of an affinity group linked to an entity that is potentially reactive with proteins or other macromolecules. The affinity group (naturally or fortuitously) possesses binding determinants primarily for a specific site on a protein or other macromolecule that enables selective labeling of a proximal group on the protein surface.

As used herein, the term "electrophilic moiety" refers to molecule that is attracted to electrons. Such electrophilic moieties are capable of reacting with nucleophiles, such as amino groups of proteins and peptides. Preferred embodiments of electrophilic moieties include —C(O)O—, —C(O)S—, —C(O)Se—, —$SO_2$O—, —$SO_2$S— and —$SO_2$Se—.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tent-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

The term antibody as used herein may refer to monoclonal and polyclonal antibodies, their fragments (e.g., Fab, F(ab')$_2$, scFv (single-chain variable), sdAb (single domain antibody)), bi-specific antibodies, diabodies), and the like.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems can be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term bioorthogonal chemistry refers to any chemical reaction that can occur inside of living systems without interfering with native biochemical processes and hence would not occur with biological molecules such as proteins under conditions of physiological temperatures and pH. The term orthogonal is used interchangeably herein with bioorthogonal in the context of reactivity. These terms are meant to indicate that (bio)orthogonally reactive entities are click chemistry-reactive, but inert to reactions with biochemicals.

The term chemoselectivity refers to the preferential reaction of a chemical reagent with one of two or more similar functional groups.

The term chemospecificity refers to a reaction in which only one of a number of similar functional groups is modified.

The term click chemistry is used as defined in *Click Chemistry: Diverse Chemical Function from a Few Good Reactions,* H. C. Kolb, M. G. Finn and K. B. Sharpless, *Angew. Chem. Int. Ed.,* 2001, 40, pp. 2004-2021 and includes alkynes, cycloalkynes such as cyclooctynes and cyclononynes e.g. bicyclo[6.1.0]non-4-yn-9-ylmethanol), trans-cyclooctene, nitrones, nitrile oxides, azides and the like.

The term conjugate refers to a chemical compound that has been formed by the joining of two or more entities.

The term conserved sequence refers to a base sequence in a DNA molecule (or an amino acid sequence in a protein) that has remained essentially unchanged, and so has been conserved, throughout evolution. Conserved sites (also referred to as consensus binding sites) are thus an evolutionary consequence of unchanged sequences or those with closely similar homology and thus generally have similar affinities.

The term cycloaddition refers to a pericyclic chemical reaction, in which two or more unsaturated molecules (or parts of the same molecule) combine with the formation of a cyclic adduct in which there is a net reduction of the bond multiplicity.

The term "fusion protein" includes a single molecular entity having at least two polypeptide domains that are not normally present in a single, natural polypeptide. Thus, naturally occurring proteins are not "fusion proteins", as used herein.

The term "heteroaryl," as used herein, represents an aromatic (i.e., containing 4n+2 pi electrons within the ring system) mono-, bi-, or tricyclic-membered ring having between 5-14 ring members and containing one, two, three, or four heteroatoms independently selected from the group consisting of nitrogen, oxygen, and sulfur. Exemplary heteroaryls include, but are not limited to pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl (e.g., 1,3,4-thiadiazole), isothiazolyl, is isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

The term "hot spots" are amino acid residues of peptides contributing the most of binding free energy to peptide-protein interactions.

The term "2-oxacyl" or "α-oxacyl" is meant to indicate two carbonyls that are directly attached to each other, one being either an aldehyde carbonyl or a keto carbonyl.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term orthogonally reactive entity (ORE) or orthogonally reactive moiety is used (1) herein to distinguish its mutually exclusive chemical reactivity from the chemical reactivity of biological functionality under laboratory or physiological conditions, and (2) as it applies to click chemistry reactions to which biological polymers are inert. Preferred examples of orthogonally reactive entities include an alkyne, cycloalkyne, azide, 1,3-diene, nitrile oxide, nitrone, tetrazine, trans-cyclooctene, and carbonyl (e.g., aldehyde).

The term payload refers to any moiety that have potential commercial or medicinal value.

Examples of payloads include imaging moieties, antibodies, antibody fragments, proteins, optical agents, vitamins, enzymes, peptides, peptoids, toxins, drugs, prodrugs, ligands to a biomarker, stimulators of efferocytosis, compounds targeting a receptor selected from the group consisting of folate, EGFR, ALK, MET, PTK7 and KRAS or any oncogene product, anthracyclines, taxols, auristatins, amanitin, camptothecin, bleomycim, carboplatinums, cytarabine, 5-fluoruracil, tamoxifen, calicheimycin, maytansine, tubylysin, etoposide, duocarmycin derivatives such as CC-1065, duocarmycin and esperamicin, a folate, pyrrolobenodiazepine and an RGD linked moiety.

The term "peptoids" are defined as poly-N-substituted glycans that act as peptidomimetics and are resistant to preoteolysis.

The term "efferocytosis" refers to the process by which dying/dead cells are removed by phagocytosis. A "stimulator of efferocytosis" is any compound that promotes the process of efferocytosis. The term "subject" is intended to include organisms, e.g., prokaryotes and eukaryotes, which are capable of suffering from or afflicted with a disease, disorder or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, an autoimmune disease, arthritis, atherothrombosis, or plaque rupture. In another embodiment, the subject is a cell.

The term "peptide" includes chains of amino acids linked by peptide bonds. The term "peptide" can also refer to a "protein" or "polypeptide" (e.g., annexin proteins, granulocyte macrophage colony-stimulating factor, human superoxide dismutase, leptin, myoglobin, albumin, avidin, and an enzyme), which are compounds made of amino acids arranged in a linear chain and folded into a globular form. A variety of polypeptides or proteins may be used within the scope of the methods and compositions provided herein. In certain embodiments, the proteins may comprise antibodies or fragments of antibodies containing an is antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. In certain contexts the protein may represent any macromolecule containing amines or thiols. Accordingly, the term "protein or peptide" encompasses amino acid sequences comprising at least one of the common amino acids found in naturally occurring proteins, or at least one modified or unusual amino acid. Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The protein, polypeptide and peptide sequences can be found at computerized databases known to those of ordinary skill in the art. One such database is the National Center for Biotechnology Information's Genbank and GenPept databases. Alternatively, various commercial preparations of proteins, polypeptides, and peptides are known to those of skill in the art.

As used herein, "physiological pH" refers to a pH of 7-8, 7.2-7.6, 7.3-7.5 or 7.35-7.45. "Physiological temperature" refers to 36-38° C. or 36.5-37.5° C.

The term "pharmaceutical composition" as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "prevent," as used herein, refers to prophylactic treatment or treatment that prevents one or more symptoms or conditions of a disease, disorder, or conditions described herein. Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein, or a pharmaceutically acceptable salt or solvate thereof, or a pharmaceutical composition thereof, can be acute, short-term, or chronic. The doses administered may be varied during the course of preventative treatment.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Where a group is substituted, the group may be substituted with 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, halogen (—F, —Cl, —Br, or —I), azido(—$N_3$), nitro (—$NO_2$), cyano (—CN), acyloxy(-OC(=O)R'), acyl (—C(=O)R'), alkoxy (—OR'), amido (—NR'C(=O)R" or —C(=O)NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, aryl, or heteroaryl. In some embodiments, the substituent groups themselves may be further substituted with, for example, 1, 2, 3, 4, 5, or 6 substituents as defined herein. For example, a $C_{1-6}$ alkyl, phenyl, or heteroaryl group may be further substituted with 1, 2, 3, 4, 5, or 6 substituents as described herein.

The present invention includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otheise stated, all tautomeric forms of the compounds of the invention are within the scope of the invention.

The present invention includes all pharmaceutically acceptable isotopically-labeled compounds of the invention, wherein one or more atoms are replaced by atoms having the same atomic number, but an atomic mass or mass number different from the atomic mass or mass number usually found in nature. Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Salts derived from appropriate bases include alkali metal, alkaline earth metal, and ammonium salts. Representative alkali or alkaline earth metal salts include sodium, lithium, potassium, calcium, magnesium, and the like. One class of salts includes the pharmaceutically acceptable salts. The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P.H. Stahl and C.G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

As used herein, "site-specific" refers to a reaction or transformation (e.g., the acylation of a protein) wherein a single product (e.g., acylation of a particular basic residue of a protein) comprises about 100%, at least about 90%, or at least about 80% of all products formed.

As used herein, "site-selective" refers to a reaction or transformation (e.g., the acylation of a protein) wherein the most-abundant product (e.g., acylation of a particular basic residue of a protein) comprises at least about 70%, at least about 60%, at least about 50%, at least about 40%, at least about 30%, or at least about 20% of all products formed, and wherein the ratio of the most-abundant product to the next most-abundant product is in the range of about 1.1:1 to about 1000:1. In a particular embodiment, the ratio of the most-abundant product to the next most-abundant product is in the range of about 2:1 to 100:1. In another particular embodiment, the ratio of the most-abundant product to the next most-abundant product is about 10:1.

The terms traceless linkers and traceless affinity labels are used interchangeably herein to refer to reactions with proteins. Traceless linkers or traceless affinity labels are so called herein because an examination of the site-selectively conjugated product reveals no trace of binding determinants which facilitated the (linkage) reaction.

In accordance with the subject invention, compounds are screened for extent of incorporation of an ORE label into the protein target and identified for directing covalent bonding of a species containing an orthogonally reactive entity (ORE) to specific amino groups of a target molecule such as an antibody (*Click Chemistry: Diverse Chemical Function* from a Few Good Reactions, H. C. Kolb, M. G. Finn and K. B. Sharpless, *Angew. Chem. Int.* Ed., 2001, 40, pp. 2004-2021). This procedure can be done for pure compounds when some knowledge of binding determinants to target sites are known, or for libraries of molecules. The library members generally consist of a constant reactive group (linked to the label), a linker, which connects to a variable peptidyl group that constitutes a critical element of the affinity group. It is the variable affinity group that accounts for the variance in the data. The winning compounds react most rapidly and introduce labels onto the antibody framework containing ORE's, site-selectively. The winning compounds are tracked and "stand out" by virtue of (1) their possessing relatively faster rates of incorporation of the label compared to labeling rates of a standard molecule lacking an affinity group, or (2) comparisons against other individual members like their enantiomers, or the aggregate rate of incorporation of pools of library members. Discovery of such chemoselective labeling agents ensures that a second, essentially quantitative reaction will be chemoselective, which involves crosslinking payloads to protein (antibody) targets through the union of OREs (as shown for an exemplary acetylene-azide reactive pair in FIG. 1). This second step exploits orthogonally reactive components which are inert to biologics and are click chemistry-reactive. The net result of this chemospecific two-step sequence is to produce materials that to possess a high degree of homogeneity, and provide access to commercially and medically valuable products, such as antibody-drug conjugates. Since there is an appreciation by the inventors that library members and "innovatively reformatted ligands" that are targeted for conserved sites on antibodies may be especially useful and possess high commercial value, an additional feature of this invention involves a "universal" antibody linker capable of being installed on an analogous conserved site of different antibodies. The formation of this ORE-linked antibody is tantamount to having an "off the shelf" affinity label that mediates the site-selective labeling of virtually any (IgG1) antibody. The ORE antibody can then be transformed in a second step, with an appropriately modified payload, to the desired ADC. Thus, the compounds and methods of this invention find particular utility in simplifying, improving, and standardizing a process by which payloads and proteins are crosslinked site-selectively and site-specifically.

From a library perspective, the method in the first stage (FIG. 2) consists of treating a protein, or other molecule, containing several amino groups, with ensembles of molecules that compete for attachment to amino groups on the protein surface. The winning molecules are those that most rapidly transfer the ORE-containing group Y to the protein, hence, the designation: kinetic labeling libraries.

The emphasis on rate of covalent labeling as a determinant of site-specific (or site-selective) labeling underlies the design of screening protocols. It is based on the intimate relationships between complementarity, rate, and specificity, drawn from enzymology. The expectation is that library members, by virtue of complementary interactions with specific protein sites, will have the greatest binding affinities or fast on-rates for those sites, and will react most rapidly and specifically with proximal amino groups at such sites, rather than at sites of much lower affinity or which are less accessible kinetically. In essence, covalent bonding is facilitated by pre-association (by converting an intermolecular rate into an intramolecular rate), which provides an entropic advantage, analogous to an enzyme reaction (Cf Jencks, W. P. Catalysis in *Chemistry and Enzymology;* McGraw-Hill: New York, 1969; Fersht, A. R. *Enzyme Structure and Mechanism,* 2nd ed.; Freeman, New York.)

In FIG. 2, the protein is depicted schematically as containing a series of sites, each of which possesses structure in the form of geometrical shapes. Members of a kinetic labeling library are portrayed as tripartite agents comprising a variable structural element (shown as a geometric shape), a cross-linker X, and a moiety Y that is transferred to the protein. The bond between X and Y essentially defines the baseline reactivity of the tripartite agent. The expectation is that based on the "goodness of fit" of the variable structural element, and the to action of a proximal reactive group of the protein, rates of covalent labeling will be accelerated over the same type of reactive group unassisted by comparable binding affinity or complementarity.

The expectation for a library in which each member contains the same reactive group, is that rate variances would be primarily a consequence of the variable structural element. In any event, rate variances of competing systems or molecules that are significantly larger than a standard lacking a complementary group or the average rate of competing entities (e.g., pools), are likely to signal site-specific reactions.

For the tripartite agent, represented as W-X-Y (as defined above) both X and Y are constant in every agent, and W represents a variable structural element. Hence, all of the variance in the data should be attributable to the impact of W, which contains chiral elements. Thus the goal is to choose structural motifs for W that can be systematically modified to profoundly influence labeling rates and specificities. Since W is liberated as part of the leaving group during the labeling process, the temptation is to maximize its size and complexity to achieve the tightest binding and fastest labeling rates. However, the size of W, in initial screens, will be dictated primarily by synthetic protocols designed to keep the number of library members in pools to practical limits, binding data of known ligands that can be incorporated into the affinity element, labor intensive demands of screening, and expectations of the magnitude of variances that can be exploited in further rounds of screening.

The size and nature of Y is a key feature of this invention. Screening of libraries wherein Y is, or carries, a payload, has been invoked and has several severe limitations. The chemical compatibility of drug moieties (which are often nucleophilic) with reactive X-Y functionality, is one issue. Of particular importance in payload-bearing libraries is the size and complexity of Y, which will necessitate unique Y entities for unique payloads and thus unique libraries for each protein target are required. A more subtle point is that the size and complexity of Y often dominates and vitiates the effects of the variable structural element. Indeed, the more complex the structure of Y, the more likely the accommodation of Y may be a critical factor that also varies with the structure of W. This may be especially true when W is relatively small. Indeed, studies of protein labeling, for a given W, show that structural features in Y are a critical determinant of site-specific labeling for peptide-based libraries. Thus, in library design it is important to consider the gross structural features of W in relation to that of Y, so that Y as a variable structural element can be the critical determinant of site-selectivity and specificity.

In this invention, a priori, there is the appreciation by the inventors that it is particularly advantageous to employ Y entities of modest size that are (1) likely to be easily accommodated by the antibody target, are (2) unlikely to perturb the intrinsic reactivity of the tripartite agent and (3)

unlikely to perturb the potential selectivity imparted by the group W, whose size should be optimized in any event. This invention is further informed by our observation that if only peptide functionality is utilized in the affinity group, with the majority of proteins there appears to be a practical threshold peptide length (vide infra) to achieve the requisite affinity labeling leading to "hits" at non-endogenous ligand binding sites. This is not surprising, since tight-binding, even at endogenous ligand binding sites, has proven to be a rare event among structurally diverse competing entities. Thus, the success of site-specific labeling using kinetic labeling libraries hinges on the use of variable structural elements with "critical mass binding determinants" to elicit specific interactions with the target protein, balanced against the size of Y. Therefore, to introduce diverse payloads onto a protein target, site-specifically, a two-step process, in which the first step is optimized and standardized to accept virtually any payload, is a far superior alternative to any prior art involving library screens.

To the extent that peptide functionality can be combined with other known affinity elements to augment binding beyond a threshold value, the size of Y can be of minor consequence. This strategy can be adopted for libraries targeted to specific sites ("targeted kinetic libraries) when information on binding to such sites is available.

In light of the above challenges in accommodating payloads in single step labeling scenarios, the subject of this invention is preferentially concerned with the first stage, namely methods for site-selectively labeling proteins with OREs. The second stage, involving click chemistry of the desired payload, follows established precedents. Since OREs are of modest size, are easily accommodated by proteins, and are unreactive with biological functionality such as peptide bonds, a general method is at hand for the crosslinking of diverse payloads to proteins through the agency of ORE-labeled protein conjugates. ORE's thus serve a dual function by facilitating both the first and second stages leading to crosslinked product.

Previously, library screening of human serum albumin with a kinetic labeling library consisting of a pentapeptidyl variable structural element as the affinity group resulted in site-specific labeling of the protein. In this instance, since HSA is known to bind numerous carboxylate-containing molecules, the successful outcome may have been a consequence of incorporating a glutamate at the C-terminal as a constant feature of the library, as well as the promiscuous nature of HSA as a binder of numerous ligands. Most proteins are known to tightly bind only a few ligands from random libraries. Our experience has been that the peptidyl affinity group of kinetic labeling library members should generally possess greater than five amino acids in linear array to achieve distinct "hits" at sites that are not known to bind endogenous ligands. Such peptidyl units are needed to provide sufficient variance in the data so as to facilitate the discovery of site-specific labelers of protein targets by combinatorial libraries. To the extent that non-peptidyl affinity elements to the target protein are known they may be combined with the variable peptidyl functionality to augment binding, and modulate the size of the peptidyl component to achieve appropriate rate-enhancements. In the latter instance, targeted libraries can be constructed.

For targeting established ligand binding sites, precedents from high throughput screening of synthetic combinatorial libraries show that a hexapeptide length is sufficient to achieve a number of "hits" for the discovery of tight binding ligands. Studies on beads using combinatorial peptide libraries have shown that capture of proteins of select proteomes can also be accomplished with hexapeptides Indeed, peptides containing from 6-10 amino acids are preferred components of our kinetic labeling libraries.

However, it is expedient to limit the size of the kinetic labeling library for practical screening purposes. For example, pooling protocols with ten distinct amino acids randomized among six positions would give rise to a million library members and require the pooling of far too numerous, potentially reactive molecules. Such a prospect raises concerns of inadequate mixing during short reaction times, solubility issues, and competition from secondary and/or multimeric reactions.

To limit the size of the library we have invented libraries based on the following premises (adapted from London et al.; Birtalan et al.). That at least two hot spots are required for productive binding of affinity labels and therefore linear peptides of at least 6-8 amino acids are necessary. Further, peptide hotspot residues are preferably located in the peptide center and not over-represented in N- or C-terminal regions. Aromatic amino acids such as well as leucine and isoleucine are preferred as hotspot residues. London N, Movshovitz-Attias D, Schueler-Furman O The structural basis of peptide-protein binding strategies. Structure 2010 Feb. 10; 18(2):188-99; Birtalan S, Zhang Y, Fellouse F A, Shao L, Schaefer G, Sidhu S S. The intrinsic contributions of tyrosine, serine, glycine and arginine to the affinity and specificity of antibodies. J Mol Biol. 2008 Apr. 11; 377(5):1518-28.

In the first stage, the OREs are expected to be a limited perturbation on the intrinsic reactivity of library members with 6-8 amino acids and provide a handle for detection and assay. Their modest size and structural simplicity are major assets in avoiding competition with variable structural elements for accommodation on the protein surface that would render interpretation of rate data inconsistent and confusing. As a constant feature of the tripartite agent, the assumption that the species Y will behave similarly in each agent's interactions with protein, is more likely for small Ys of minimal structural complexity, especially in combination with short peptide lengths.

In the second stage OREs provide a specific point of attack for the introduction of payloads that are likely to be high yield reactions leading to homogeneous product. Literature precedents of conjugating payloads to proteins emphatically support this scenario.

In prior art, payload entities have been presented as part of an agent containing reactive functionality that transfers the payload to the molecular target in "one fell swoop". In the present invention the incorporation of the orthogonally reactive entity within the target protein, as a prelude to introducing the payload in a second step, represents a considerable advantage and superior alternative to prior art.

First, synthesis is simplified as many OREs are quite easily incorporated in the tripartite agent by diverse synthetic methods. For OREs, a single synthetic motif can be employed, adaptable to most contingencies. Depending upon the payloads employed, synthetic methods would have to be individually tailored for the construction of the tripartite agent in payload-bearing libraries.

Secondly, the use of OREs enables the construction of universal screening libraries, e.g., libraries that can be employed against any protein target, in which amino acids are randomized among a number of peptide positions to obtain highly diverse libraries. This feature is highly advantageous for building a structure-reactivity database that will increase understanding of protein reactivity and optimize strategies for generating "hits".

Thirdly, screening of library members, each of which contain a payload, is far more expensive than using ORE's to discover the best labelers, as drugs, polymers and imaging agents and the like, are generally quite costly.

Fourthly, the use of ORE's introduces an element that can facilitate screens, as methods exist for the generation of optical probes from ORE's. Such optical probes provide a basis for detection of site-specific labeled entities (*Fluorogenic click reaction.* Le Droumaguet C, Wang C, Wang Q. *Chem Soc Rev.* 2010 39(4):1233-9).

Fifthly, screening library members with attached payloads represents a considerable challenge as the payload must be accommodated throughout the overall conjugative process to and could vitiate the specific effects of the peptide moiety (variable element) and its potential chemospecificity. ORE's, among which are alkynes and azides, are among the smallest functional groups and are unlikely to introduce significant perturbations on the intrinsic reactivities and specificities of affinity groups.

The latter has been a major issue in the design of the tripartite agent, since the size of is the variable peptidyl moiety is very often dictated by the demands of screening, and may be restricted to 4 or 5 residues in the first round. In these circumstances, the size and complexity of the attached payload is likely to abrogate the intrinsic binding specificities of peptidyl moieties which underlie the site-specific labeling process. This potential perturbation on the labeling process, also imposes serious limitations on "bait and switch" strategies in which library screening is first done with simple structural entities that are transferred to the protein target, and then replaced by more structurally complex payloads upon identification of successful "hits".

In summary, ORE-bearing libraries represent a superior motif to payload-bearing libraries as the former permit standardization of the labeling process, comprise a reactive entity for (near) quantitative attachment of payloads to proteins, and are less likely to interfere with intrinsic binding and labeling patterns of activated peptidyl groups, W.

Universal Libraries

Screens of binding combinatorial libraries, which depend only on affinities between components at equilibrium, provide tight binding molecules to specific sites as a rare event. Invariably, further rounds of screening are required for optimizing affinity. The expectation is that screens of bonding libraries would uncover fast labeling library members as rare events as well, given that both tight binding of the tripartite agent and capture of a proximal reactive protein amino group are required for site-specific labeling.

Screening formats for potentially reactive libraries are also expected to be more limited than for binding libraries. The size of pools is limited by both labor-intense screening manipulations, and the potential reactivity and kinetic behavior of the kinetic labeling library members; indeed, increasing numbers of library members introduce increasing levels of complexity. Thus, detailed structural information could be invaluable in guiding experimental design and the selection of successful structural motifs. It is to be noted however, that despite the existence of numerous crystal structures of proteins, examples of designer affinity labels emerging from computer modeling studies are lacking.

More often than not, detailed structural information is not available for streamlining library design motifs. For this eventuality, the design of a "universal library" that can furnish matches of selective labelers to specific amino groups of any protein is formulated. In practice, this goal is likely to be difficult to achieve for any one library, as even the discovery of a single selective labeler of a single specific amino group is expected to be a rare event.

A priori, an ideal library would contain a series of W entities with sufficient structural diversity to provide some "hits" exhibiting, at the least, site-selective labeling. The initial parent library need not yield site-specific labelers as subsequent rounds of screening, building on the "hit's" structure, will improve site-selectivity. X-Y on the other hand will have to balance its ability to carve out a sufficient spatial volume so as to optimize the trapping of amines in, or close to, the binding site. For maximum effect, it is essential that the chiral moiety W, be "felt" by the protein. For protein targets where structural data is lacking and models are speculative, constructing a single universal library, e.g., a library of general utility, can be challenging.

Consequently, it is advantageous to have a series of libraries that are likely to cover various contingencies. The libraries of composition I-V (FIGS. 3-8) illustrated for active esters, collectively cover a range of properties designed to facilitate labeling rates by the tripartite agent and to bring the variable structural element (e.g., peptidyl group) into contact with the protein. Libraries in which the reactive ester function is deployed at the N-terminus, or is attached to a residue at an interior position of the chain are both represented. Libraries in which the reactive ester function is an aryl ester or an alkyl ester are also both represented. The reactivity of the former can be modulated by ring substitutions firmly established in the art; whereas the non-aryl ester can be activated by substituent effects such as polyhaloalkyl, oxyalkylene, propargyl and the like.

The compounds of this invention employing "universal libraries" also find particular use in covalently bonding an orthogonally reactive entity to a specific amino or thiol of a target molecule in the presence of a plurality of chemically reactive competitive sites on other molecules, so as to reduce the amount of non-random bonding in the mixture. Normally, the enhancement will be at least about a factor of 1.5 over totally random bonding as determined comparison to that bonding which occurs with a compound that exhibits no increased specificity for any particular target molecule or site over any other target molecule or site, more usually at least about a factor of 2, preferably by a factor of 5, and more preferably by a factor of 10. Although bonding may be specifically directed toward a particular target molecule in a mixture, rarely would one anticipate that bonding would be solely to the target molecule(s) without additional rounds of screening, in order to optimize the affinity of a variable element, such as a peptide moiety.

Figure 9:
FIG. 9 depicts thiolactones as key intermediates for the addition of homologous alkylthiol linkers.

The compounds to be screened will often have the following formulae: Y-SPhZ-W where Y contains an orthogonally reactive group linked to an acyl function preferentially, by one or more carbons or alkylene oxide entities, SPhZ is frequently an m- or p-thio-benzoyl or thio-tyrosyl group or their phenolic analogs, and W is a moiety which typically includes at least one amino acid. Libraries containing alkyl thioesters and the like as reactive groups can be prepared by SPPS using cyclic thioesters to introduce the linker portion X into tripartite agent precursors as in FIG. 9.

The corresponding carboxylic esters analogs of the thioesters are also available through standard chemistry known in the art, executed by a trained organic chemist of ordinary skill.

For the most part, moiety W will be a variable element that is oligomeric and, therefore, various groups which can be readily and systematically varied are useful including, for example, oligopeptides, oligonucleotides, oligosaccharides, combinations thereof, or the like. Generally, the variable element represented in any particular library will be of a common type. Oligomeric variable elements are readily synthesized as a combinatorial library, so that the synthetic chemistry is substantially repetitive with the addition of each monomer unit to the growing oligomer. Also, mass spectrometry methods are available for analyzing the composition and/or sequence of the oligomeric variable element. Alternatively, the variable element may comprise small synthetic organic molecules having a molecular weight of at least about 200, and not more than about 5,000, generally ranging from about 250 to 2,000.

Generally, the oligomers employed will have at least 3 monomeric units, more usually at least 4 monomeric units, and usually fewer than 20 monomeric units, more usually fewer than 12 monomeric units, preferably fewer than 10 monomeric units and more preferably in the range of about 6-10 monomeric units. With regard to the variable elements represented in the library, one or more monomeric units of the oligomer may remain constant, thereby providing a mechanism for reducing the overall complexity of the combinatorial library. The most preferred number of variable elements is 4-5. The monomer units comprising the oligomeric variable element may be naturally occurring or synthetic, generally being from about 2 to 30 carbon atoms, usually from about 2 to 18 carbon atoms and preferably from about 2 to 12 carbon atoms.

If the variable element is an oligopeptide, the amino acid monomers may be naturally occurring or synthetic. Conveniently, the naturally occurring L-.alpha.-amino acids will be used, although the D-enantiomers may also be employed.

While the amino acid monomers of the oligomer may be any one of the 20 naturally occurring amino acids in either the L- or D-configuration, the amino acids employed will preferentially be free of reactive functionalities, particularly reactive functionalities which would react with the reactive functionality of the variable element. Therefore, the amino acids which are used will usually be free of reactive amino and thiol groups as well as histidine. Of particular interest are such amino acids as alanine (A), glycine (G), proline (P), valine (V), serine (S), phenylalanine (F), isoleucine (I) and leucine (L) or uncharged polar amino acids like asparagine (N), glutamine (Q) and methionine (M), other aromatic amino acids such as tryptophan (W), and tyrosine (Y), or charged polar amino acids such as arginine (R), glutamate (E), and aspartate (D).

The amino acid monomers of the oligomeric variable group may also be synthetic: unnatural or substituted amino acids of from 4 to 30, usually from 4 to 20, carbon. Aromatic amino acids such as phenylalanine (Phe), tyrosine (Tyr), and tryptophan (Trp) are of special interest and are preferred at the internal positions of the peptide. Of particular interest are the synthetic amino acids .beta.-alanine and .gamma -aminobutyrate or functional group protected amino acids such as O-methyl-substituted threonine (T), serine (S), tyrosine (Y), or the like.

Synthetic amino acids may be monosubstituted on nitrogen as in peptoids, which are oligomers of N-substituted glycine residues. N-substituted amino acids which find use will have an N-substituent of from about 1 to 8, usually 1 to 6 carbon atoms, which may be aliphatic, alicyclic, aromatic or heterocyclic, usually having not more than about 3 heteroatoms, which may include amino, either tertiary or quaternary, oxy, thio, and the like.

Oligopeptides may be constructed by employing standard Merrifield solid phase synthetic methods, manually or by using an automated peptide synthesizer, standard protection chemistry (e.g., t-Boc or Fmoc chemistry) and resins (e.g., 4-methyl benzhydryl amine Rink Amide resin). Successive rounds of deprotection of the terminal amino group and coupling of amino acid monomers, followed by deprotection and cleavage of peptides from resins results in the synthesis of oligopeptides of the desired sequence and length. Additionally, liquid phase peptide synthesis is well known in the art and may also be employed.

If the amino acid monomers employed are N-substituted glycine residues, monomers may incorporate t-butyl-based side chain and 9-fluorenylmethoxycarbonyl .alpha -amine protection. (See, for example, Gordon et al., J. of Medicinal Chemistry (1994) 37, 1387-1385, and references cited therein). Controlled oligomerization of the N-substituted monomers may be performed manually and/or robotically with in situ activation by either benzotriazol-1-yloxytris (pyrrolidino)-phosphonium hexafluorophosphate or bromotris (pyrrolidino) phosphonium hexafluorophosphate. Additional steps may follow standard automated peptide synthesis protocols using .alpha.-(9-fluorenylmethoxycarbonyl)amino acids.

If the variable element includes an oligonucleotide, either naturally occurring or synthetic nucleotide monomers may be employed. Particularly, for synthetic nucleotides, the phosphate or sugar groups may be modified where phosphate may be substituted by having the oxygen atoms replaced with sulfur or nitrogen, the phosphate group may be replaced with sulfonate, amide etc., the ribose or deoxyribose may be replaced with 5 to 6 carbon atom sugars such as arabinose, fructose, glucose, or the like, and the purines and pyrimidines may be modified by substitution on nitrogen, with alkyl or acyl, may employ different ring structures, may have nitrogen replaced by oxygen, or vice versa, and the like.

If the variable element includes an oligosaccharide, the oligosaccharide will usually have from 2 to 6 monomeric units which may be linear or branched, comprised of sugars of from 5 to 8 carbon atoms. Various modifications of known oligosaccharides may be employed, particularly where one is interested in binding to lectins or adhesion molecules.

Combinatorial libraries of variable elements may be prepared in accordance with conventional ways for producing combinatorial libraries, particularly using a solid support and adding the monomeric components in a stepwise manner See, for example, U.S. Pat. Nos. 4,883,092; 5,010,175; 5,182,366 and 5,270,170 and PCT application Nos. WO 92/00091; WO 92/09300; WO 93/06121; WO 93/20242; WO 94/06451; WO 94/06291 and WO 95/28640, as exemplary of a much larger literature of techniques. Preferably, the synthetic chemistry is substantially repetitive with the addition of each monomer unit to the growing oligomer.

Initially, combinatorial libraries of compounds having a collection of variable elements are to be screened for the speed with which they covalently label amino groups of the target protein. (For purposes of exposition this discussion will be focused on amino groups, but entirely analogous considerations apply to libraries targeted for thiol groups using for example, tosylate-based libraries.) The variable core structural element for purposes of discussion will be peptidyl although numerous motifs are envisioned by the inventor. Generally, the library will have compounds representing at least 50 different peptidyl groups, frequently 100 different peptidyl groups, usually at least about 500 different peptidyl groups, preferably at least about 1000 different peptidyl groups, and maybe 10,000 or more different peptidyl groups, although the number of compounds in the library will depend on the method of screening. The library may have greater proportions of one compound over other compounds, but desirably the relative concentrations will differ by less than about 50%, preferably less than about 25%. For the screening process, the libraries may be divided into smaller units, which will generally range from about 5 to 1,000, frequently from about 5 to 500, usually from about 10 to 500 moieties and more usually from about 10 to 100. The source of the peptidyl groups may be any convenient source including combinatorial libraries, natural products, stored synthetic compounds, and the like.

Figure 10:
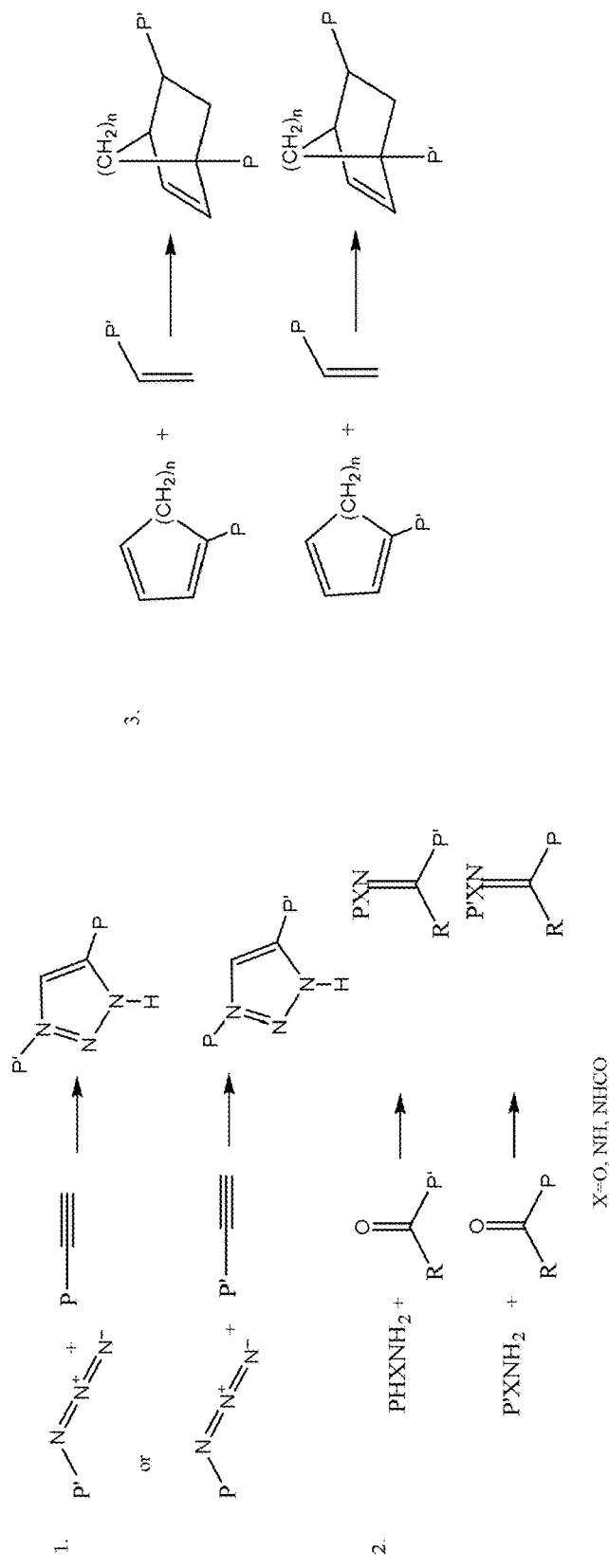
FIG. 10 depicts exemplary orthogonal reactive entities and their reactions (P=protein; P'=payloads).

For both targeted and universal KLL, orthogonally reactive entities (OREs) known in the art constitute the prime elements to be transferred in step (1) of the two step labeling sequence. Alkynes and azides are examples of orthogonal reactive entities which find application for linkage to protein targets. Alkynes are inert to biological functionality and require copper species to promote adduct formation with azides, however, strained cycloalkynes react rapidly and specifically with azide functionality. Thus, payloads containing azide groups can be irreversibly bound to proteins containing cycloalkynes to produce stable triazole products. As well, payloads containing cycloalkyne groups can be irreversibly bound to proteins containing azides to produce stable triazole products. Numerous precedents exist for irreversibly and specifically attaching structural elements onto the framework of biological molecules by exploiting pairs of ORE reaction partners. ORE's are such that they do not naturally occur in proteins and need to be introduced synthetically. They perform the desired function of efficiently reacting specifically with their partner in click chemistry by virtue of their lack of reactivity with biochemical functionality at physiological temperatures and pH. Some combinations known in the art that can be deployed to crosslink payloads to proteins are shown in FIG. 10.

Alkynes (cycloalkynes) and azide functionality, as well as tetrazine and trans-cyclooctene pairs, are particularly good choices for crosslinking payloads to proteins in that they are inert to a wide variety of chemical functionality under a wide range of conditions where it is practical to perform manipulations on proteins. Thus, the nature of the payload to be carried by the protein may be varied widely, depending upon its purpose. In one application, the payload may serve as a physiologically active compound, where the purpose of the subject compound is to bond the physiologically active compound to a long lived blood component. The protocol for bonding payloads to proteins is dependent in the first instance upon the affinity of the tripartite agent which serves to enhance the amount of the ORE that becomes bound to a particular target site. This first step involves the transfer of ORE specifically to a single, specific amino group. The second step can be restricted to only a single "click chemistry" option, e.g., cycloaddition of alkyne and azide components carried by separate molecules.

A decision as to what labeling group might be most useful can be based on the potential for successfully condensing a variety of payloads onto the label in an essentially quantitative secondary reaction to produce the desired products. Of the entities currently in use: simple acetylenes, cycloalkynes, etc., the use of azides would appear to be a judicious choice for several reasons, including its small size and ultimate utility in click chemistry reactions with cyclooctynes, which are rapid reactions that are easy to carry out.

In fact the azide group provides a convenient handle for both synthetic, analytical. and separation technology. For example biotin-dibenzcycloooctyne reagents can be used to biotinylate the azide-tagged protein. This quantitative reaction provides a means of exploiting avidin-biotin technology in an ELISA and/or alkaline phosphatase methodology, to determine the extent to which azide functionality has been incorporated within samples containing the protein target. Alternatively, for analytical purposes, a variety of optical probes derivatized with cycloalkynes (e.g., fluorescent, NIR) can be employed to quantitate by titration the extent of incorporation of azide into macromoleceules. If the library screening is conducted using split pools, after the most reactive pools have been identified, they can then be treated with cyclooctynes on solid supports to separate the azide-labeled species from unreactive protein and the azide-labeled peptide can then be released form the solid support, its structure determined, and related back to the reactive peptide species.

For the most part, the utility of these agents will be manifested in the context of ex vivo applications. In favorable instances the reaction can be used in tandem, in vivo. For example, an ORE-bearing affinity label discovered from library screening can be combined with a complex mixture, such as blood, cells, tissue, or the like, and home in on its high affinity target to which it becomes attached. These subject compounds may be administered in a first step in vivo as described in U.S. Pat. No. 5,612,034. When used with blood, the primary targets will be immunoglobulins, red blood cells, particularly glycophorin proteins of the red blood cells, serum albumin, and platelets, however, other target sites are available. In a second step the ORE-labeled blood component is chased with its complementary partner to give the ultimate crosslinked product.

In other applications, the protein modified by an ORE-bearing affinity label discovered from library screening, may be combined with a payload bearing a corresponding ORE.

The payload may be a compound which allows the diagnostic visualization of specific sites or compartments within the body by employing such diagnostic techniques as positron emission tomography (PET), computerized tomography (CT), single photon emission computerized tomography (SPECT), magnetic resonance imaging (MRI), nuclear magnetic is imaging (NMI), fluoroscopy, ultrasound, X-ray radiography, endoscopy, elastography, tactile imaging, and thermography. (Measurement and recording techniques which are not primarily designed to produce images, such as electroencephalography (EEG), magnetoencephalography (MEG), electrocardiography (ECG), and others represent other applicable techniques).

For such applications, the payload may comprise such imaging agents as contrast agents, radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, fluorine (F) including [19]-F, iron (Fe), manganese (Mn), thallium (Tl), chromium (Cr), including $^{51}$Cr, carbon (C), including $^{11}$C, or the like, fluorescently labeled compounds, etc. Such ORE bearing payloads are also useful for labeling molecules in a mixture, where the target molecule has been pre-labeled by the complementary reaction partner.

Optical agents such as fluorescent, and UV-Vis probes and well as Near Infrared Dyes are potential payloads.

In yet another application, the "payload" may be chosen such that it functions to sterically hinder or alter the binding specificity of a specific target binding protein. Such entities may take many forms which are readily determinable by those skilled in the art, and include various chemical groups which have affinities for functional sites on the protein. Such payloads may also comprise amino acids, oligomeric structures which themselves serve to provide binding affinity for a target molecule, much like biotin, or the like. Such payloads find use, for example, in inhibiting the ability of a binding protein to bind to its protein target and for inactivating cell membrane proteins, such as channels, enzymatic proteins, specific receptors, and the like. Such payloads may also serve a research purpose, for example, in allowing the dissection of the function of a variety of surface membrane proteins or for the identification and/or purification of the labeled target molecule.

In still another application the payload may be chosen to improve the pharmacokinetics of a drug, e.g., by increasing its duration of action, decreasing its immunogenicity, and/or its rate of metabolism. Such payloads may take several forms, which include polymers, such as polyethylene glycol and polysialic acid polymers and various proteins such as human serum albumin that serve to maintain high levels in the circulation by limiting excretion in the glomerulus.

In yet another application, the payload may be a companion protein that forms homo- or hetero-dimers that are more active than individual monomers and/or provide multiple biological activities useful in therapeutic applications.

In yet another application the payload may be a drug or toxin that provides an antibody-drug conjugate of therapeutic utility.

In still other applications the payload or the ORE-labeled protein may be an antibody that serves to deliver the attached component to a target cell for therapeutic reasons as in the case of antibody-drug conjugates.

In yet another application the payload or ORE-labeled protein may be an annexin protein that serves to deliver entities to regions of elevated apoptosis for therapeutic benefit.

In each of the above applications, covalent bonding of the payload to the acceptor ORE-labeled protein serves to augment or add biological functions to the target molecule containing its reaction partner. Thus, by employing the subject compositions, one may modify the nature of the target molecule, change the characteristics of the target molecule, allow for the identification and/or isolation of the target molecule, etc.

The variable element will be bonded to the orthogonally reactive entity (ORE) through a unit, which will comprise a chemically reactive function (e.g., thioester) which will react with a reactive functionality (e g , amino) at the target protein site to form a covalent bond. Covalent bond formation at the target protein, in turn, results in covalently bonding the ORE to the target site with concomitant liberation of the variable element.

The compositions of the invention will include a reactive functionality, containing —S—CO—R—, —O—CO—R, —O—CS—R, —S—R—CH$_2$—, —O—R—CH$_2$, where R=aryl or alkyl. The reactive functionality will generally be stable in an aqueous environment within the timeframe of the first reaction and will usually contain an acyl group, or an imidate, thereby being capable of forming a covalent bond with an amino group of the target protein, to give an amide or amidine derivative. For the most part, the reactive esters will be thiol- or oxygen-esters and involve phenolic compounds, or be alkyl esters, and the like.

Whereas the reactive functionality is usually chosen to react with an amino group at the target protein, free thiol moieties on the target protein will also be exploited where the goal is to selectively label a single free cysteine in the presence of others. For example, the reactive functionality may comprise an imine, thioimine, sulfonates such as tosylates, vinyl sulfones, maleimido, a-halomethylketone, benzyl halide or disulfide for bonding to thiol residues.

The composition of the invention may include a linker between the ORE and the variable element. The linker may provide for synthetic convenience, particular physical characteristics of the total composition, e.g. water solubility, reduced non-specific binding, is the group bonded to the reactive functionality to provide an ester, thioester, imidate, thioimine, or the like. For the most part, the linker, when other than a single bond, will have from about 2-30 carbon atoms, and from about 0-10, more usually 1-8 heteroatoms, which for the most part will be O, N, Se, and S. The particular linker's selection is based on the nature of ORE and the variable structural group and will be designed to provide convenient characteristics for deployment of the molecule in the context of the relevant biological milieu. Of particular interest, where a linker atom constitutes part of the reactive functionality, is to have an aromatic derivative, so that the heteroatom of the reactive functionality is bonded directly to an aromatic carbon atom. Alternatively, one may exploit non-aryl thioesters and the like, using linker chains that contain alkylene or alkyleneoxy.

The linker may have various functions: to enhance the reactivity of the tripartite agent; to provide for enhanced water solubility; by providing for a useful linking group between the ORE and the variable element. For the most part, the linker will be bifunctional of from about 1-20 atoms in the chain, which atoms may be carbon, nitrogen, oxygen, sulfur, selenium, and the like. The linker may contain alkylene groups, generally of from 2-16, more usually of from 1-25 carbon atoms, polyoxyalkylene groups, where the alkylene groups will be of 2-3 carbon atoms, and having from 1-8, more usually of from about 1-6 units, an amino acid, including alpha and omega amino acids, or oligopeptide having from 1-8, usually 1-6 amino acids, where the amino acids may be polar or non-polar, charged or uncharged, aliphatic, alicyclic, aromatic or heterocyclic, naturally occurring or synthetic.

As is evident from the above, the various units of the ultimate rapid labeling tripartite agents to be employed as the first labeling molecules will be selected for compatibility, particularly to impart stability to library components. The components of the multicomponent agent will also need to be selected in relation to the use of the compound, and the effect of the components on the intended use of the compound.

For identification of members of the library having increased reactivity for a particular amino group of the protein target, relative to other members of the library, as indicated previously, depending upon the size of the library, all or a portion of the members of the library may be combined with the pure target protein in an appropriate reaction medium. The medium will vary widely, depending upon the nature of the target compound, and the environment in which the subject tripartite agents will be used for bonding to the target compound. For the most part, the media will be polar, particularly aqueous, and may be buffered or otherwise modified to as to more closely mimic the ultimate environment in which the subject compounds will be used and the protein's biological activity can be maintained. The concentrations of the target protein and the library members may be varied widely, usually being determined empirically, so as to optimize the differentiation between the various members of the library. Generally, for screening purposes, concentrations of the target compound will be in the range of about 0.05 to 5 nM, preferably in the range of about 0.1 to 1.0 nM, while concentrations of the library will vary in the range of about 10 to 150 nM, preferably in the range of from about 50 to 100 nM and more preferably in the range of from about 75 to 85 nM.

The temperature of the reaction may be varied over a broad range compatible with the stability of the components of the system, frequently being room temperature or the temperature of the environment in which the subject compounds will be used. To the extent that the subject compositions will be used physiologically, the temperature will generally be in the range of about 10-45° C., more usually about 37° C.

The determination of reactivity for the target exhibited by the various members of the library may be made by determining the composition of the liberated variable elements (that differentiate each of the library members) at a single time point or a plurality of time points after the reaction is initiated. For the most part, those variable elements which are liberated the earliest after the reaction is initiated are those which are likely to exhibit the greatest reactivity for that target protein. Usually, the reaction will be allowed to proceed until there is a sufficient population of liberated variable elements to allow for their ready determination and differentiation. The leaving groups whose structures distinguish each library member may be analyzed by any convenient means, including mass spectrometry, gel electrophoresis, chromatography, e.g. HPLC, TLC, or the like, where if appropriate, the separated components may then be sequenced. Where a plurality of aliquots of the library is used, those sequences demonstrating preferred reactivities may then be combined in a subsequent determination for direct comparison.

The screening of libraries containing an entity which becomes covalently bound to the target protein is usually conducted in two sequential steps. The first step of the screening to process involves contacting the target protein with library members. The reaction can be performed in solution using the library portioned into pools, or spatially separated using one well per compound. Alternatively, the first step of the library screen can also be performed with libraries on solid supports, using a one bead-one compound (OBOC) motif.

Library reactions are typically conducted at room temperature or 37° C., although not exclusively so, in the wells of polypropylene plates. Specified wells contain the target protein that is typically present at concentrations between 0.1 and 1 µM, in a buffered solution that is of an appropriate composition, and at a pH which maintains the native biological structure and function of the target protein.

Solution labeling reactions are initiated by the addition of an aliquot containing library members in DMSO, DMF, or $CH_3CN$, to give typical concentrations of 80 µM (2% DMSO) of total library when screened in pools, and up to 5 µM (2% DMSO) in spatially separated formats. The labeling reactions are terminated at a specified time, which may be as short as 5 seconds using automation, or longer than 1 hour, by the addition of a suitable quench reagent (i.e. hydroxylamine for quenching thioesters). Alternatively, the reaction may be terminated by substantially lowering the pH.

Screens of labeling reactions using solid phase technologies are initiated by mixing beads linked to library members with protein solution. Three methods can be used to promote protein labeling. The first option permits the reaction of the entire library with a biomolecule of choice in a single reaction vessel. A second possibility involves dividing the entire library of beads into pools and screening each pool separately against protein. The third approach calls for placing each bead in a single well, so protein labeling is performed in a spatially separated manner For libraries on solid supports, reactions can be terminated by simply filtering the buffered solution containing protein from the libraries on beads. The detection of labeled protein can be performed as follows.

Biotin, in classic sandwich Enzyme-Linked-Immunoassays (ELISA's) can be employed to detect covalent bonding, through reactions of commercial biotin probes with azide labeled protein. Briefly, polystyrene 96-well plates are coated with an antibody that specifically binds the target protein and most library-modified forms thereof. A portion of each reaction mixture is transferred/filtered to the corresponding wells of an antibody-coated plate, and the target protein is incubated with the antibody for at least 2 hours at RT, or overnight at 4 C. The plate is then emptied and washed 10 times using phosphate buffered saline (PBS, 10 mM Pi, pH 7.4, 137 mM NaCl, 2.7 mM KCl) with 0.05% Tween 20. This washing procedure removes from the well all reagents that are not attached to the antibody. After reaction with a biotin species such as a biotin-DIBCO reagent, a solution containing the enzyme conjugate strepavidin-horseradish peroxidase is then added to the washed wells, and the binding of the strepavidin conjugate to the biotinylated protein (which is bound, in turn, to the capture antibody), is complete after 30 minutes. The plate is then washed as described above, and ortho-phenylene diamine or ABTS (2,2'-azinobis[3-ethylbenzthiazoline-6-sulfonic acid]-diammonium salt) is added as a substrate of the peroxidase enzyme to give a visual measure of the amount of conjugate present in each well; the amount of conjugate is proportional to the amount of modified target protein in the well. The optical densities of each well are measured, and the values obtained are recorded in a computer spreadsheet and analyzed.

Consequently, the ELISA method of screening is applicable for measurement of Orthogonal Reactive Entities (ORE) that can be converted to a detectable adduct. (For example, acetylenes or azides can be converted to triazole adducts which are measurable by standard methods known in the art (ELISA (e g , alkaline phosphatase methodology in conjunction with dibenzocyclooctynes to capture azide-labeled proteins. Analogous NIR measurements, fluorescence, etc., can also be employed (Fluorogenic click reaction. Le Droumaguet C, Wang C, Wang Q. Chem Soc Rev. 2010 39(4):1233-9)). Attachments of OREs provide flexibility of choice in screening methodology. Biomolecules modified with OREs can easily be converted into biotin-containing formats and assayed by an approach as described above. Alternative screens may utilize fluorescence. Alkyne-labeled protein can react with commercially available reagents producing fluorescently labeled protein. Modifications of sandwich ELISA can be implemented in the detection of such adducts. The use of dibenzocyclooctynes to capture azide-lableled proteins is a particularly powerful method.

A simple example that follows suffices to illustrate one example of applying appropriate methodology. Briefly, polystyrene 96-well plates are coated with antibodies that specifically bind the target protein and modified forms thereof. Mixtures with fluorescently or NIR labeled antibody from reaction of azide-labeled antibody with DIBCO-based probes may then be transferred to the corresponding wells of the antibody-coated plate, and the binding of target protein to antibody ensues for at least 2 hours at RT, or overnight at 4 C. The plate is then emptied and washed 10 times using phosphate buffered saline (PBS, 10 mM Pi, pH 7.4, 137 mM NaCl, 2.7 mM KCl) with 0.05% Tween 20. This washing procedure removes non-covalently bound fluorescent material. The fluorescence of each well is measured, and the values obtained are recorded in a computer spreadsheet and analyzed.

When reactive thioester libraries are utilized, the progress of the reaction can be monitored using thiol-specific fluorescent probes. For screens performed with libraries on solid supports, free thiols formed upon treatment with protein, can be scavenged by fluorescent agents known in the art. The fluorescent beads can then be separated from non-fluorescent beads and the structure of the associated library member can then be determined by mass spectrometry.

Implementation of Mass Spectrometry (MS) as a detection method allows for simultaneous data collection on the labeling status of the protein, directly. MS screens we have invented deliver rapid information on the extent of labeling of the target protein and provide rapid and unambiguous determination of the entity responsible for labeling.

Monitoring the reaction course of reacting pools using mass spectrometry can deliver valuable information on both the extent of labeling and the labeling entity. We design pools in which no two library members in a specific pool, have the same mass. Pools are analyzed (MALDI/ESI) before and post-reaction to determine changes in intensity of the peaks of library members. Notable decreases in intensity track with the high reactivity of library members.

When the labeling reaction is performed in solution using spatially separated entities the process can be fully automated. Library members can be distributed to the wells of 384 well plates, followed by the addition of a protein solution. At a specific time, which may be as short as 5 seconds or longer than 1 hour, reaction can be terminated by lowering the pH (achieved by mixing samples with a MALDI matrix and transferring them individually into 384 spots of the MALDI plate). Data acquisition can be fully automated delivering information on the extent of protein labeling and the structural properties of library members.

For screens performed on solid supports, libraries can be prepared that are cleavable with ammonia. In such cases the process can be automated as described above, except that libraries on beads, rather than in solution, occupy the well. Reactions can be terminated by separating the soluble medium containing protein from contact with the bead and subjecting such samples from each well to mass spectrometry (MALDI/ESI) analysis to determine the extent of protein labeling By relating samples that produced the most highly labeled protein to their host wells, library entities therein, can then be cleaved from their associated beads by addition of ammonia. Structural analyses (MALDI/ESI) of the released entities can then be performed to identify fast labelers, whose reactivity and specificity can be then be confirmed.

The subject affinity label compounds will be synthesized in accordance with conventional methods. Synthesizers are commercially available for synthesizing oligonucleotides and oligopeptides. See the references cited above. Various conventional chemistries may be employed. Depending upon the nature of the functional group, the linker, and the ORE, synthetic strategies will be devised which allow for synthesis of the molecule at reasonable yields, and without the formation of complex mixtures. The particular synthetic strategy will be determined empirically, and on a case by case basis. Methods for combining various compounds are well known in the literature, and can be employed with advantage. Where precursors are known for the payload, particularly prod rugs for drugs, the prodrugs will frequently indicate the nature of the linking group and ORE in the second species bearing the payload.

The subject products, which comprise payloads crosslinked to proteins, when administered physiologically, can be administered as a bolus, but may be introduced slowly over time by transfusion using metered flow, or the like. Alternatively, although less preferable, blood may be removed from the host, contacted with the affinity label compound ex vivo, and returned to the host. However, the method of administration is dependent upon the particular application and may depend upon the locus of action and pharmaceutic properties of the payload or protein. The crosslinked products will be administered in a physiologically acceptable medium, e.g., deionized water, phosphate buffered saline, saline, mannitol, aqueous glucose, alcohol, vegetable oil, or the like. Usually, a single injection will be employed although more than one injection may be used, if desired. The crosslinked products may be administered by any convenient means, including syringe, catheter, or the like. The particular manner of administration will vary depending upon the amount to be administered, whether a single bolus, sequential, or continuous administration, or the like. Administration will often be intravascular, where the site of introduction is not critical to this invention, preferably at a site where there is rapid blood flow, e.g., intravenously, peripheral or central vein. The intent is that the compound administered be effectively distributed in the vascular system so as to be able to react with target molecules therein.

The dosage of the crosslinked product will depend upon the specific entity being employed and will, therefore, be dependent on the adverse effects of the entity of interest, if any, the indication being sought, the sensitivity of the compound to destruction by vascular components, the route of administration, and the like. As necessary, the dosage of the crosslinked product may be determined empirically, initially using a small multiple of the dosage normally administered, and as greater experience is obtained, enhancing the dosage. Dosages will generally be in the range of 1 ng/Kg to 10 mg/Kg, usually being determined empirically in accordance with known ways, as provided for in preclinical and clinical studies.

Targeted Kinetic Labeling Libraries and Traceless Affinity Labels

The foregoing description is based primarily on libraries in which the affinity element contains only oligomeric functionality and there is essentially no information about ligands to the target protein. Such libraries are constructed by randomizing amino acids among the several variable positions and are "universal" kinetic labeling libraries in that they represent unbiased first line screens of proteins. When binding determinants to specific sites are available it is expedient to incorporate, or build on, such known affinity (peptidyl or non-peptidyl) elements in the library. By making them a constant feature of the affinity group in combination with variable (e.g., peptidyl) elements, the libraries are essentially targeted and biased toward targeted protein sites. In this scenario, the overall complexity of the combinatorial library may be reduced while the affinities of library members for the protein target are enhanced.

Reformatted or Re-engineered Affinity Labels

A characteristic feature of kinetic labeling libraries is that the entities conjugated to the target protein are derived from traceless linkers (or alternatively traceless affinity labels). This feature is of the utmost importance to labeling in that it allows for the presence of widely diverse binding determinants in the affinity label, which do not appear in the conjugated protein. This design element provides an enormous advantage over approaches which lead to the retention of binding determinants which often are quite complex, and tantamount to extraneous elements with neither a functional role nor desirable properties.

Consequently, this invention is not only directed toward site-selective labeling of target proteins, such as antibodies, with OREs, whether it be through library screening or through innovative reformatting of an affinity label which hitherto conjugates binding determinants to the target protein.

We provide specific examples of the subject invention: traceless linkers of antibodies which target the nucleotide binding pocket (NBP) of IgG antibodies. These examples evoke the principle that the affinity group can be exploited to accomplish traceless site-selective labeling without compromising the integrity of the product.

This approach builds on the observation of Rajagopalan et al. (*Proc Natl Acad Sci USA*. 1996 Jun. 11; 93 (12):6019-24. *Novel unconventional binding site in the variable region of immunoglobulins*) who have identified a nucleotide binding pocket (NBP) that exists in all immunoglobulin Fab arms. This highly conserved pocket is situated between the variable light (VL) and variable heavy (VH) domains of all antibody isotypes. Through an in silico docking study, Handlogten et al. identified indole-3-butryic acid (4-(3-indolyl)butyric acid) as a compound that binds to the NBP with $K_d$'s ranging from 1 to 8 µM, with binding affinity being dependent on the antibody. Alves et al. reported a UV photo-cross-linking method that relies on the indole group to cross-link to specific residues within the NBP of IgG. Alves, N. J. et al. (2013) *Oriented antibody immobilization by site-specific UV photocrosslinking of biotin at the conserved nucleotide binding site for enhanced antigen detection*. Biosens. Bioelectron. 49, 387-393.; Handlogten, M. W. et al. (2011) *Design of a heterobivalent ligand to inhibit IgE clustering on mast cells*. Chem. Biol. 18, 1179-1188. (26) Alves, N. J. et al. (2012) *Small-molecule-based affinity chromatography method for antibody purification via nucleotide binding site targeting*. Anal. Chem. 84, 7721-8 and reference therein.

Following on Handlogten et al., Lac et al. have described site-specific ligation as specificity to the NBP of the Fab domain (Covalent Chemical Ligation Strategy for Mono- and Polyclonal Immunoglobulins at Their Nucleotide Binding Sites, Lac et al., 2016 Bioconjugate Chem. 159-169.)

These workers exploited the reported nucleotide-binding pocket (NBP) in the Fab arms of immunoglobulins by developing indole-based, 5-fluoro-2,4-dinitrobenzene-derivatized OBOC peptide libraries for the identification of affinity elements using peptides as short as dipeptides that can be used as site-specific derivatization agents against both mono- and polyclonal antibodies. Major disadvantages of this approach are related to the size and structure of the substrate, its retention in the labeled antibody, and the presence of a potential hapten (dinitrobenzene).

Indeed, such species can be re-engineered as traceless linkers that are the subject of this invention. Traceless linkers offer distinct advantages over the approach of Lac et al. for the following reasons: (1) the affinity element, that has no functional purpose in the final product, is released as part of the leaving group (it is usually a small molecule coproduct, that is easily separated from the protein or antibody conjugate); (2) only a structurally simple entity that can easily be conjugated to virtually any payload is transferred to the antibody; (3) nitrobenzene moieties, potentially toxic, haptens, undesirable chemical functionalities, are not required for attachment.

Hence, notwithstanding the alleged selectivity imparted by the linker of Lac et al., the fact that the linker is retained in the final product with indole, dinitrobenzenoid, and peptide functionality, in addition to the essential label, brings with it a number of potential problems. First, the additional functionality represents a point of metabolic attack that could vitiate any potential therapeutic effects ultimately intended. Secondly, potential toxic effects of the dinitrobenzenoid moiety are further considerations. Thirdly, the complex structural features of the linker must be accommodated without compromising the biological activities of attached therapeutic payloads. This requirement is likely to limit the breadth of its utility and may require labor-intensive customization for each linker/payload combination Consequently, it is a considerable advantage to label the conserved site with minimal functionality that enables the attachment of numerous and diverse payloads to a universal ORE. Thus improvements in linker technology, which are designed in the first instance to provide proteins labeled with traceless linkers, of minimal functionality, unencumbered by extraneous elements, are subjects of this invention. For purposes of this invention, minimal is defined as a click chemistry function such as an alkyne or cycloalkyne, azide, nitrone, nitrile oxide, or tetrazine, linked to an alkyl, alkylene oxide, peptide or peptoid chain.

In one embodiment of this invention (for purposes of illustration using a lysine ε-amino group of an exemplary indole-amine 2, where $X_1X_2X_3X_4X_5X_6X_7X_8$ represent up to 8 amino acid residues), and Z=H, or an electron-withdrawing group (EWD) known in the art, such as nitro, cyano, sulfonyl, carbonyl derivatives and the like), DFDNB can first be converted to the secondary amine (3) by the displacement of fluoride from (1), in which the amino acids are in protected formats. (In some instances it may be necessary to modulate the intrinsic reactivity of the indole nucleophilicity with an EWD group to limit indole reactivity). The resulting monofluoride (3) can then, in turn, be treated with ω-azido-alkyl carboxylates and ω-azido-alkyl thiocarboxylates, for example, to give the active esters and thioesters (4) respectively, for transfer of an ORE (contained in R), site-specifically, to the antibody target.

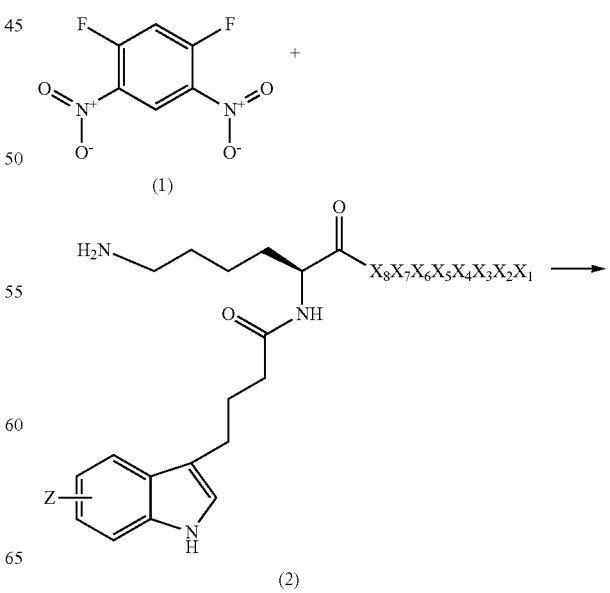

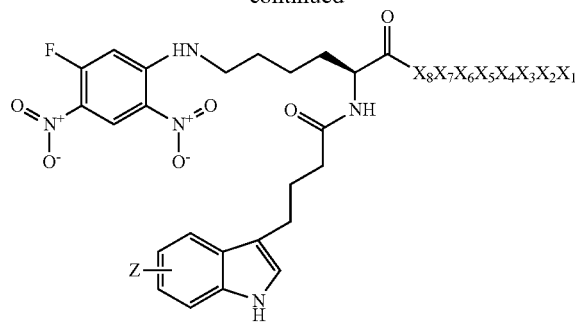

(3)

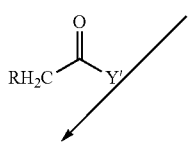

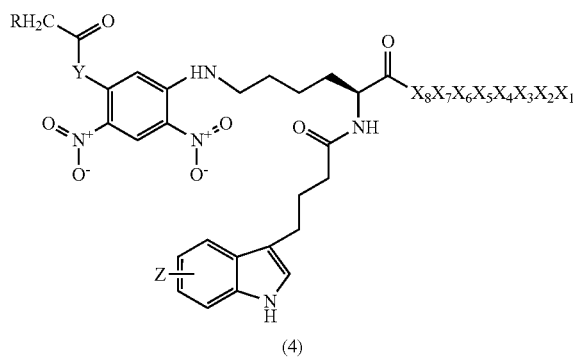

Y = O, S
R = ORE-containing entity
Z = H, EWD ═ NO₂, CN

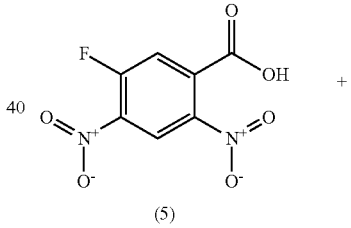

A number of embodiments of this invention illustrate, in principle, how traceless linkers can be re-engineered from 1,5-difluoro-2,4-dinitrobenzene ((1), DFDNB), to produce a potentially reactive acylating agent that is linked to indole-containing frameworks as in the generic structure (2a).

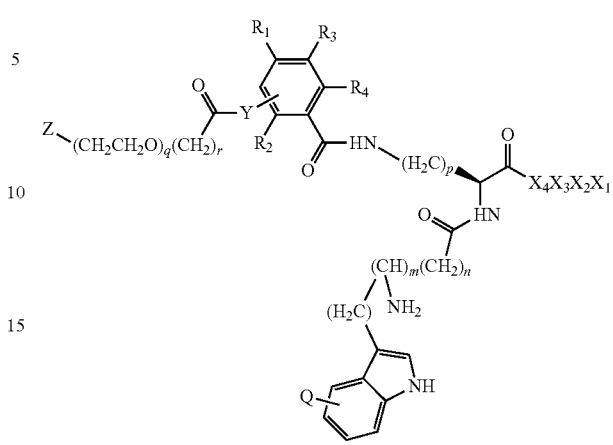

(2a)

p = 1-6; m = 0, n = 1-8; q = 0-100; r = 1-20
R₁, R₂, R₃, R₄ = H, F, Cl, NO₂
X₄, X₃, X₂, X₁ = an amino acid, independently of either D or L configuration
Q = NO₂, CN In a second embodiment, since the fluoride in (6) is activated for displacement by nitro groups, it is also subject to displacement by various organic nucleophiles there is a path to the active esters of general structure (7) to give traceless linkers. These novel entities, like (4), are designed to transfer only the acyl group of (7) and produce a universal handle for further attachment of payloads modified to carry alkynes, e.g., dibenzocycloalkynes.

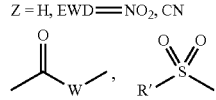

(5)

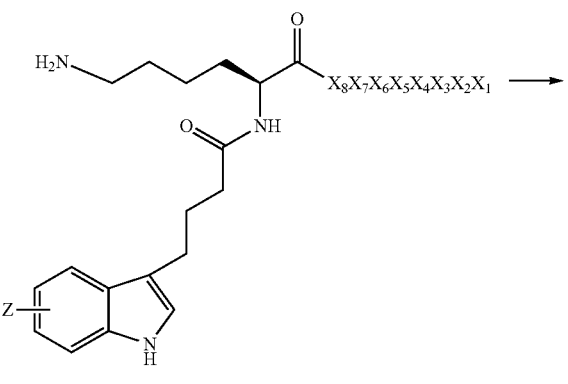

(2)

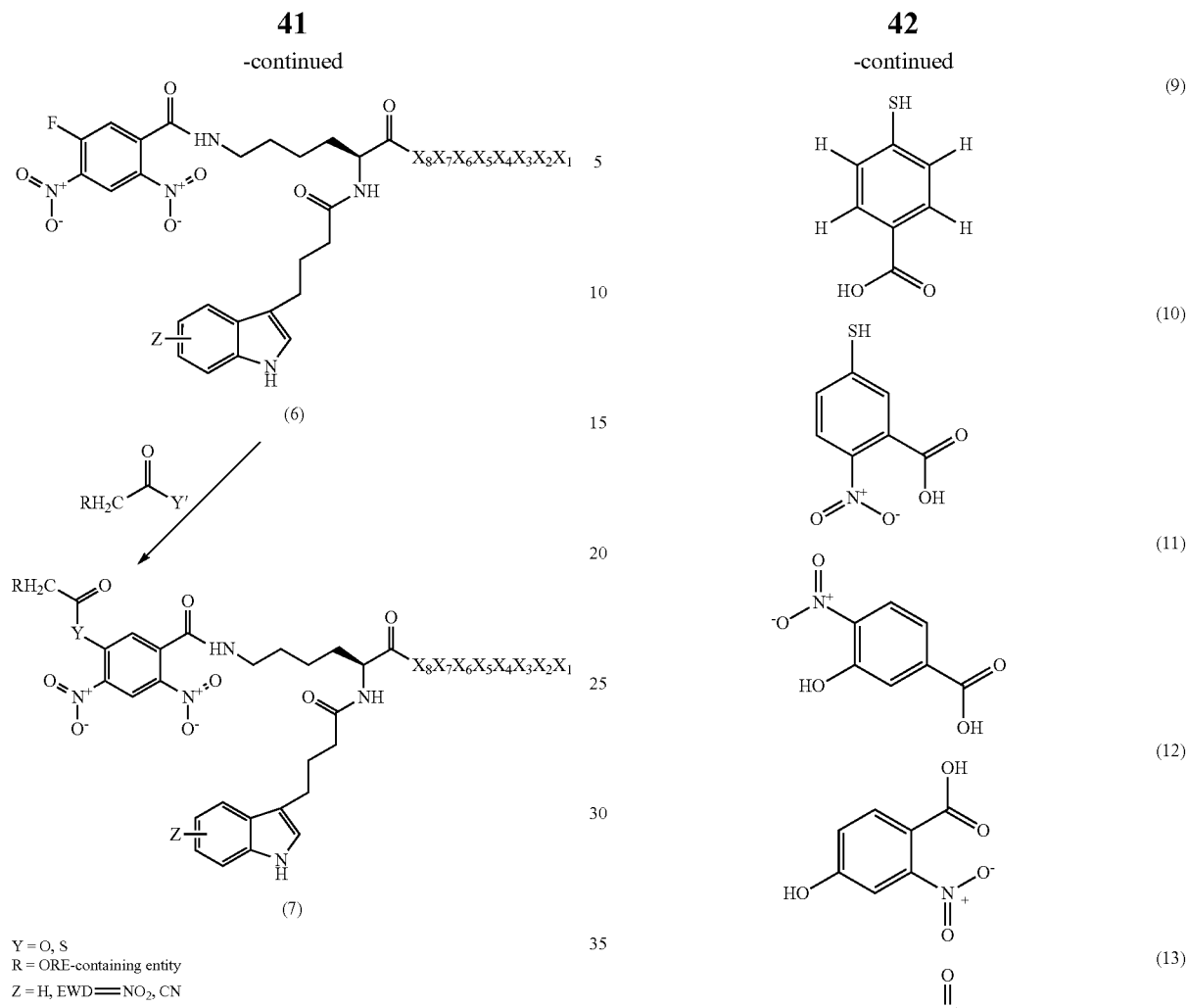

Whereas the foregoing acylating agents are activated by dinitrobenzenoid functionality, reactive phenolic acylators can also be crafted with a single nitro group, and another electron-withdrawing function such as carboxamide; thiophenolic esters can be used as well. For example, phenols and thiophenols (8)-(14), after amide formation with (2) in protected formats known in the art, can then be functionalized as active esters and thioesters. In some instances, activation of the phenolic or thiophenolic component by substituents may be unnecessary, as the proximity and orientation of the antibody and ligand may promote a rapid reaction.

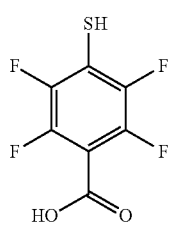

Figure 11:
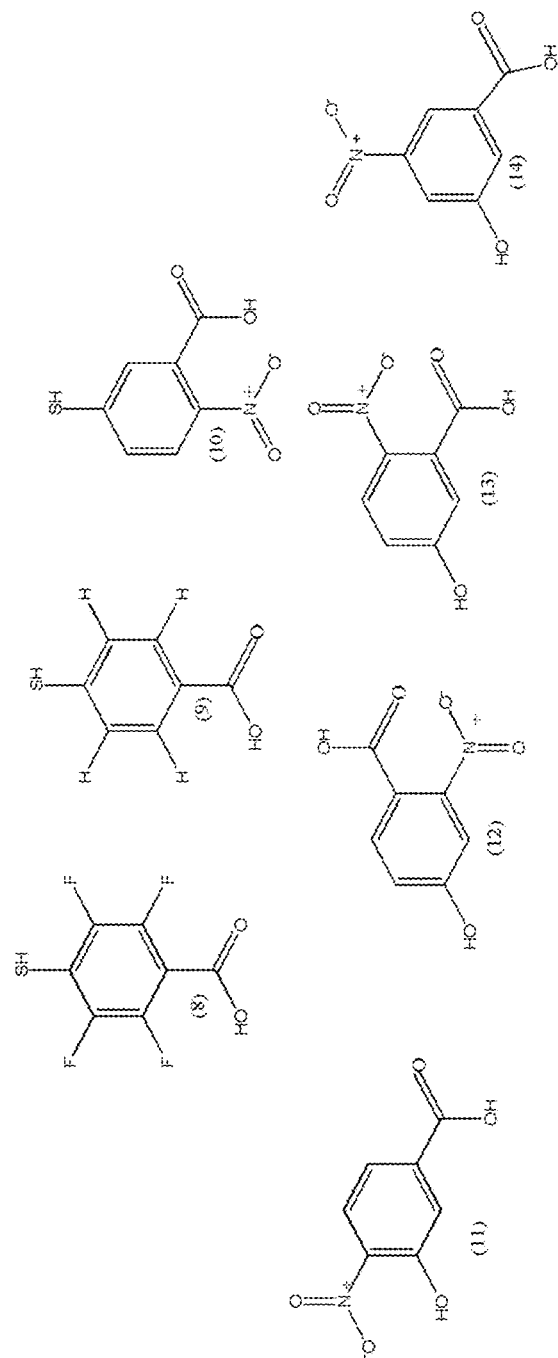
FIG. 11 depicts exemplary prototype molecules based on commercially available phenols and thiophenols that serve as the linker component.

Minimal structural features of KLL libraries of this invention that can be varied for discovery of site-specific labeling agents targeting the NBP, consist of the indole-3-butyric acyl group, amino acids containing amino alkyl side chains as part of the peptidyl affinity element, and an acylating agent. Exemplary prototype molecules are commercially available phenols and thiophenols that can be utilized as part of the acylating entity of the linker, are shown in FIG. 11 and can be incorporated into traceless labeling agents by analogy with those shown in FIGS. 12-14. In certain instances, to lower the reactivity of the indole component for compatibility with the labeling entity, the benzenoid ring is substituted with electron-withdrawing substituents (EWD), Q.

Figure 12:
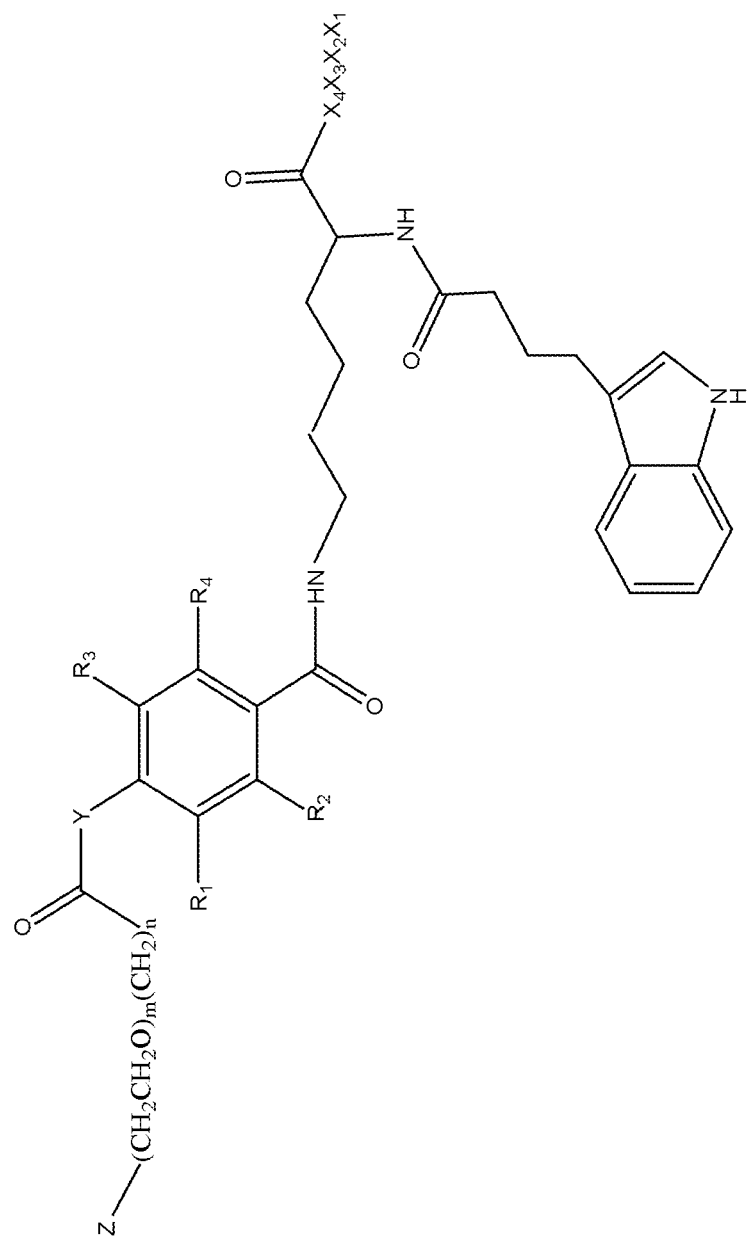
FIG. 12 depicts an exemplary molecule of of general structure containing a para-substituted benzamide linker for selective labeling via acyl transfer mechanisms which contain practical leaving groups that do not appear in the final, labeled protein product.
Figure 13:
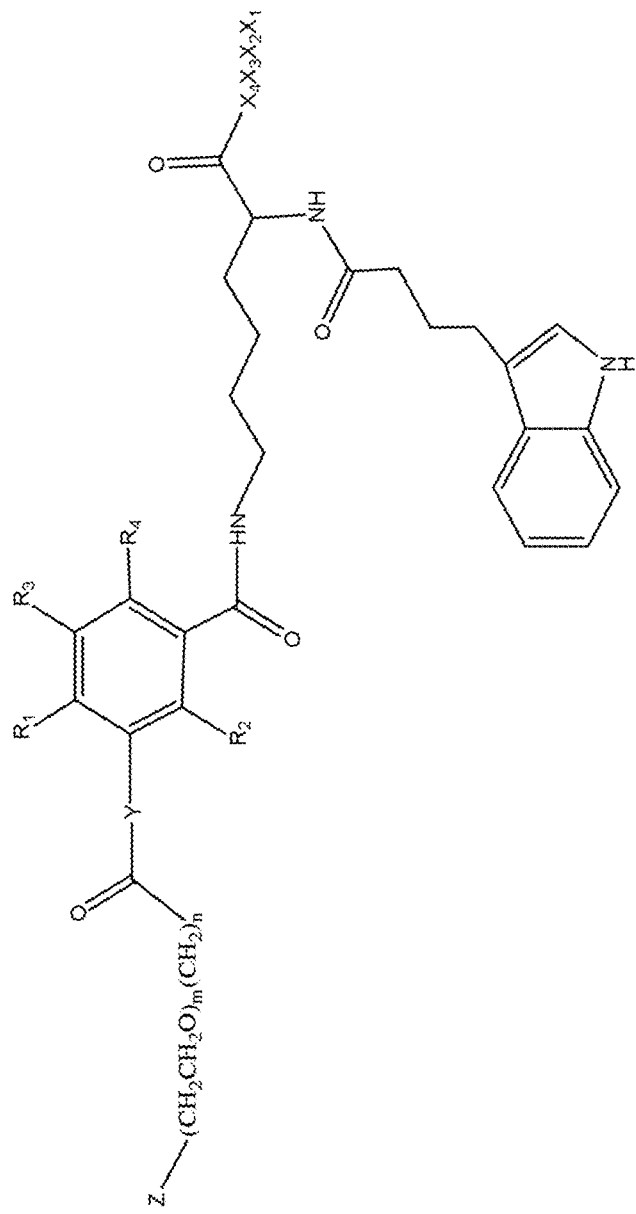
FIG. 13 depicts an exemplary molecule of general structure containing a meta-substituted benzamide linker for selective labeling via acyl transfer mechanisms which contain practical leaving groups that do not appear in the final, labeled protein product.
Figure 14:
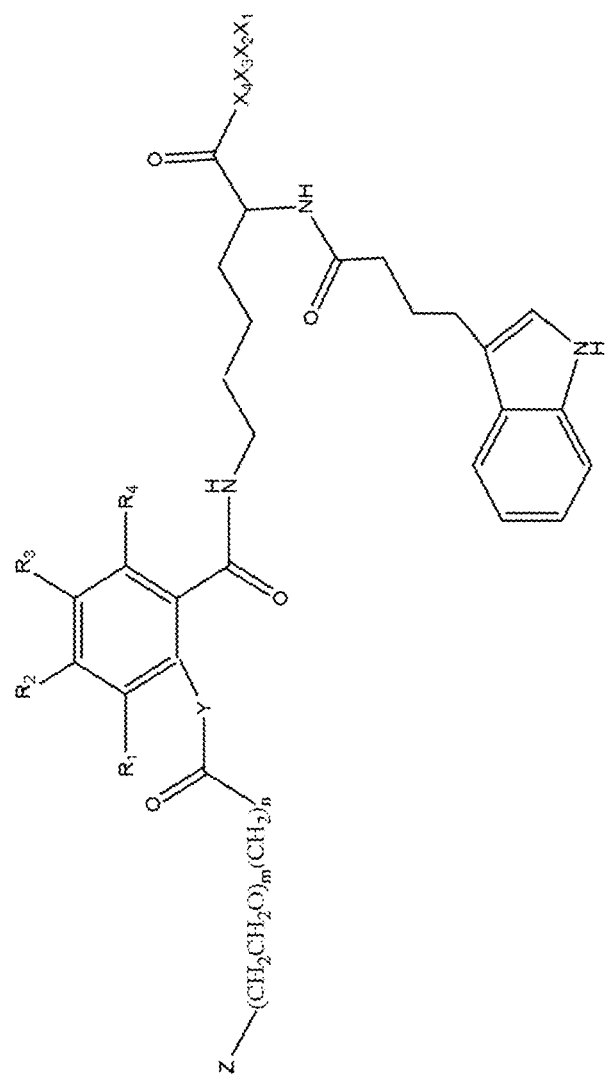
FIG. 14 depicts an exemplary molecule of general structure containing an ortho-substituted benzamide linker for selective labeling via acyl transfer mechanisms which contain practical leaving groups that do not appear in the final, labeled protein product.

For example, in a fifth embodiment of traceless linkers, exemplary molecules for selective labeling via acyl transfer mechanisms which contain practical leaving groups that do not appear in the final, labeled protein product, have the general formulae shown in FIGS. 12-14. and represent the structures of targeted library members, as well as the ultimate labeling agents of the antibody targets.

Further embodiments are generalized in partial label-linker structures (16) and (17) and compared with the mercaptobenzamides (15). In general, for antibody labeling, we claim phenol or thiophenol entities and the corresponding O- and S-aromatic (thio)esters, to which we have bridged N-terminal amino acid side chains of the peptide component, using covalent chemistry.

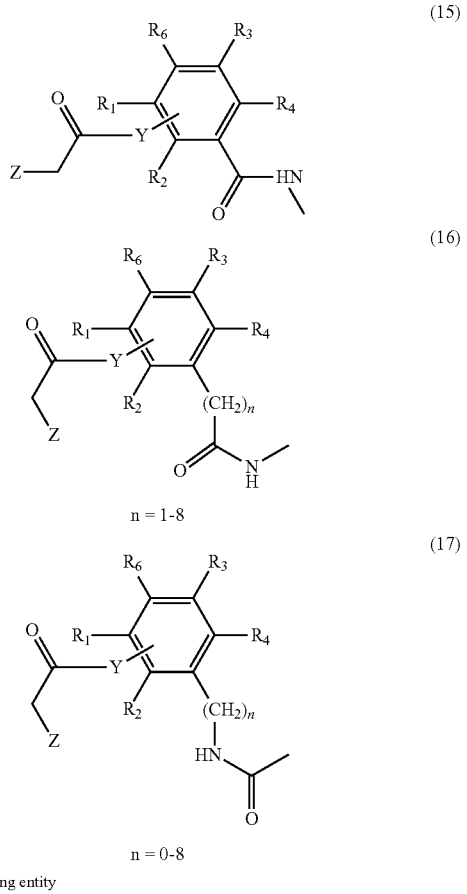

Z = ORE containing entity

Once the ORE is in place on the antibody, single or multiple copies of payloads can be attached by bioorthogonal reactions between click chemistry partners that are known in the art (alkyne/azide, cycloalkyne/azide, tetrazine/trans-cyclooctene). Introduction of payloads by click chemistry is well-precedented for many protein coupling reactions.

For the introduction of multiple copies of a payload, an aspect of this invention employs a peptide auxiliary in which click chemistry reactions are used to attach the payload to the auxiliaries represented by the general structure V. in FIG. 15. Such click chemistry functions are commonly contained within propargylglycine or an E-azidolysine in a peptide framework.

The "click" reactions can be carried out on the peptide auxiliary either before or after it is condensed onto the protein (antibody). Constituent cysteines can be employed in the auxiliary as well, using various cysteine reactive labeling options, including halobenzyl, haloacetyl, and propargyl halide treatment followed by reaction with azides, to introduce payloads. A payload-bearing auxiliary is conjugated to the protein using functionality that can be introduced, by methods known in the art such as acylating the N-terminal of the auxiliary, at an appropriate point in the overall synthetic sequence, so as not to interfere with the attachments of payloads or to compromise payload functionality.

Figure 16:
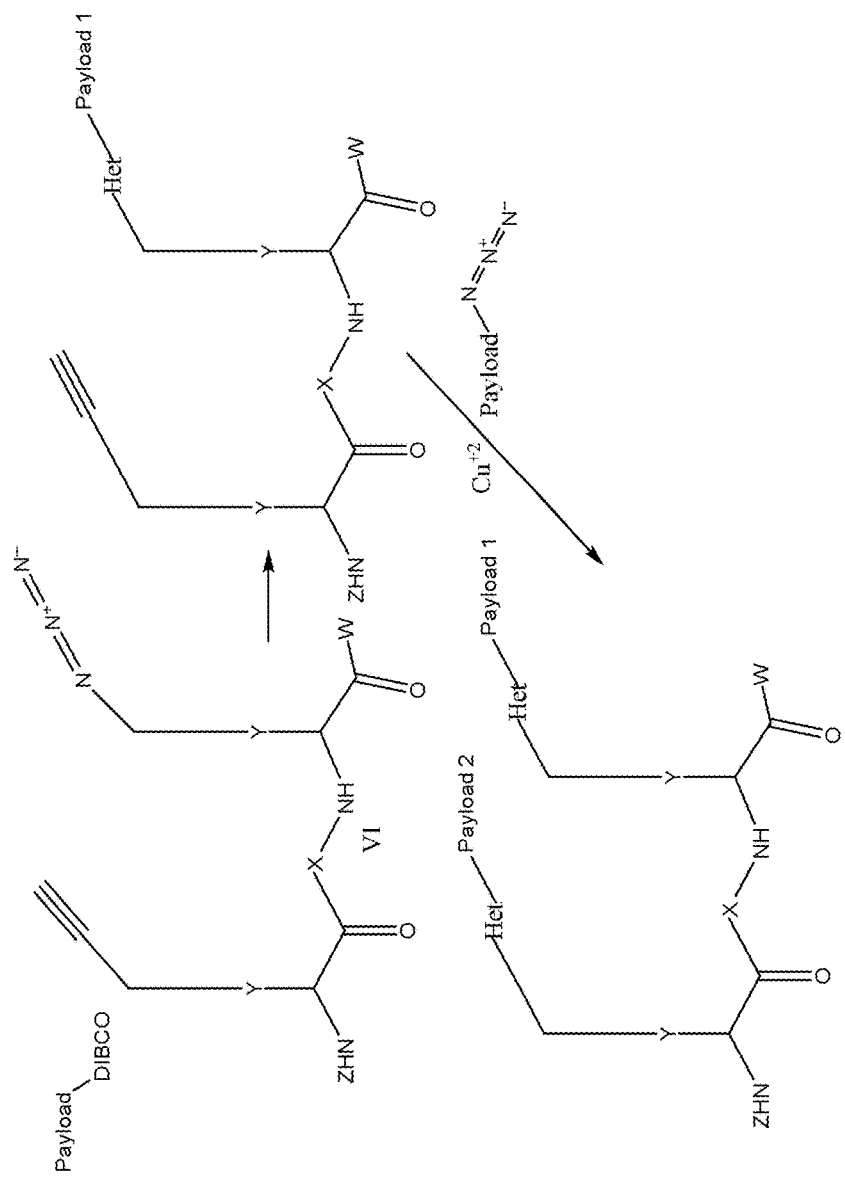
FIG. 16 depicts the introduction of two distinct payloads onto a peptide auxiliary VI. The first payload, modified with the commercially available DIBCO-$NH_2$ is conducted without copper at ambient temperatures. The second condensation requires cupric ion to introduce the payload. The product may also be achieved by inverting the sequence of condensation reactions.
Figure 17:
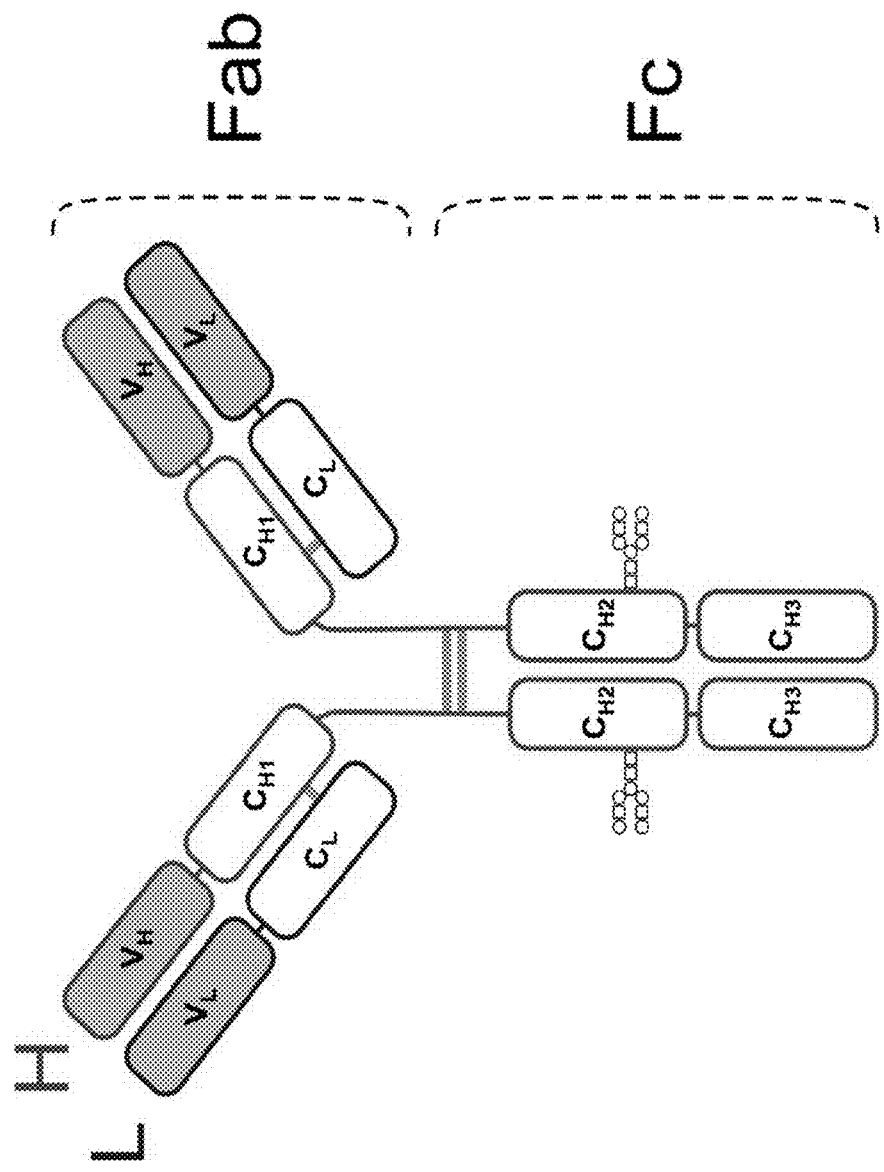
FIG. 17 depicts the structure of IgG antibody.
Figure 18:
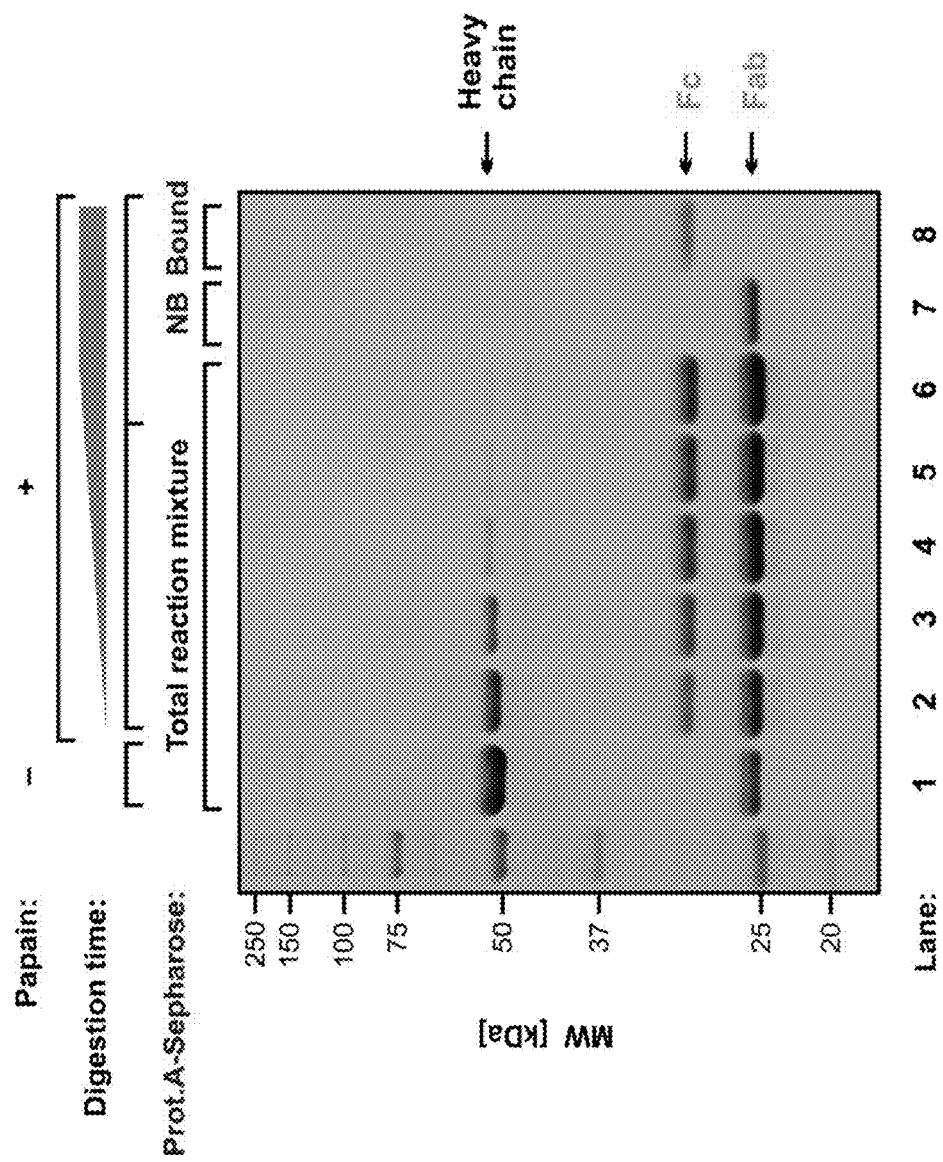
FIG. 18 depicts papain digestion of Ab into Fab and Fc fragments by treatment with papain in solution followed by SDS-PAGE (Coomassie staining).
Figure 19:
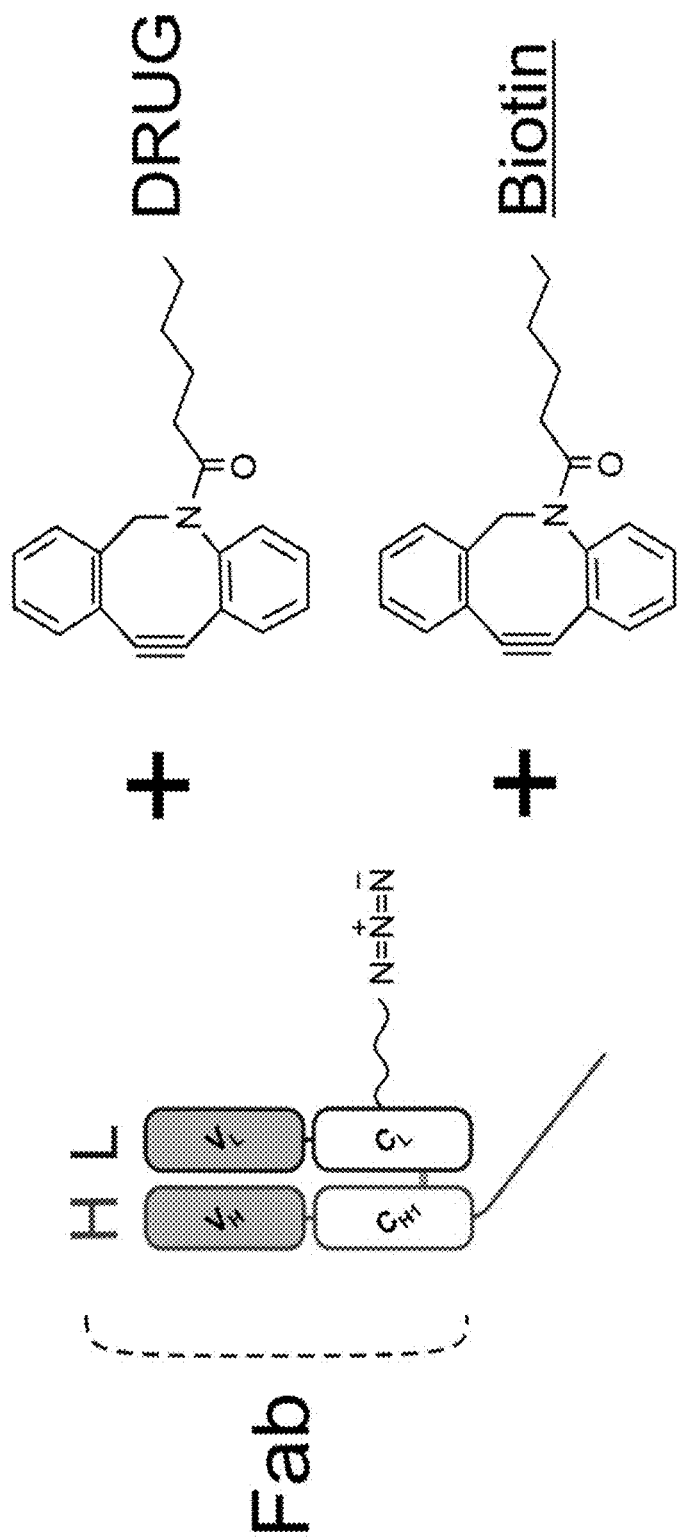
FIG. 19 depicts "click" chemistry-based Ab-drug conjugation.
Figure 20:
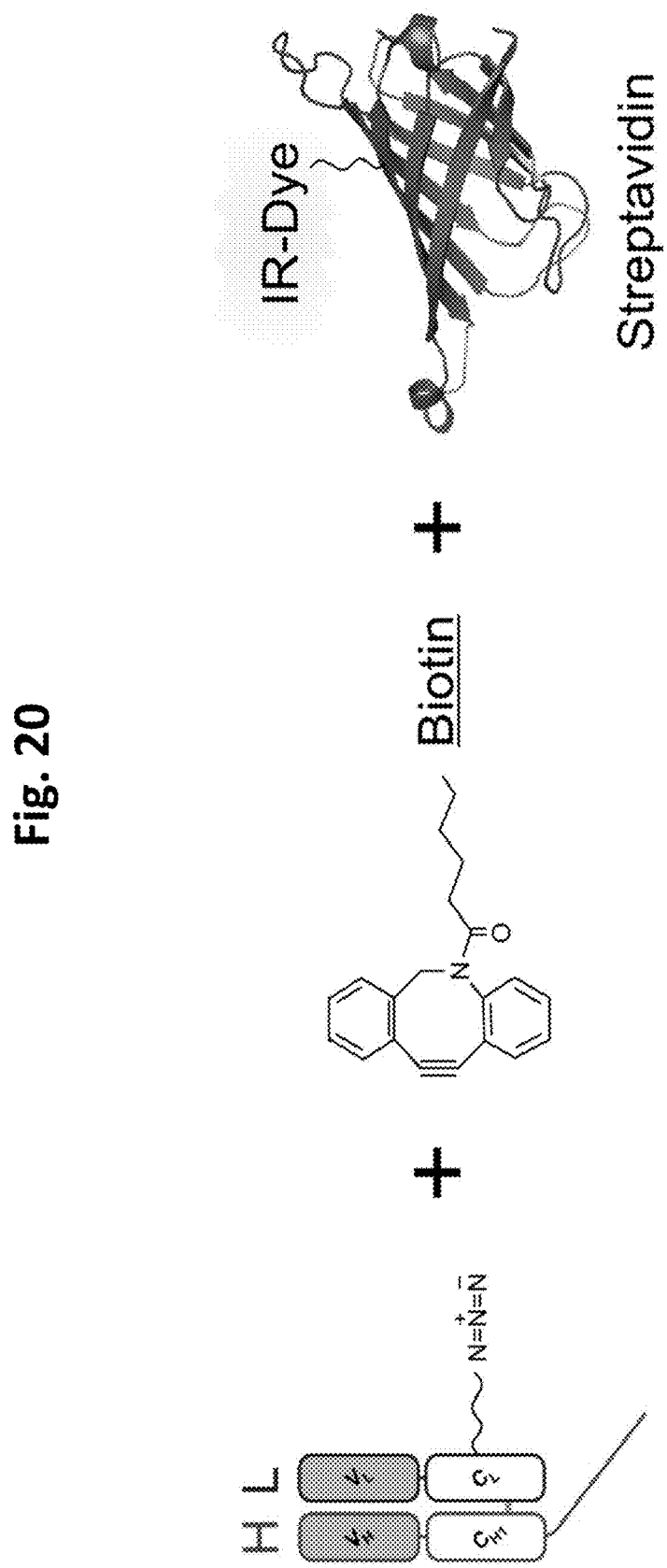
FIG. 20 depicts a technique for IR-Dye/Streptavidin-based detection & quantitation of Ab-labeling.
Figure 21:
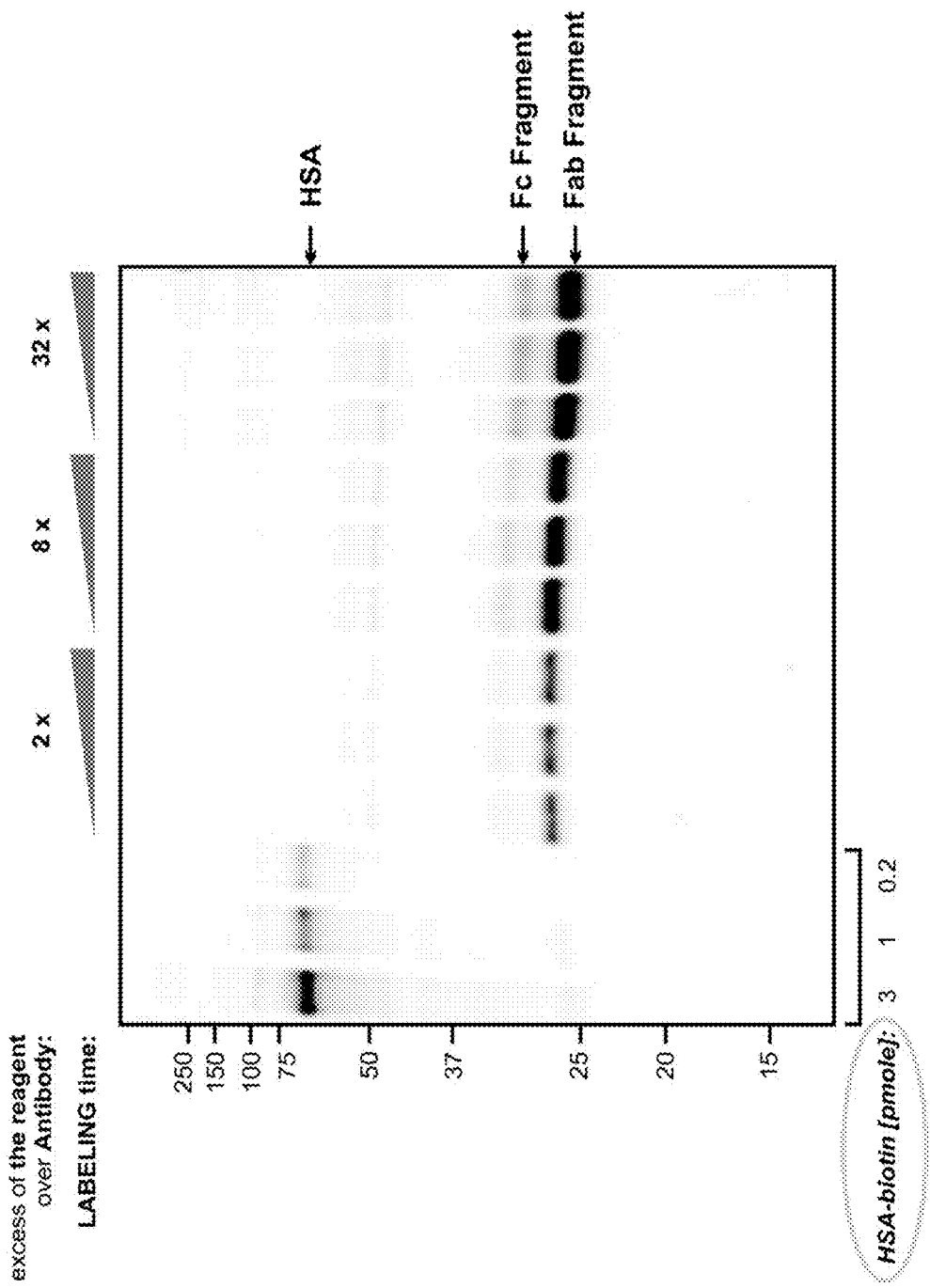
FIG. 21 depicts results of an IR-Dye/Streptavidin-based detection & quantitation of Ab-labeling.
Figure 22:
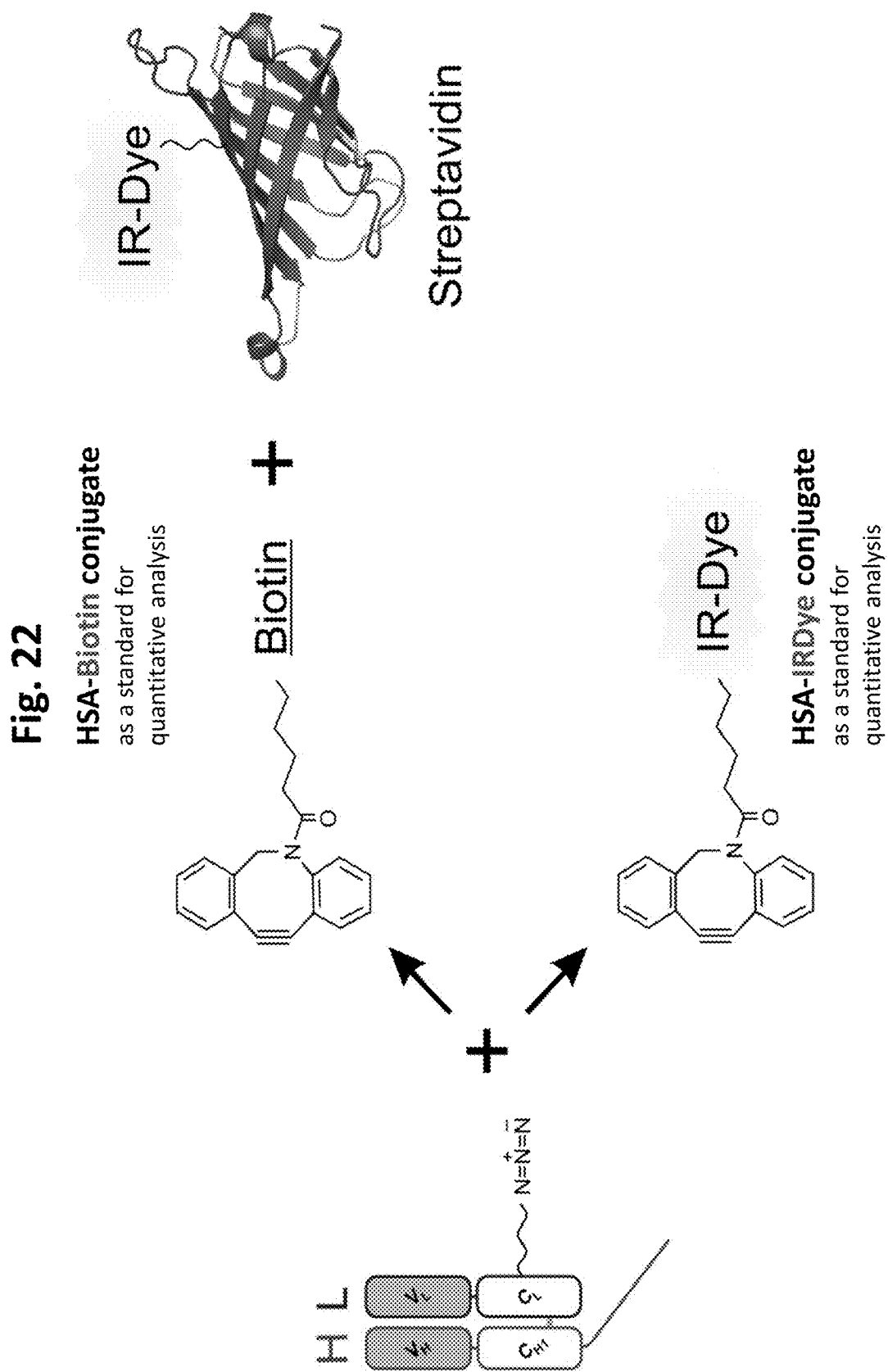
FIG. 22 depicts one step vs. two step-based quantitation of Ab-labeling.
Figure 23:
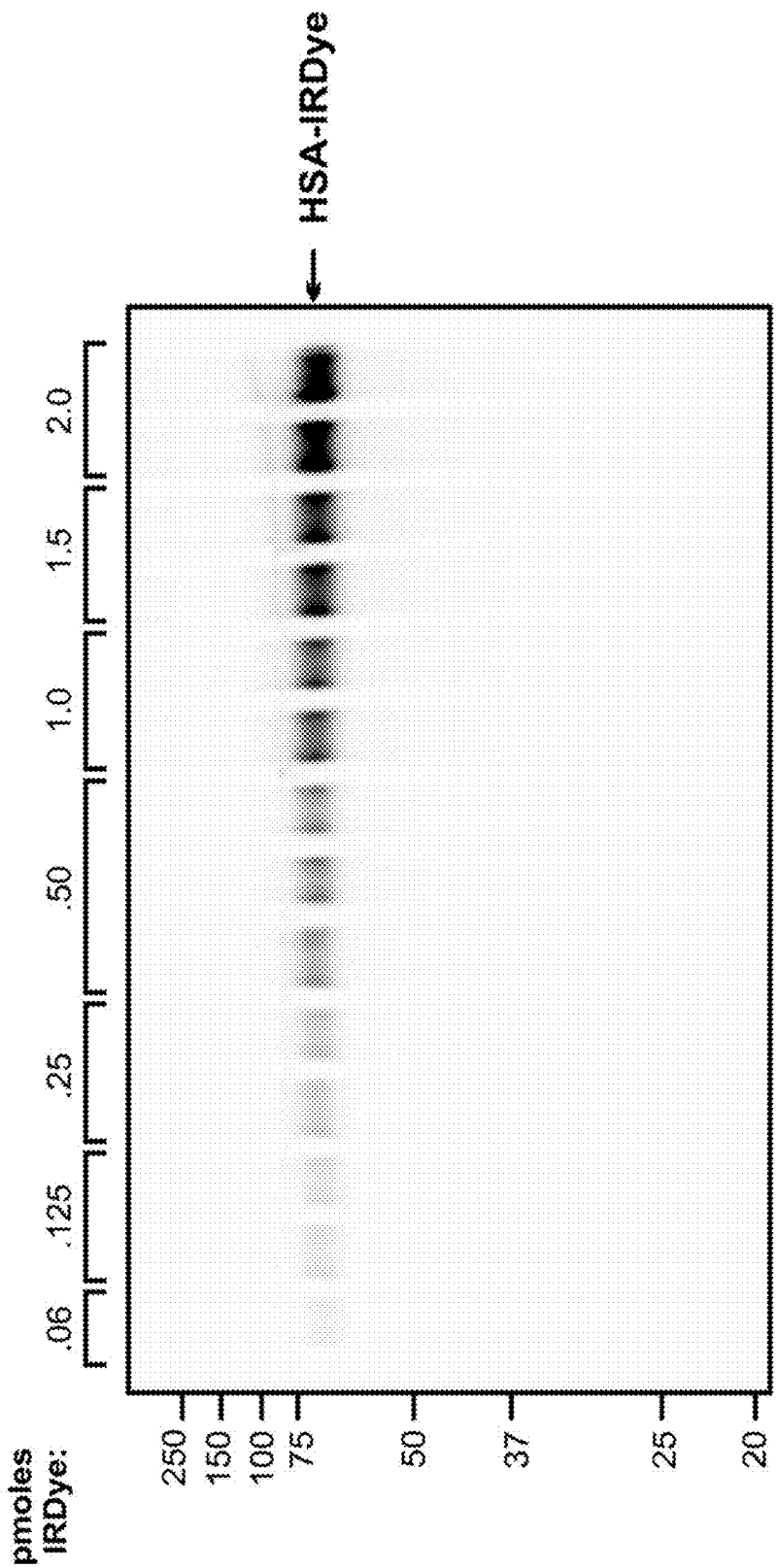
FIG. 23 depicts labeling and quantitative analysis of HSA-IRDye conjugates.
Figure 24:
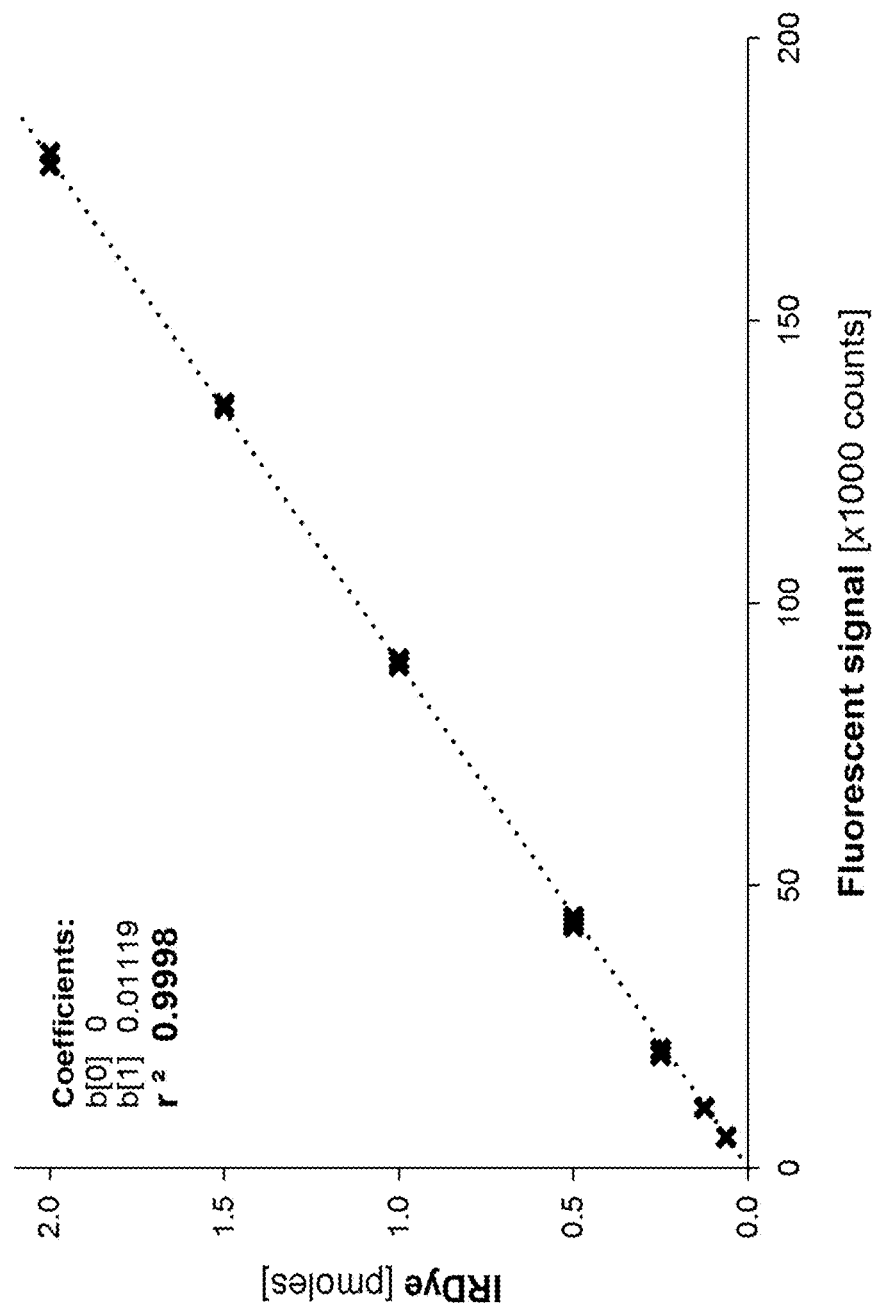
FIG. 24 depicts HSA-IRDye standard-signal response analysis.

For the introduction of multiple diverse payloads, cysteines, homocysteines, azido-lysines, propargylglycines, and the like, can be "mixed and matched" to introduce diverse payloads as exemplified schematically in FIG. 16, showing propargylglycine and an E-azidolysine being labeled sequentially and selectively.

As well, constituent propargylglycine or E-azidolysines and cysteine moieties of a peptide auxiliary can be labeled independently by methods known in the click chemistry art to provide two diverse payloads on the auxiliary. To reduce the effective hydrophobicity of the auxiliary, PEG chains can be included as part of the linkage to the reactive click functions and/or can be deployed as attachments to epsilon-amino groups of lysine constituents or the carboxyls of aspartate and glutamate residues, strategically positioned in the peptide chain of the auxiliary.

The utilization of diverse payloads allows for applications involving combination drug therapy in which drugs of diverse mechanisms of action manifest synergies that increase efficacy and reduce toxicity and drug resistance. For targeting two symmetrically disposed sites on the antibody surface, an auxiliary containing the constituent amino acids, propargylglycine, E-azidolysine and two differentially protected cysteines, will allow for four distinct entities to be positioned on the peptide auxiliary at both sites. "Unnatural" amino acids such as 4'-formylphenylalanine and 4'-chloromethylphenylalanine, can also be exploited using reductive alkylation and $S_N2$ reactions, respectively to extend the concept to several diverse conjugates. Just as a cysteine moiety in an auxiliary can serve as a precursor to a propargyl thioether, 4'-chloromethyl-phenylalanine can serve as a precursor to a 4'-azidomethylphenylalanine, providing additional flexibility for the introduction of payloads.

As per the site-selective labeling of a Fab entity of an antibody, Fc fragments of antibodies are also subjects of this invention using traceless affinity labels to conjugate OREs site-selectively. Targeted libraries, aimed at a consensus binding site on Fc can be based on the cyclic disulfide peptide DCAWHLGELVECYNH$_2$ (Convergent solutions to binding at a protein-protein interface., Science. 2000, 287 (5456):1279-83. DeLano W L, Ultsch M H, de Vos A M, Wells J A) or the high affinity peptide below described with U and ┌─────────────────────────────────────────────┐
— LPro-Asp-U-Ala-Trp-X-Leu-Gly-Glu-Leu-Val-Trp-U'-Thr-DPro —
└─────────────────────────────────────────────┘

U' in disulfide form in Dias RLA et al. in Protein ligand design: from phage display to synthetic protein epitope mimetics in human antibody Fc-binding peptidomimetics. J Am Chem Soc. 2006 128 :2726-32.

These peptides have high affinity for an Fc consensus binding site described in De Lano W L et al. and Dias RLA et al. and can be modified in several novel ways to facilitate acyl transfer to antibody Fc fragments, of linkers containing OREs.

For example, the DeLano cyclic disulfide derived from cysteines vide supra, can be replaced by analogous amide functions derived from aspartate and 2,3-diaminopropionic acid (Dap) entities and the like,) D-Dap-AWHLGELVE-D-$YNH_2$). The nucleophilicity of histidine, which may prohibit the use of acylators, can be avoided by using libraries that replace histidine with other amino acid residues (such as the isostere 3-(4-thiazolyl)-L-alanine and (R)- or (S)-2-amino-3-(thiazol-5-yl)propanoic acid). Peg units can then be attached to the cyclic peptide framework, terminating with amine-reactive functions that are positioned on the antibody surface proximal to an amino group of a lysine residue.

For example a method for labeling the Fc fragment of an antibody, site-selectively, utilizes the cyclic disulfide peptide $NH\{[(ZCH_2CH_2O)_n(CH_2)_mL]CHCH_2CO_2H\}$CAWXLGELVECY, (joined at cysteines) where X may be histidine, 3-(4-thiazolyl)-L-alanine, (R)- or (S)-2-amino-3-(thiazol-5-yl)propanoic acid); n=0-25; m=0-20; and Z=OREs such as, alkyne, cycloalkyne, azide, nitrile oxide, and nitrone; J=O, S; P=electron withdrawing substitutents such as nitro or cyano; L may represent any of the foregoing linkers capable of acylating or alkylating a lysine residue including those below.

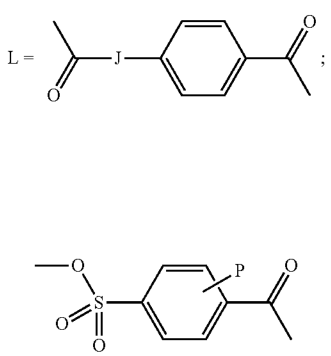

This approach is embodied in the general formula that follows.

Yet another strategy employing acyl transfer for labeling of the Fc fragment, utilizes histidine carbamates, (the substitution is shown below), for trapping protein nucleophiles: Fujishima et al., Ligand-Directed Acyl Imidazole Chemistry for Labeling of Membrane-Bound Proteins on Live Cells, *J. Am. Chem. Soc.,* 2012, 134 (9), pp 3961-3964.

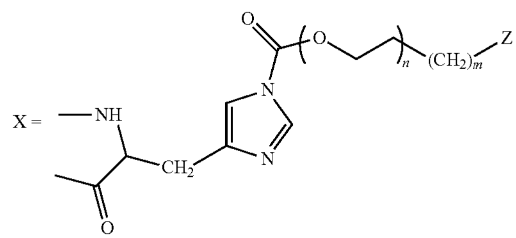

n = 1-25; m = 0-15

Z=alkyne, cycloalkyne, azide, nitrile oxide, nitrone, trans-cyclooctene, tetrazine A more subtle strategy exploits 2- or 4-fluoro-imidazole replacements of the imidazole rings of histidines which have much lower pKa values of ~1.22 and ~1.76 respectively, than the parent ($pK_a$~6). Consequently, these fluorinated histidines are also far more resistant to protonation at physiological pH. Therefore, acyl transfers from the fluoro-imidazoles can be controlled and implemented at such pH's, whereas acyl histidines can be labile to hydrolysis.

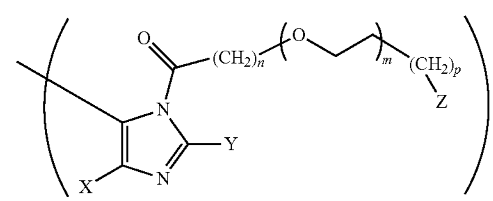

n = 1-25; m = 0-15, p = 0-1
X = H, Y = F
X = F, Y = H

Z=alkyne, cycloalkyne, azide, nitrile oxide, nitrone, trans-cyclooctene, tetrazine 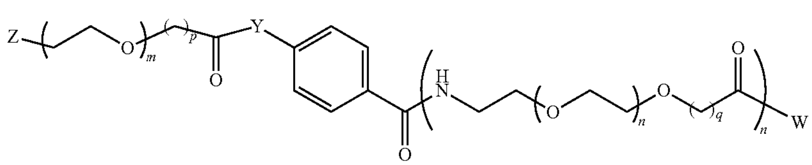 W═Asp-Dap-Ala-Trp-X-Leu-Gly-Glu-Leu-Val-Trp-Asp-Thr Z=alkynyl or cycloalkynyl, N═N═N⁻, formyl, acetyl, Diels-Alder diene, nitrile oxide, nitrone, trans-cyclooctene or tetrazine; m=0-30; p=1-20; n=1-20; Y═O, S, Se; q=1-2; X may be histidine, 3-(4-thiazolyl)-L-alanine, (R)- or (S)-2-amino-3-(thiazol-5-yl)propanoic acid).

Still another method of labeling the antibody based on the 13-mer motif is to substitute histidine with propargylglycine and then condense the azido-amine to provide an amino-triazole that can be acyl-functionalized to transfer as below, to provide a traceless linker.

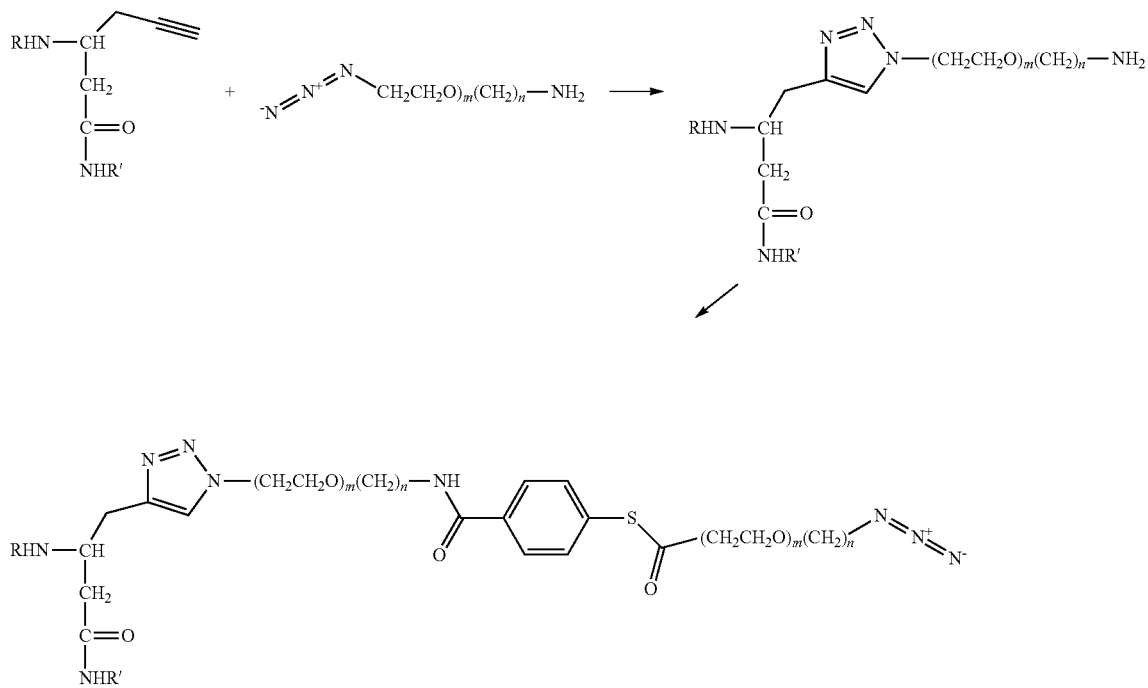

In another aspect, provided herein is a compound of formula (XVII):

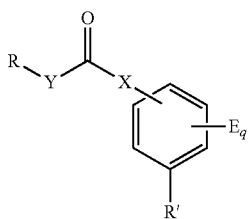

(XVII)

wherein

E is a moiety selected from the group consisting of halogen, —CN, —NO$_2$, —SO$_2$, —SO$_2$NHW$^4$, —S(O)C$_1$-C$_6$ alkyl, —S(O)aryl, and —OC$_1$-C$_6$ alkyl;

X is O, S or Se;

Y is a linker selected from the group consisting of alkyl, polyalkylene oxide, peptide, peptoid, and combinations thereof;

R is selected from the group consisting of an alkyne, cycloalkyne, azide, 1,3-diene, nitrile oxide, nitrone, tetrazine, trans-cyclooctene, and carbonyl (e.g., aldehyde); and R' is absent or is —C(O)OH, —C(O)OC$_1$-C$_6$ alkyl, —C(O)NH$_2$, —C(O)NHC$_1$-C$_6$ alkyl, —C(O)N(C$_1$-C$_6$ alkyl)$_2$, —SO$_2$NH$_2$, —SO$_2$NHC$_1$-C$_6$ alkyl, or —SO$_2$N(C$_1$-C$_6$ alkyl)$_2$;

W$^4$ comprises a peptide of up to 25 residues, linked to C(O) or SO$_2$ at the N-terminus; and q is 0, 1, 2 3 or 4.

In an embodiment, the compound of formula (XVII) has the structure of formula (XVIII):

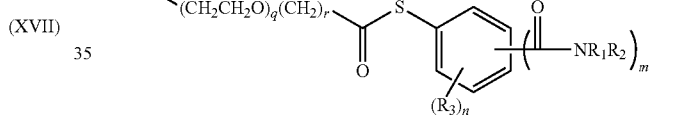

(XVIII)

wherein

R is selected from the group consisting of an alkyne, cycloalkyne, azide, 1,3-diene, nitrile oxide, nitrone, tetrazine, trans-cyclooctene, and carbonyl (e.g., aldehyde);

R$_1$ is hydrogen or C$_1$-C$_6$-alkyl;

R$_2$ is hydrogen or C$_1$-C$_6$-alkyl;

R$_3$ is an electron-withdrawing group (e.g., haloalkyl, —F, —NO$_2$ or —CN); and q is 0-100; r is 1-20; m is 0-1; and n is 0-4.

In a particular embodiment, the compound of formula (XVIII) has the structure of formula (XIX):

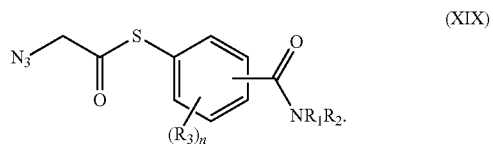

(XIX)

EXAMPLES

Materials and Methods

Compounds were prepared from commercially available starting materials using routine techniques of organic synthesis (see *Advanced Organic Chemistry: Reactions, Mechanisms and Structure*, 4th Ed; March, Jerry; 2006).

The peptides were prepared using Fmoc-Rink Amide MBHA resin (loading 0.42 mM/g). The Fmoc protecting group was removed with 20% piperidine solution in DMF (1×2 min followed by 1×20 min). Each coupling reaction was achieved using a 3-fold excess of amino acid and 3-fold excess of HBTU in presence of 6-fold excess of DIEA (40 min). Reaction completion was monitored by Kaiser test. The thiophenol moiety was attached to the lysine side chain using the Fmoc-Lys(Aloc) derivative as follows. The N-epsilon-alloxycarbonyl group was removed using tetrakis(triphenylphosphine) palladium(0) (0.25 eq) in the presence of phenylsilane (24 eq) in DCM (2×20 min). 4-(methyldisulfanyl) benzoic acid (3-fold excess) was then coupled to the epsilon-amino group using HBTU (3-fold excess) in is the presence of 6-fold excess of DIEA (20 min). Indole-3-butyric acid (4-(3-Indolyl)butyric acid) (3-fold excess) was then coupled to the alpha-amino group using HBTU (3-fold excess) in the presence of 6-fold exess of DIEA (20 min). The 4-(methyldisulfanyl) moiety was reduced with 1,4-Dithiothreitol (3-fold excess) in the presence of 6-fold excess of DIEA (2×20 min). Thioester formation was carried out using 2-azidoacetic acid (3-fold excess), PyBOP (3-fold excess) and DIEA (6-fold excess) (20 min).

The resin was washed with DCM, and a mixture of 95/2.5/2.5 TFA/TIS/Water was added. After 2 hours the mixture was concentrated under a stream of nitrogen, and the peptide was precipitated with cold diethyl ether. The mixture was centrifuged for 5 minutes at 4000 rpm. The supernatant was decanted, and the peptide pellet was dried in a dessicator.

Example 1

Figure 25:
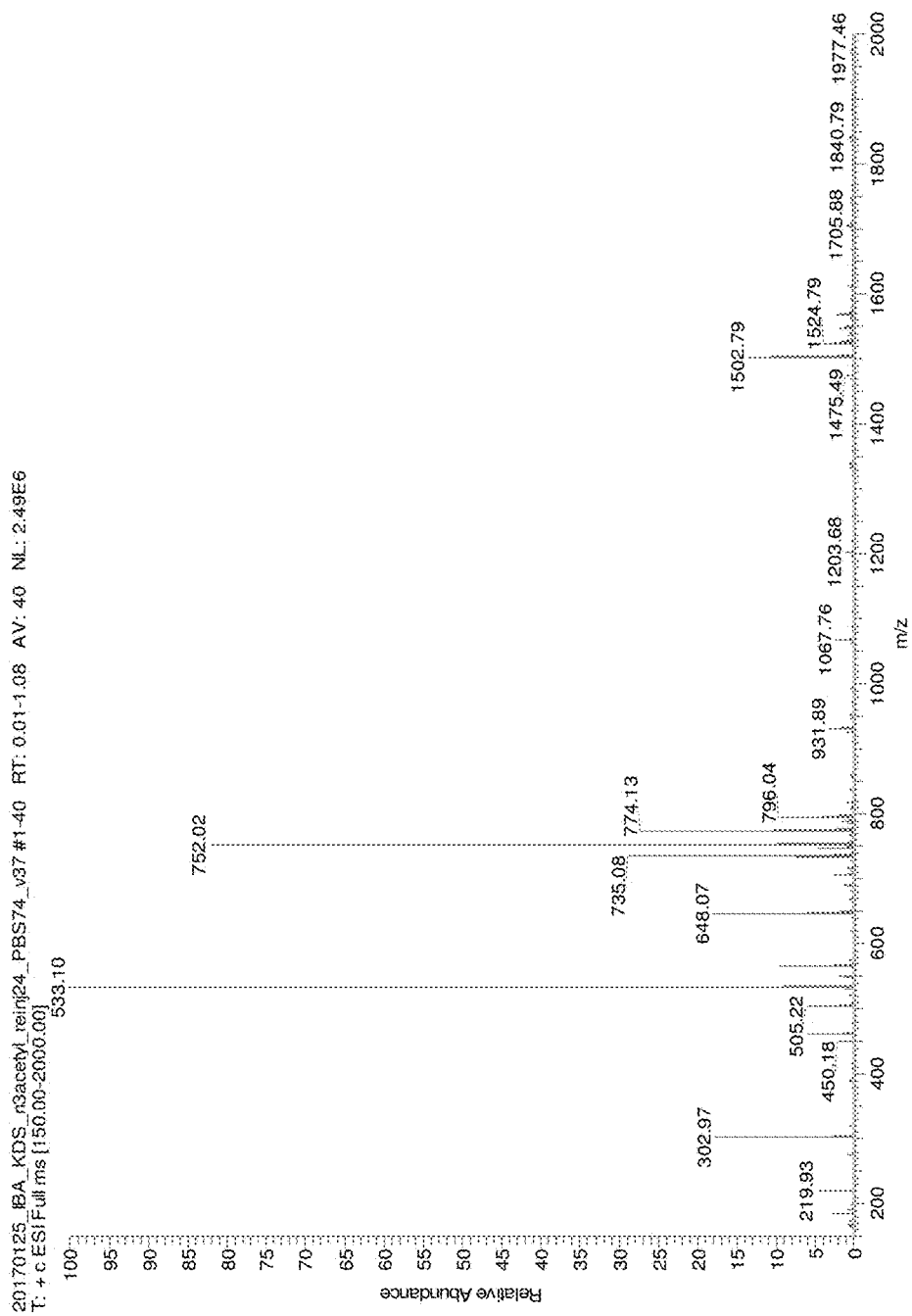
FIG. 25 depicts the mass spectrum of compound 2 of Example 1.
Figure 26:
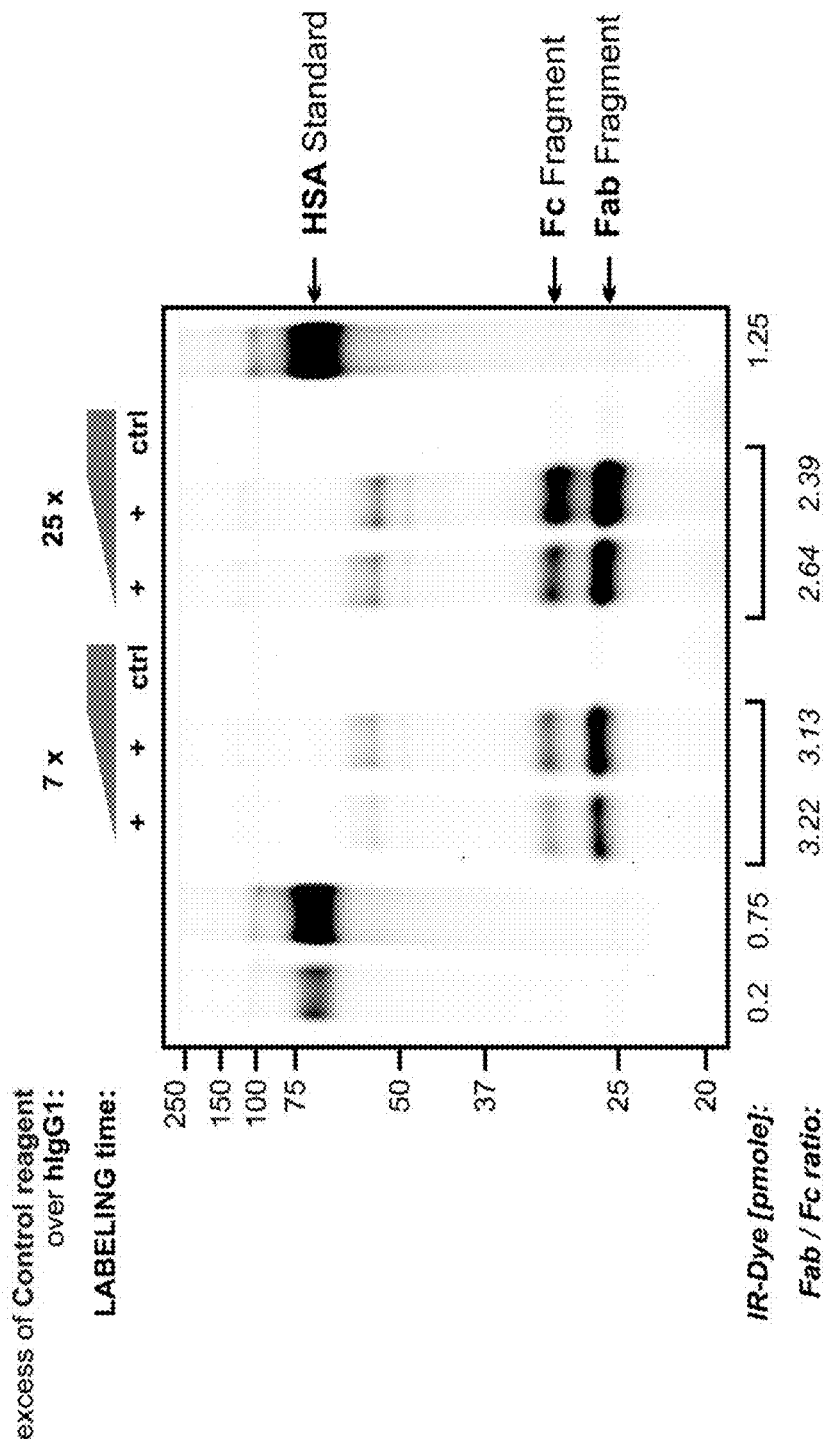
FIG. 26 depicts non-specific (control) labeling of Trastuzumab using one step DBCO IRDye-based quantitation.
Figure 27:
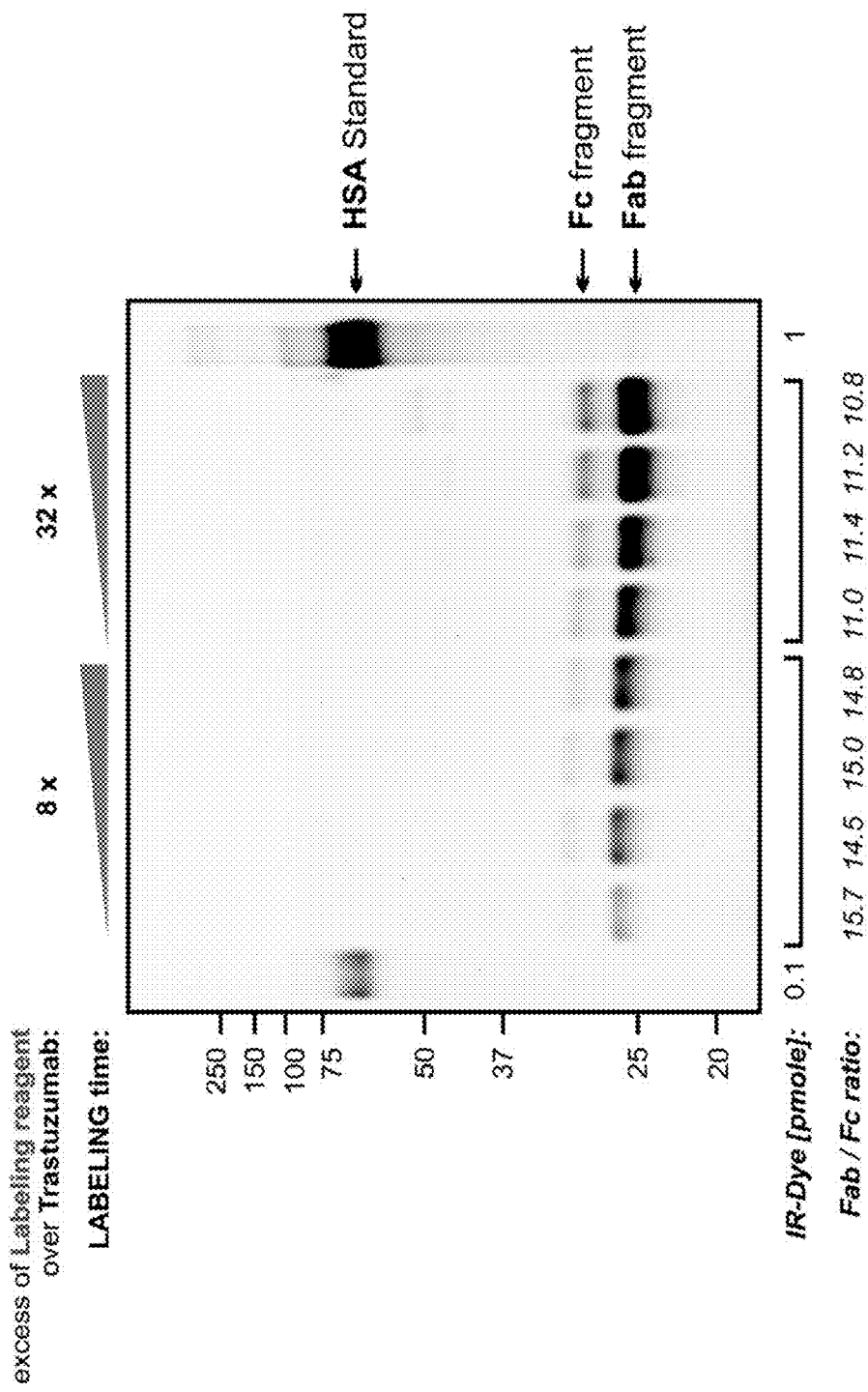
FIG. 27 depicts site-selective labeling of Trastuzumab using one step DBCO IRDye-based quantitation.
Figure 28:
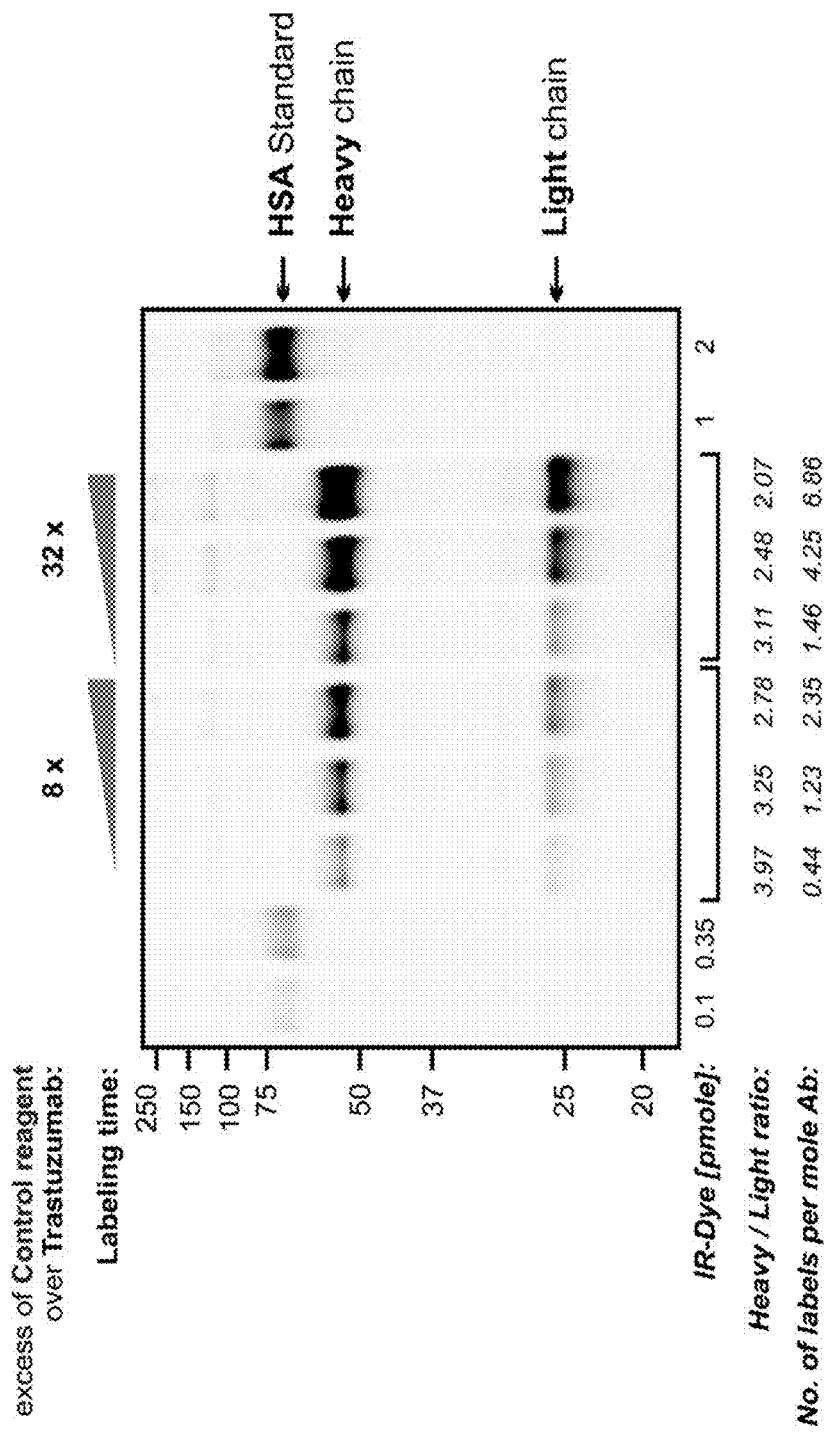
FIG. 28 depicts non-specific (control) labeling of Trastuzumab using one step DBCO IRDye-based quantitation.
Figure 29:
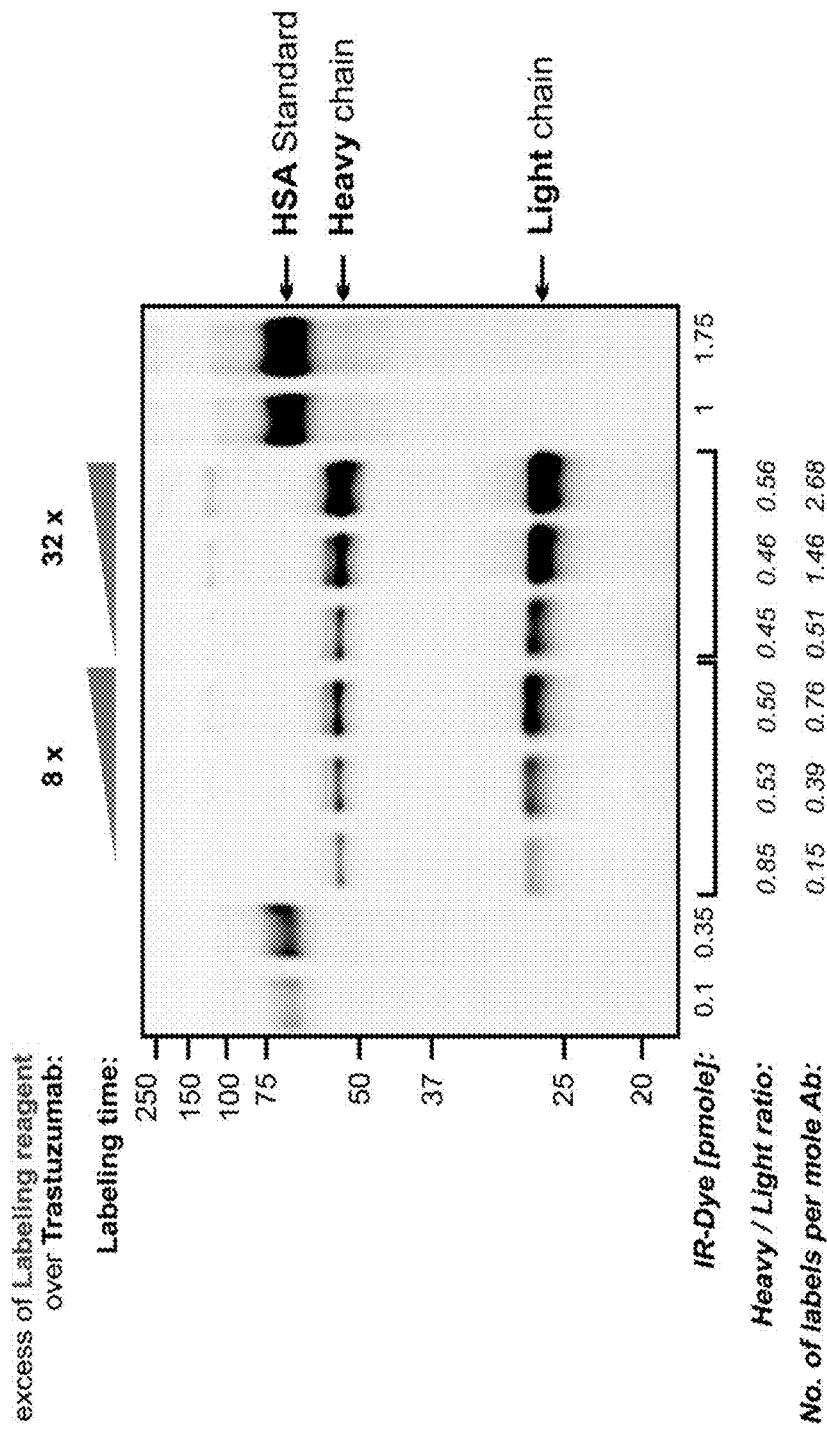
FIG. 29 depicts site-selective labeling of Trastuzumab using one step DBCO IRDye-based quantitation.
Figure 35:
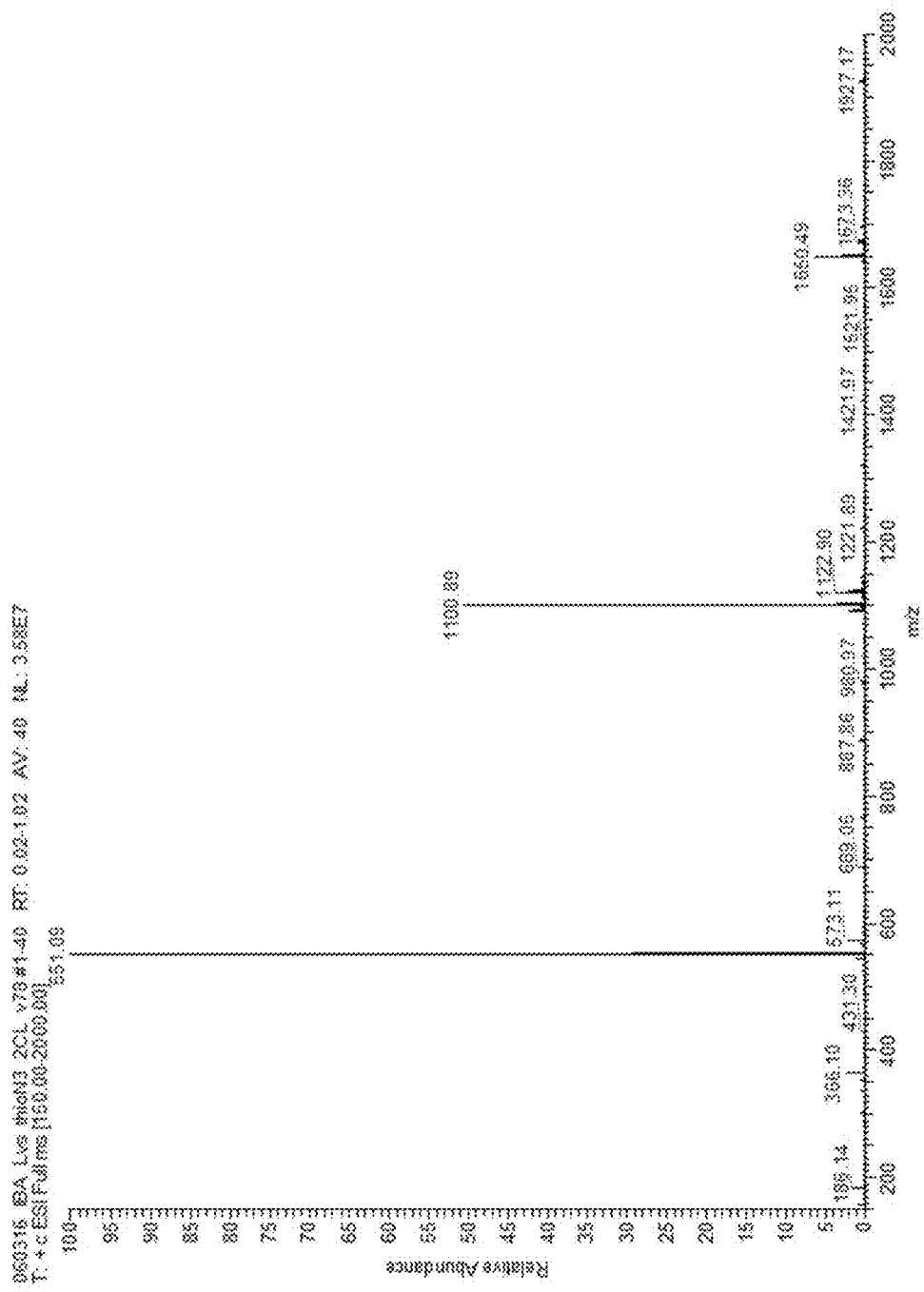
FIG. 35 depicts the mass spectrum of compound 1(a) of Example 1.
Figure 36:
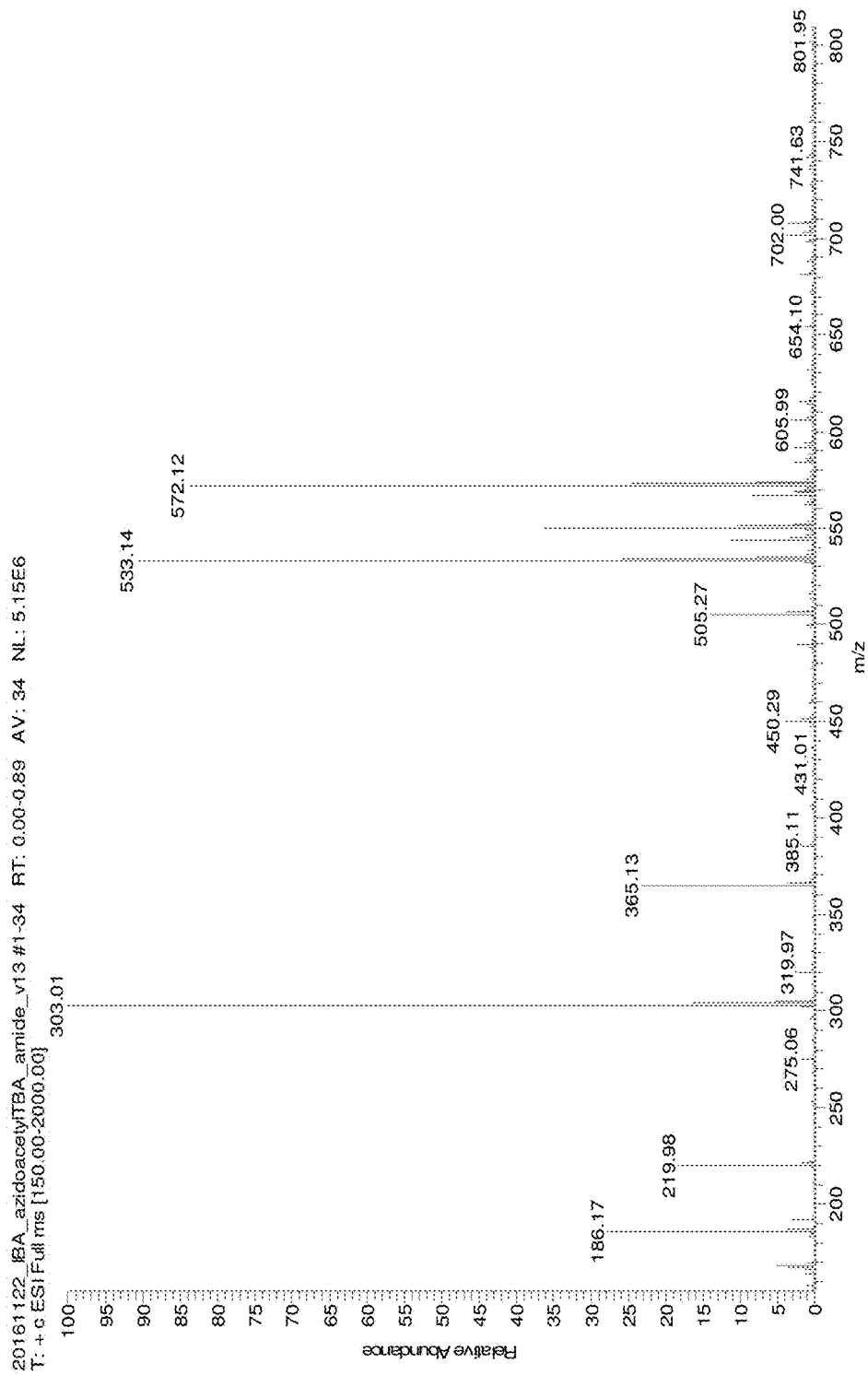
FIG. 36 depicts the mass spectrum of compound 1(b) of Example 1.

Compounds (1a), (1b), (2) and (3) were prepared and characterized by mass spectrum analysis.
Compound (1a): $M_{calc}$=551.2 [M+H]$^+$; Found 551.09 (See FIG. 35).
Compound (1b): $M_{calc}$=550.2 [M+H]$^+$; Found 572.2 [M+Na]$^+$ (See FIG. 36)
Compound (2): $M_{calc}$=752.3 [M+H]$^+$; Found 752.02 (See FIG. 25).

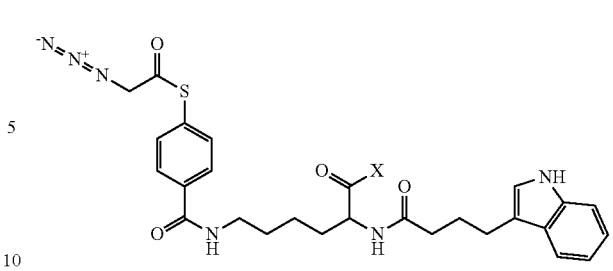

wherein
Compound (1a): X is —OH;
Compound (1b): X is —NH$_2$;
Compound (2): X is

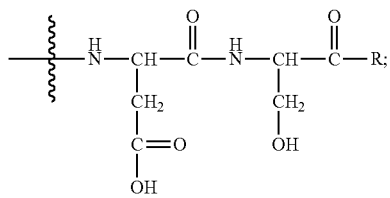

and R is —NH$_2$;
Compound (3); (See Example 2 below): X is

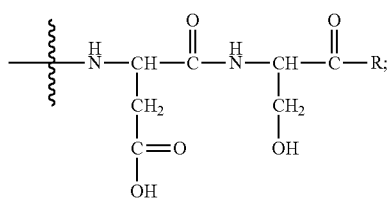

and
R is

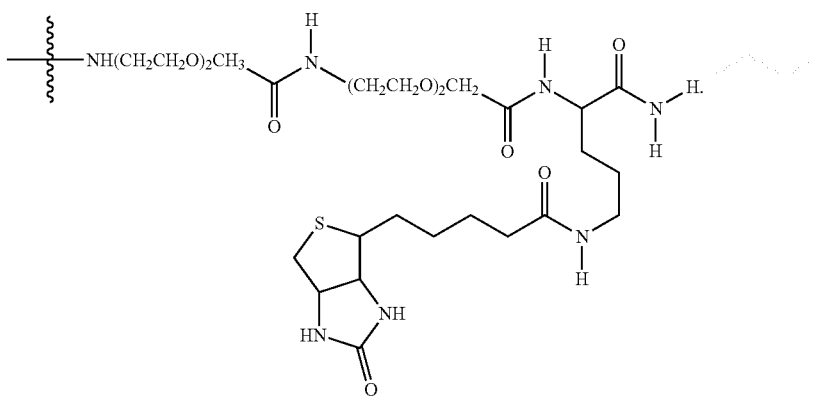

Example 2

Figure 30:
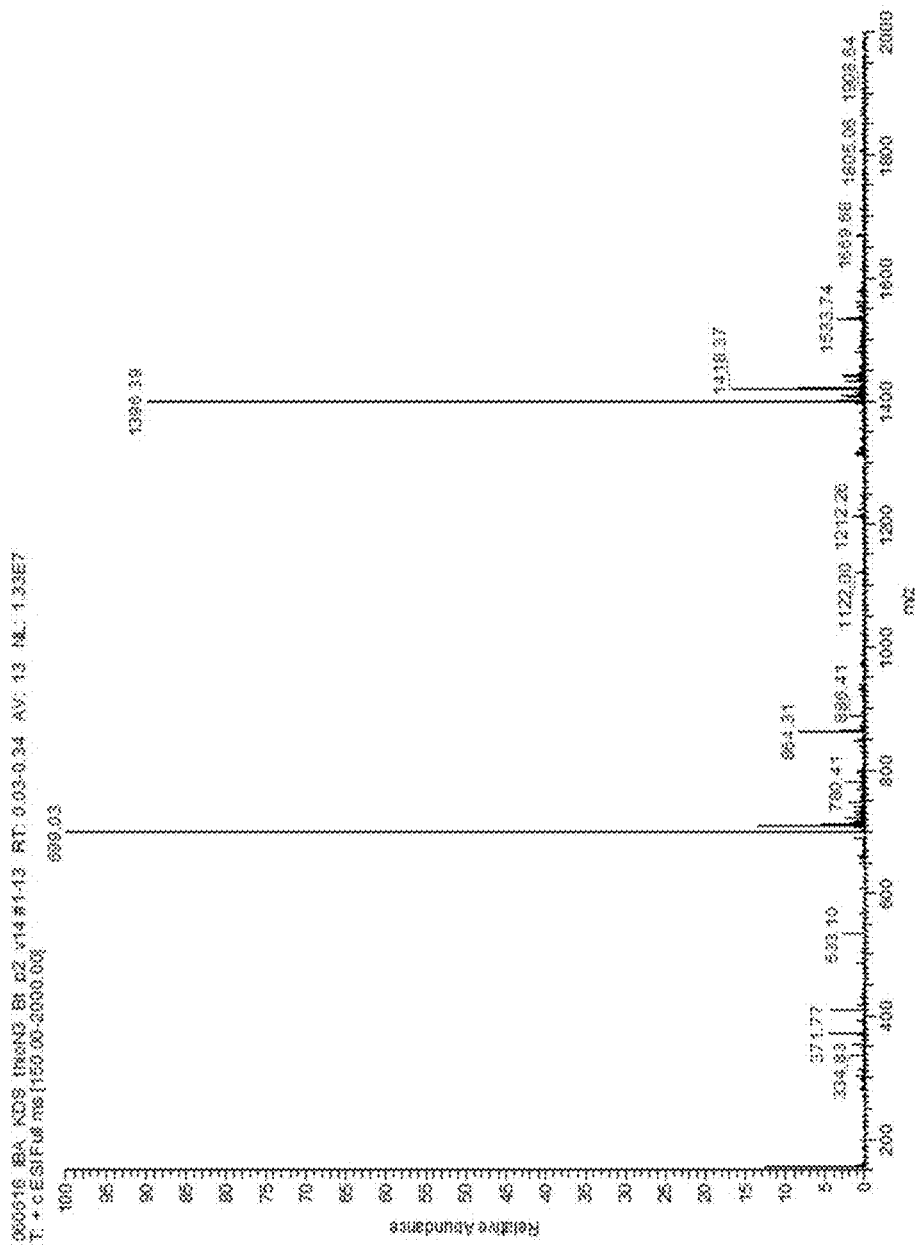
FIG. 30 depicts the mass spectrum of the compound of Example 2.

The following compound was synthesized, and structurally characterized by mass spectrum analysis. $M_{calc}$=1395.6; found=1396.39 (See FIG. 30).

Figure 31:
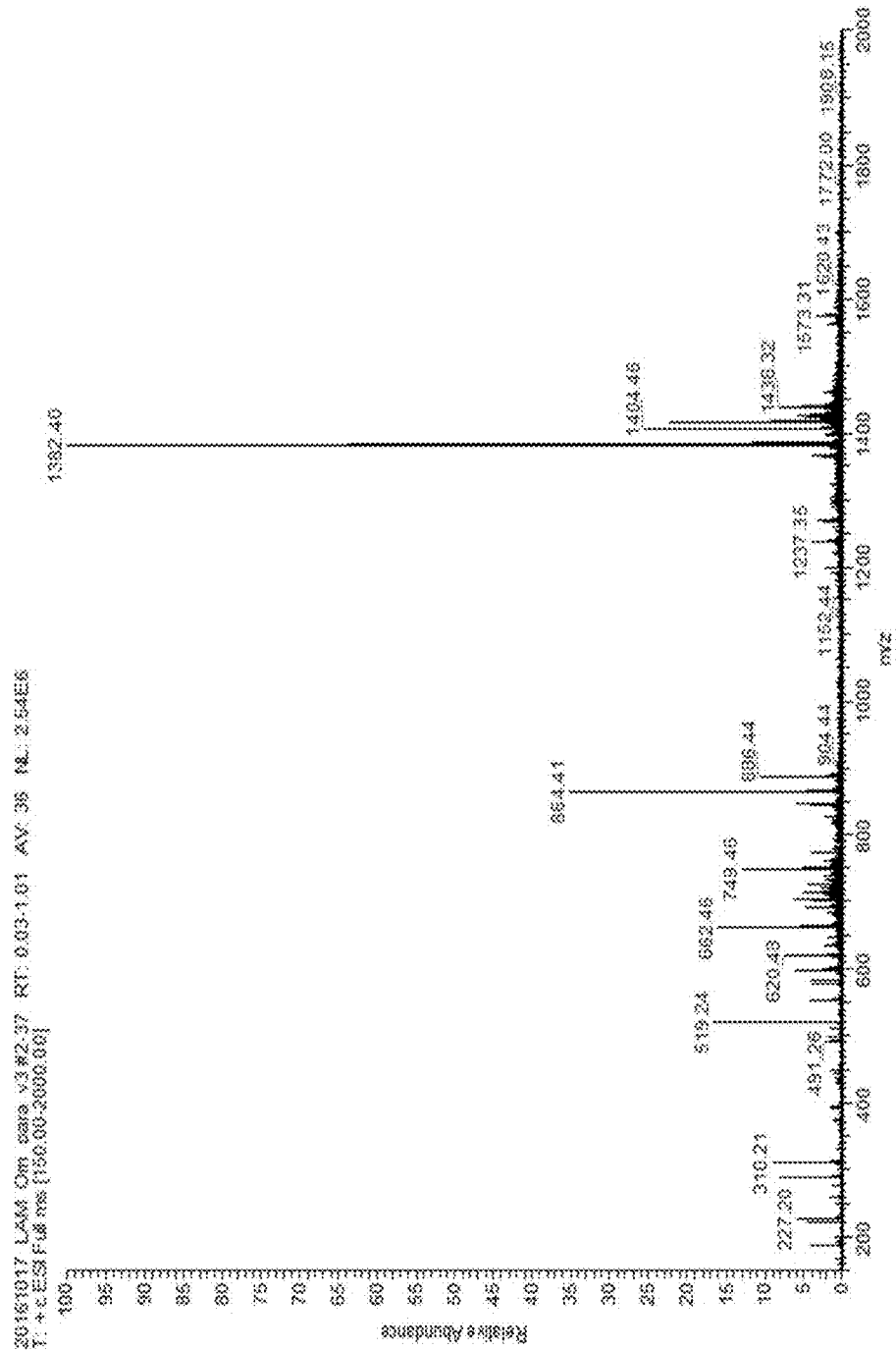
FIG. 31 depicts the mass spectrum of the compound of Example 3.
Figure 32:
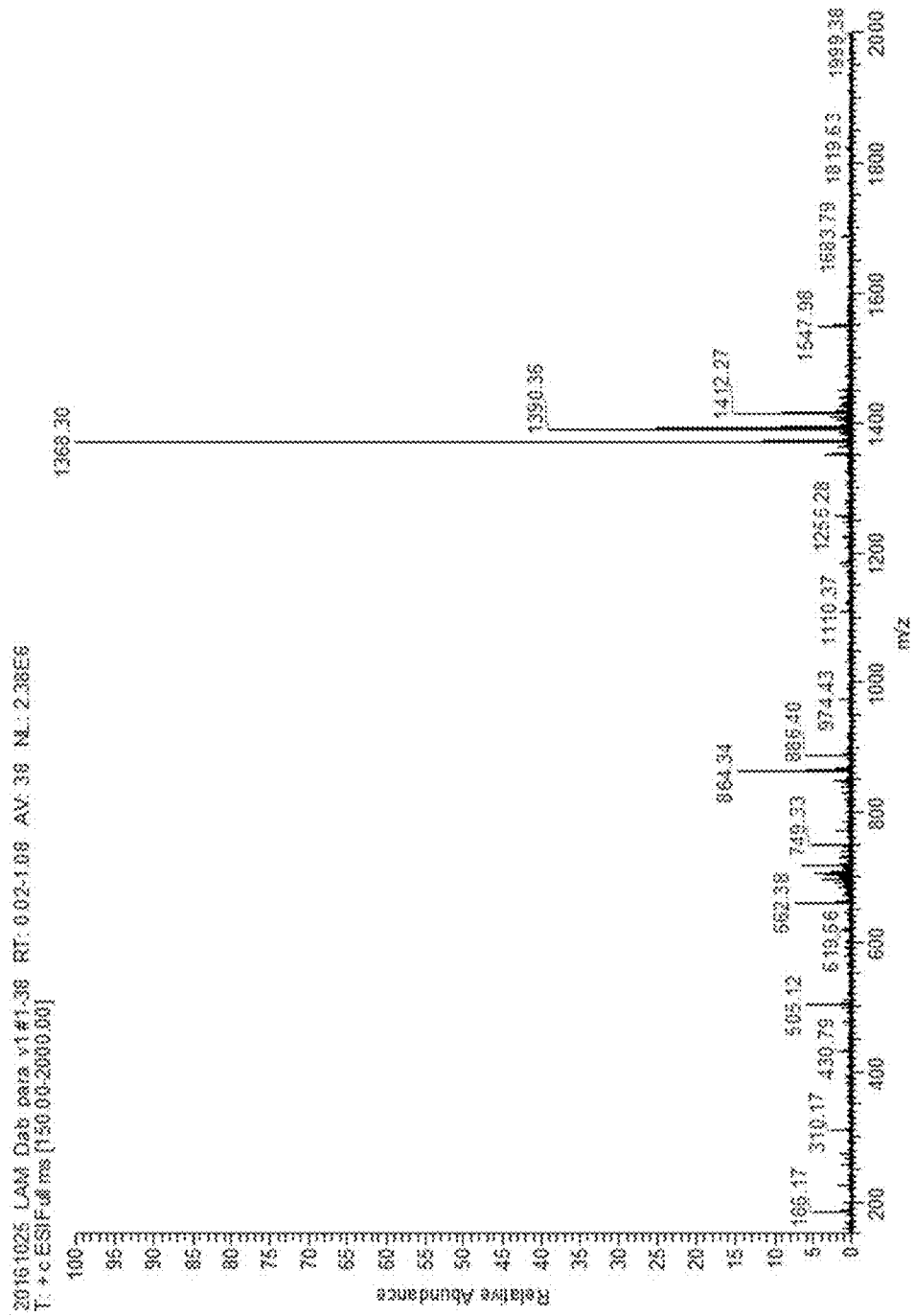
FIG. 32 depicts the mass spectrum of the compound of Example 4.

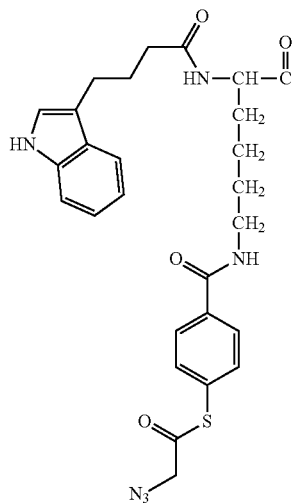
Example 3
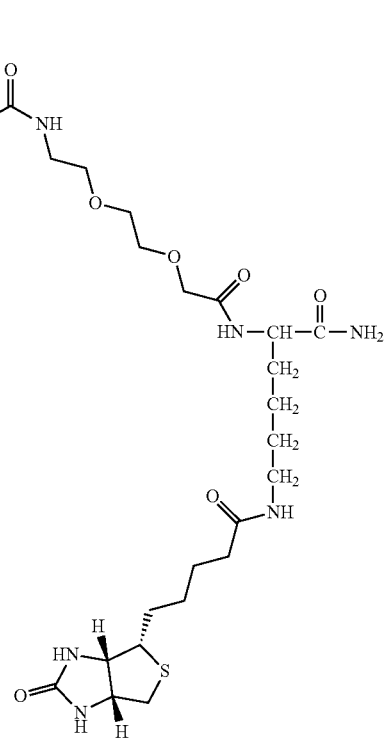
Example 4
The following compound was synthesized, and structurally characterized by mass spectrum analysis. $M_{calc}=1381.6$; found=1382.4. See FIG. 31.
The following compound was synthesized, and structurally characterized by mass spectrum analysis. $M_{calc}=1367.6$; found=1368.3. See FIG. 32.
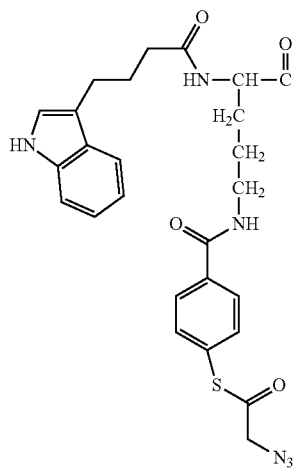
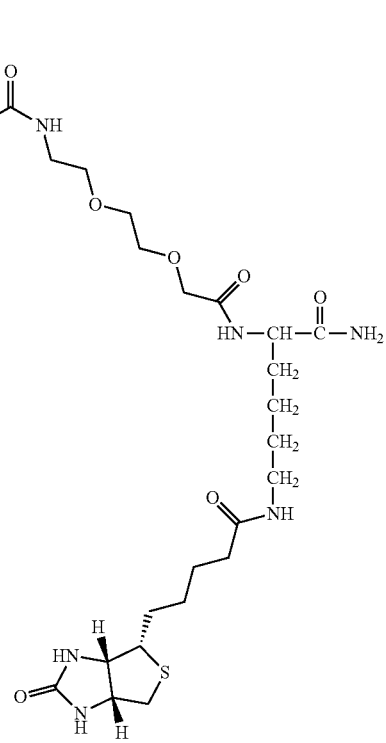

Figure 33:
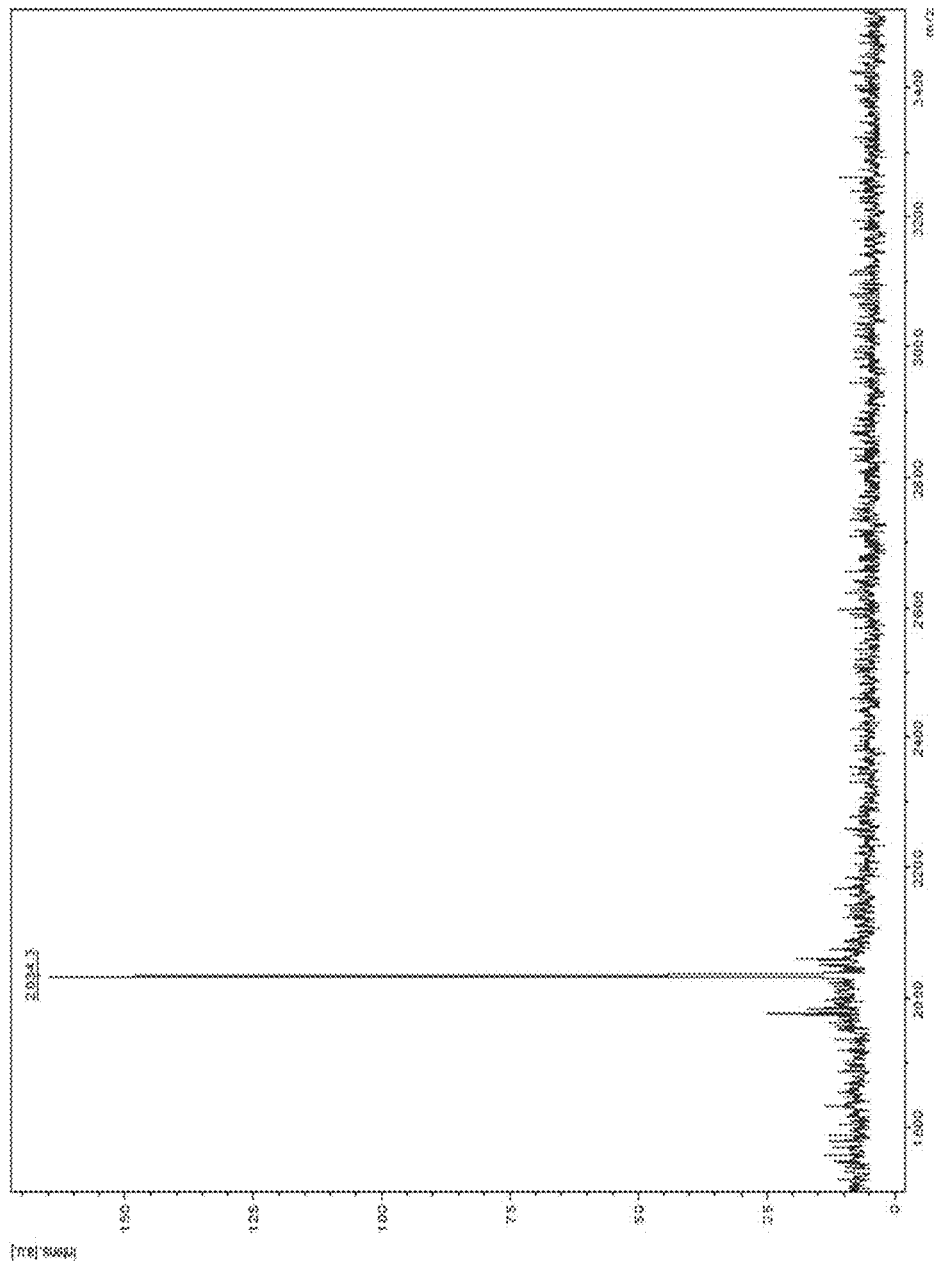
FIG. 33 depicts the mass spectrum of the compound of Example 5.
Figure 34A:
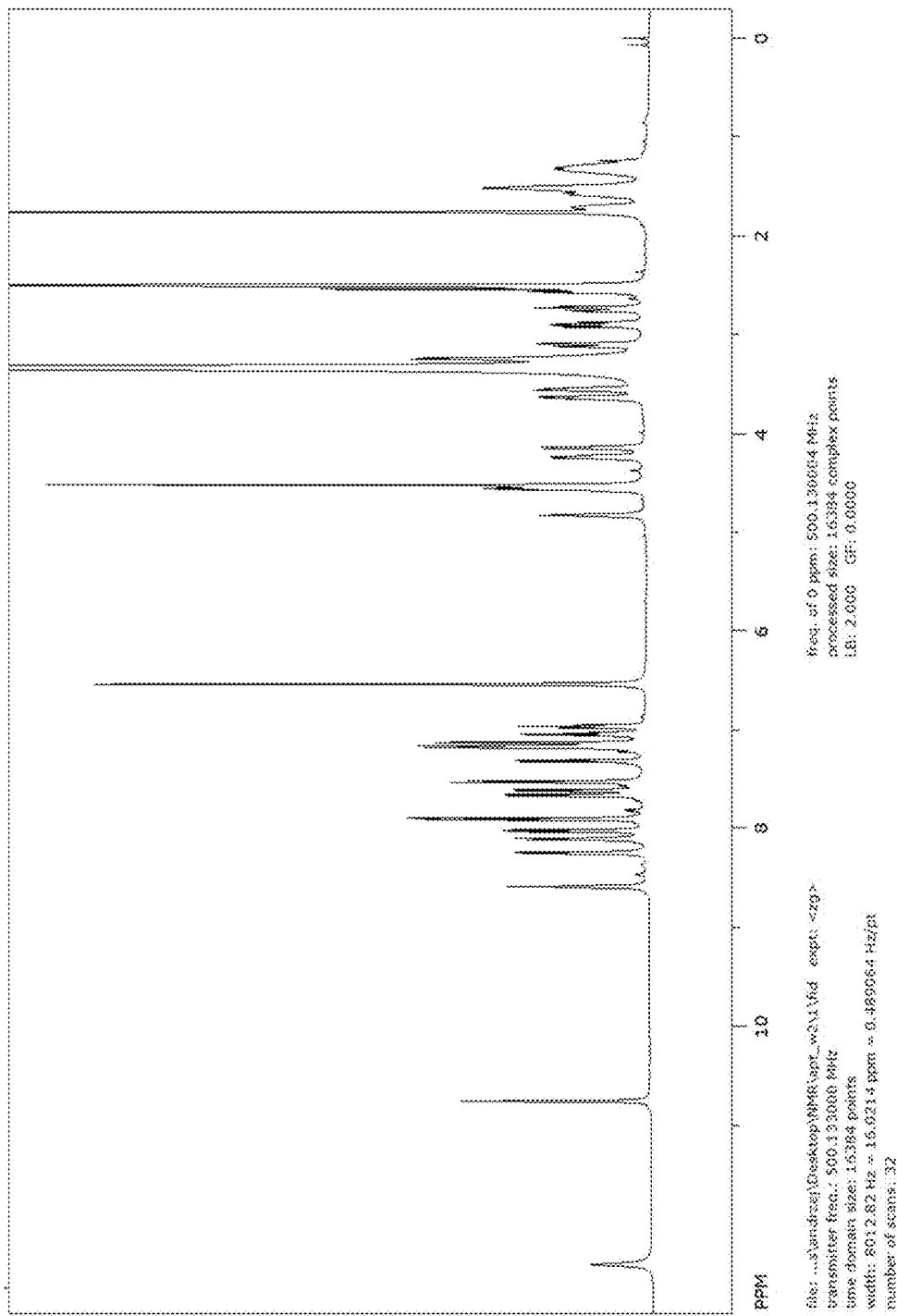
FIG. 34A depicts the HNMR spectrum of the compound of Example 6.
Figure 34B:
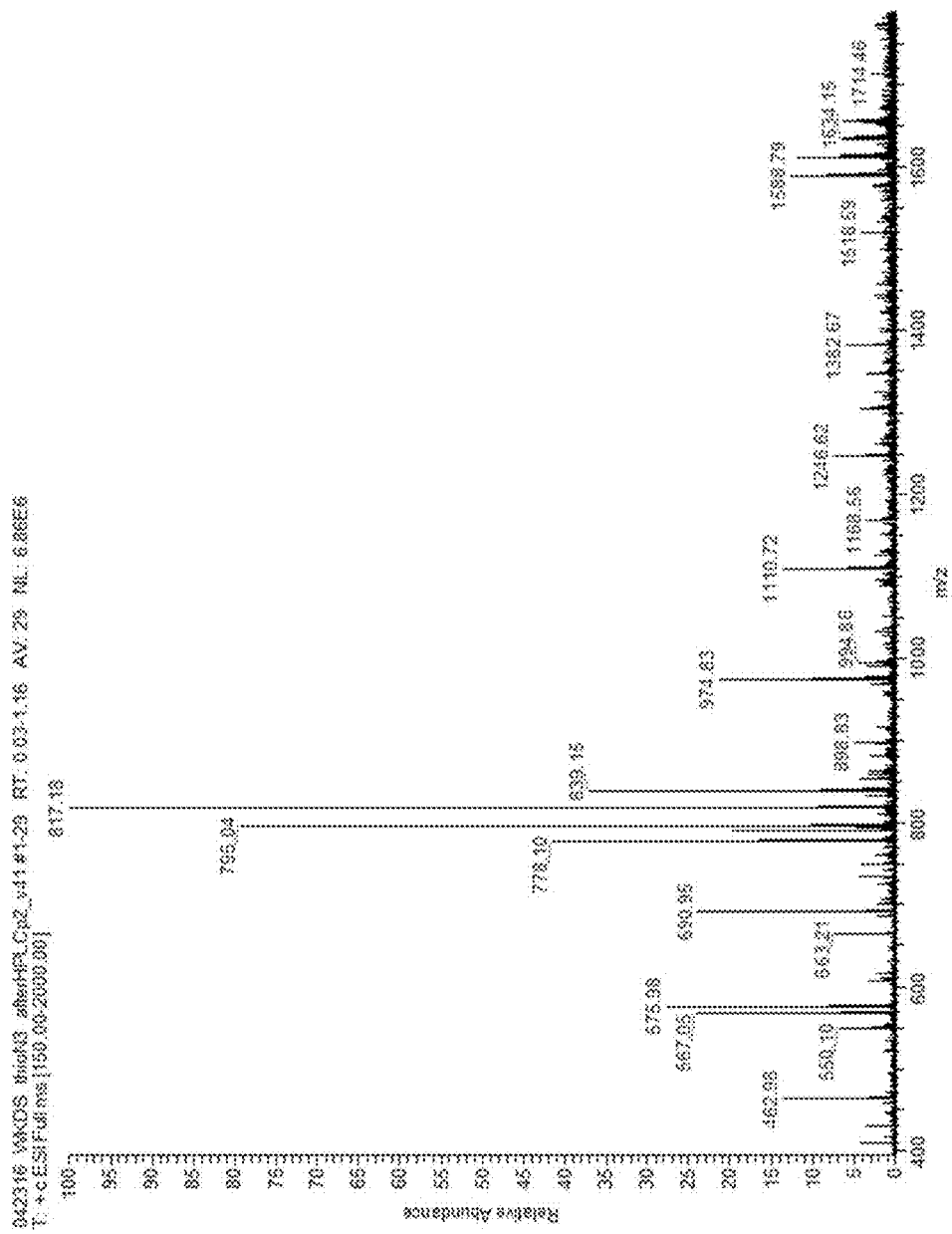
FIG. 34B depicts the mass spectrum of the compound of Example 6.

Example 5
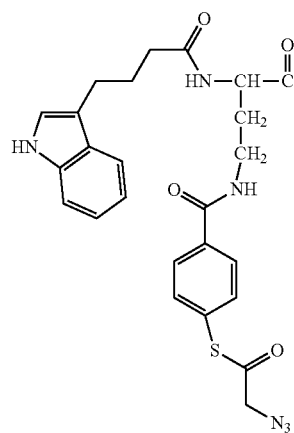
The following compound was synthesized, and structurally characterized by mass spectrum analysis. $M_{calc}$=2033.8; found=2034.3. See FIG. 33.
Example 6
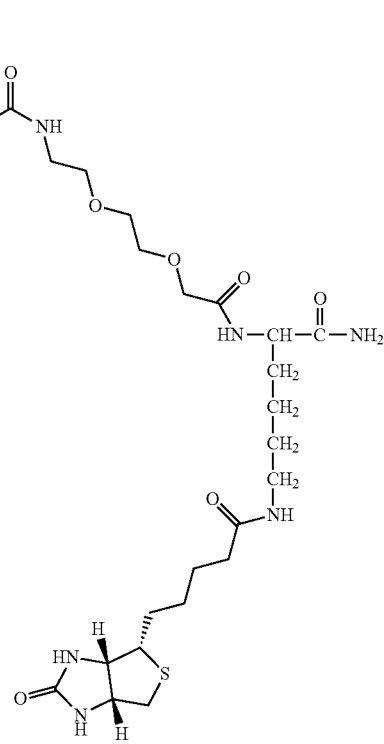
The following compound was synthesized, and structurally characterized by HNMR and mass spectrum analysis. $M_{calc}$=794.3; found=795.04. See FIG. 34A and FIG. 34B.
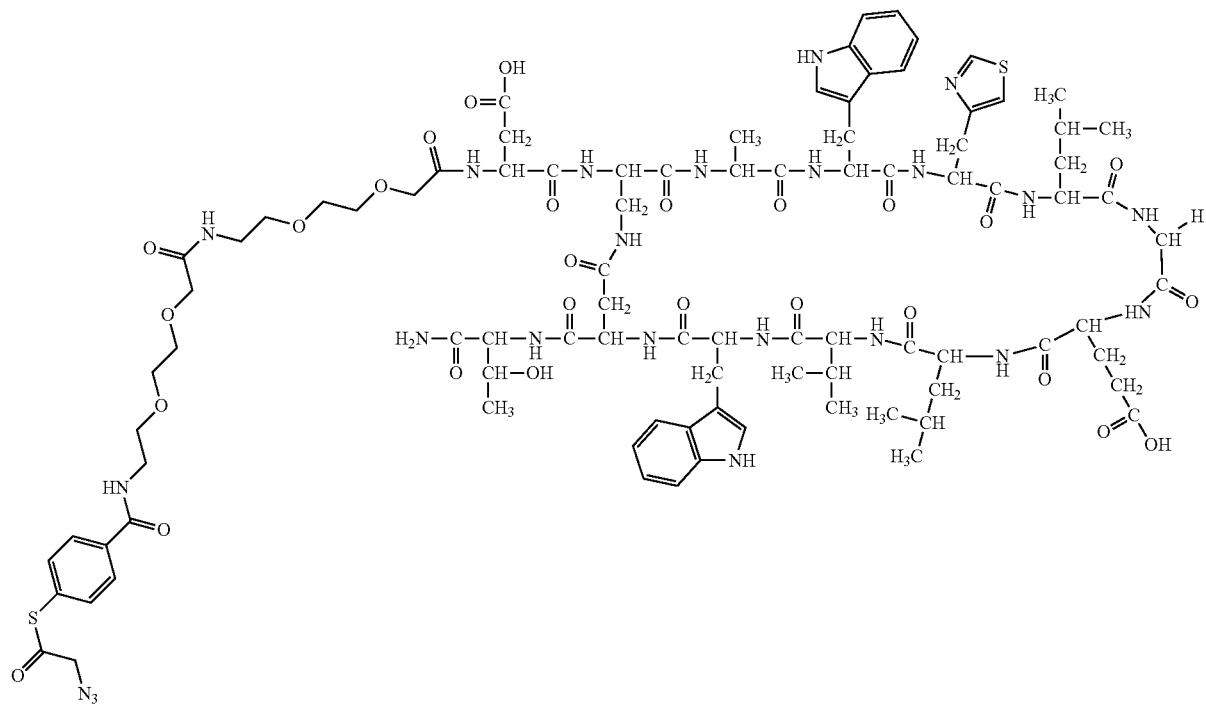 [SMILES: CC(C)CC1NC(=O)C(Cc2cscn2)NC(=O)C(Cc2c[nH]c3ccccc23)NC(=O)C(C)NC(=O)C(NC(=O)C(CC(=O)O)NC(=O)COCCOCCNC(=O)COCCOCCNC(=O)c2ccc(SC(=O)CN=[N+]=[N-])cc2)CNC(=O)CC(C(=O)NC(C(N)=O)C(C)O)NC(=O)C(Cc2c[nH]c3ccccc23)NC(=O)C(C(C)C)NC(=O)C(CC(C)C)NC(=O)C(CCC(=O)O)NC(=O)CNC1=O]

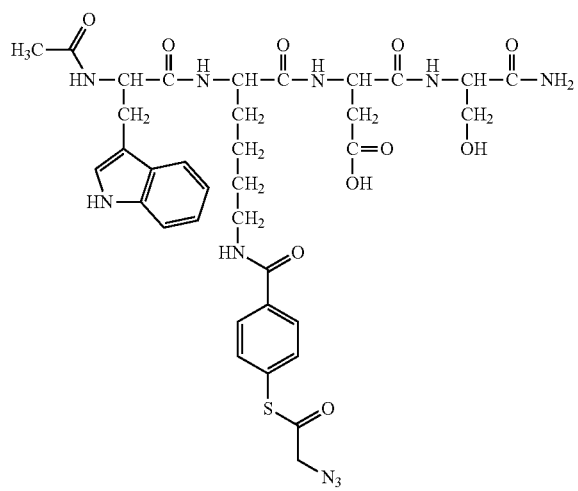 [SMILES: CC(=O)NC(Cc1c[nH]c2ccccc12)C(=O)NC(CCCCNC(=O)c1ccc(SC(=O)CN=[N+]=[N-])cc1)C(=O)NC(CC(=O)O)C(=O)NC(CO)C(N)=O]

The invention claimed is:
1. A compound of formula (XVII):

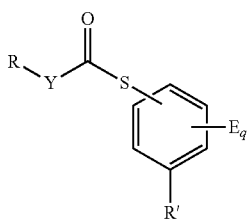

wherein
E is halogen or —SO$_2$NHW$^4$;
Y is a polyalkylene oxide;
R is azide;
R' is absent;
q is 4; and
W$^4$ is a compound of formula (XV):

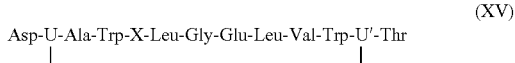

wherein
U and U' independently are cysteine, aspartate, glutamate, 2,3-diaminopropionic acid, lysine, or ornithine; and
X is histidine, 3-(4-thiazolyl)-L-alanine, (R)-2-amino-3-(thiazol-5-yl) propanoic acid or (S)-2-amino-3-(thiazol-5-yl) propanoic acid.

2. The compound of claim 1, wherein E is a halogen.

3. The compound of claim 2, wherein the halogen is fluorine.

* * * * *